(12) United States Patent
Bracken et al.

(10) Patent No.: US 7,381,813 B2
(45) Date of Patent: Jun. 3, 2008

(54) NUCLEIC ACIDS ENCODING ESTROGEN RECEPTOR LIGAND BINDING DOMAIN VARIANTS

(75) Inventors: Kathryn Rene Bracken, Morristown, NJ (US); Joseph Ernest de los Angeles, Cranford, NJ (US); Ying Huang, Olney, MD (US); Michael Joseph Kadan, Adamstown, MD (US); Gary Michael Ksander, Milford, NJ (US); Dennis Bryan Zerby, Myersville, MD (US)

(73) Assignee: Novartis AG, Basel (CH)

( * ) Notice: Subject to any disclaimer, the term of this patent is extended or adjusted under 35 U.S.C. 154(b) by 820 days.

(21) Appl. No.: 10/157,899

(22) Filed: May 31, 2002

(65) Prior Publication Data

US 2003/0143559 A1    Jul. 31, 2003

Related U.S. Application Data

(60) Provisional application No. 60/294,839, filed on May 31, 2001.

(51) Int. Cl.
| | | |
|---|---|---|
| C07H 21/04 | (2006.01) | |
| C07H 21/02 | (2006.01) | |
| C12N 15/00 | (2006.01) | |

(52) U.S. Cl. .................... 536/23.5; 536/23.1; 536/24.1; 435/320.1

(58) Field of Classification Search ...................... None
See application file for complete search history.

(56) References Cited

U.S. PATENT DOCUMENTS

| | | | | |
|---|---|---|---|---|
| 5,364,791 | A | | 11/1994 | Vegeto et al. ............. 435/320.1 |
| 5,534,619 | A | * | 7/1996 | Wakefield et al. .......... 530/324 |
| 5,874,534 | A | | 2/1999 | Vegeto et al. ................ 530/350 |
| 5,935,934 | A | | 8/1999 | Vegeto et al. .................. 514/44 |

FOREIGN PATENT DOCUMENTS

| | | |
|---|---|---|
| WO | WO 87/05049 | 8/1987 |
| WO | WO 93/23431 | 11/1993 |
| WO | WO 96/40911 | 12/1996 |
| WO | WO 98/18925 | 5/1998 |
| WO | WO 98/54311 | 12/1998 |
| WO | WO 00/23464 | 4/2000 |
| WO | WO 01/30843 | 5/2001 |
| WO | WO 02/06463 | 1/2002 |

OTHER PUBLICATIONS

Feil, et al. "Regulation of Cre Recombinase Activity by Mutated Estrogen Receptor Ligand-Binding Domains," Biochemical and Biophysical Research Communications. 237:752-757 (1997).*
Wang et al. Nuc. Acids Res. 27: 4609-4618, 1999.*
Kaufman et al. Blood 94: 3178-3184, 1999.*
Phillips A., J Pharm Pharmacology 53: 1169-1174, 2001.*
Beerli et al 2000. J Biol Chem 275:32617-32627.*
Kay et al. 2001. Nature Medicine 7:33-40.*
Thomas et al. 2003. Nature Reviews. Genetics. 4:346-358.*
Aumais, et al., "Selective Interaction of hsp90 with an Estrogen Receptor Ligand-binding Domain Containing a Point Mutation," *The Journal of Biological Chemistry*, 272(18):12229-12235 (May 2, 1997).
Belshaw, et al., "Cell-Specific Calcineurin Inhibition by a Modified Cyclosporin," *J. Am. Chem. Soc.*, 119:1805-1806 (1997).
Benihoud, et al., "Adenovirus Vectors for Gene Delivery," *Current Opinion in Biotechnology*, 10:440-447 (1999).
Bocchinfuso, et al., "Estrogen Receptor Residues Required for Stereospecific Ligand Recognition and Activation," *Molecular Endocrinology*, 11(5):587-594 (May 1997).
Braselmann, et al., "A Selective Transcriptional Induction System for Mammalian Cells Based on Ga14-Estrogen Receptor Fusion Proteins," *Proc. Natl. Acad. Sci. USA*, 90:1657-1661 (Mar. 1993).
Brzozowski, et al., "Molecular Basis of Angonism and Antagonism in the Oestrogen Receptor," *Nature*, 389:753-758 (Oct. 1997).
Burcin, et al., "Adenovirus-mediated Regulable Target Gene Expression In Vivo," *Proc. Natl. Acad. Sci. USA*, 96:355-360 (Jan. 1999).
Clackson, T., "Controlling Mammalian Gene Expression with Small Molecules," *Current Opinion in Chemical Biology*, 1:210-218 (1997).
Danielian, et al., "Identification of Residues in the Estrogen Receptor that Confer Differential Sensitivity to Estrogen and Hydroxytamoxifen," *Molecular Endocrinology*, 7:232-240 (1993).
Delort, et al., "TAXI/UAS: A Molecular Switch to Controll Expression of Gene In Vivo," *Human Gene Therapy*, 7:809-820 (May 1, 1996).
Eiler, et al., "Overexpression, Purification, and Crystal Structure of Native ER( LBD," *Protein Expression and Purification*, 22:165-173 (Jun. 2001).
Ekena, et al., "Determinants of Ligand Specificity of Estrogen Receptor-alpha: Estrogen versus Androgen Discrimination," *The Journal of Biological Chemistry*, 273(2):693-699 (Jan. 9, 1998).
Ekena, et al., "Different Residues of the Human Estrogen Receptor are Involved in the Recognition of Structurally Diverse Estrogens and Antiestrogens," *The Journal of Biological Chemistry*, 272(8):5069-5075 (Feb. 21, 1997).
Ekena, et al., "Identification of Amino Acids in the Hormone Binding Domain of the Human Estrogen Receptor Important in Estrogen Binding," *The Journal of Biological Chemistry*, 271(33):20053-20059 (1996).

(Continued)

*Primary Examiner*—Manjunath Rao
*Assistant Examiner*—Shulamith H Shafer
(74) *Attorney, Agent, or Firm*—MDIP LLC

(57) ABSTRACT

Mutants of steroid receptor ligand binding domains and synthetic ligands which have specific binding affinities for these receptors are provided. The use of these LBD-ligand combinations for construction of selective "molecular gene switches" is disclosed. Methods of regulating gene function using these switches are provided.

27 Claims, 14 Drawing Sheets

OTHER PUBLICATIONS

Eng, et al., "Different Classes of Coactivators Recognize Distinct but Overlapping Binding Sites on the Estrogen Receptor Ligand Binding Domain," *The Journal of Biological Chemistry*, 273(43):28371-28377 (Oct. 23, 1998).

Eng, et al., "Probing the Structure and Function of the Estrogen Receptor Ligand Binding Domain by Analysis of Mutants with Altered Transactivation Characteristics," *Molecular and Cellular Biology*, 17(8):4644-4653 (Aug. 1997).

Fawell, et al., "Inhibition of Estrogen Receptor-DNA Binding by the 'Pure' Antiestrogen ICI 164, 384 Appears to be Mediated by Impaired Receptor Dimerization," *Proc. Natl. Acad. Sci. USA*, 87:6883-6887 (Sep. 1990).

Feil, et al., "Ligand-activated Site-specific Recombination in Mice," *Proc. Natl. Acad. Sci. USA*, 93:10887-10890 (Oct. 1996).

Feil, et al., "Regulation of Cre Recombinase Activity by Mutated Estrogen Receptor Ligand-Binding Domains," *Biochemical and Biophysical Research Communications*, 237:752-757 (1997).

Gauthier, et al., "New Highly Stereoselective Synthesis of (Z)-4-Hydroxytamoxifen and (Z)-4-Hydroxytoremifene via McMurry Reaction," *J. Org. Chem.*, 61:3890-3893 (1996).

Giambiagi, et al., "Studies on the Activation of the Oestrogen Receptor Bound to the Anti-oestrogens 4-hydroxytamoxifen and ICI 164,384 by Using Three Monoclonal Antibodies," *Journal of Molecular Endochrinology*, 7:9-19 (1991).

Grese, et al., "Molecular Determinants of Tissue Selectivity in Estrogen Receptor Modulators," *Proc. Natl. Acad. Sci. USA*, 94:14105-14110 (Dec. 1997).

Grese, et al., "Structure-Activity Relationships of Selective Estrogen Receptor Modulators: Modifications to the 2-Arylbenzothiophene Core of Raloxifene," *Journal of Medicinal Chemistry*, 40(2):146-167 (1997).

Hollenberg, et al., "Use of a Conditional MyoD Transcription Factor in Studies of MyoD Trans-activation and Muscle Determination," *Proc. Natl. Acad. Sci. USA*, 90:8028-8032 (Sep. 1993).

Ince, et al., "Powerful Dominant Negative Mutants of the Human Estrogen Receptor," *The Journal of Biological Chemistry*, 268(19):14026-14032 (Jul. 5, 1993).

Indra, et al., "Temporally-controlled Site-specific Mutagenesis in the Basal Layer of the Epidermis: Comparison of the Recombinase Activity of the Tamoxifen-inducible Cre-ERT and Cre-ERT2 Recombinases," *Nucleic Acids Research*, 27(22):4324-4327 (1999).

International Search Report for PCT/US02/16946 (Nov. 19, 2002).

Koh, et al., "Selective Regulation of Gene Expression Using Rationally-Modified Retinoic Acid Receptors," *Journal of the American Chemical Society*, 121:1984-1985 (1999).

Kohno, et al., "Mutational Analysis of the Estrogen Receptor Ligand-Binding Domain: Influence of Ligand Structure and Stereochemistry on Transactivation," *Journal of Molecular Endocrinology*, 16:277-285 (1996).

Kraft, et al., "Carboxylic Acid Analogues of Tamoxifen: (Z)-2-[p-(1,2-Diphenyl-1-butenyl)phenoxy]-N,N-dimethylethylamine. Estrogen Receptor Affinity and Estrogen Antagonist Effects in MCF-7 Cells," *Journal of Medicinal Chemistry*, 42(16):3126-3133 (Aug. 1999).

Kumar, et al., "Localisation of the Oestradiol-binding and Putative DNA-binding Domains of the Human Oestrogen Receptor," *EMBO, J.*, 5(9):2231-2236 (1986).

Lee, et al., "Hormone-dependent Transactivation by Estrogen Receptor Chimeras That Do Not Interact with hsp90," *The Journal of Biological Chemistry*, 271(42):25727-25730 (Oct. 18, 1996).

Littlewood, et al., "A Modified Oestrogen Receptor Ligand-binding Domain as an Improved Switch for the Regulation of Heterologous Proteins," *Nucleic Acids Research*, 23(10):1686-1690 (1995).

Logie, et al., "Ligand-regulated Site-specifc Recombination," *Proc. Natl. Acad. Sci. USA*, 92:5940-5944 (Jun. 1995).

Mahfoudi, et al., "Specific Mutations in the Estrogen Receptor Change the Properties of Antiestrogens to Full Agonists," *Proc. Natl. Acad. Sci. USA*, 92:4206-4210 (May 1995).

McDonnell, et al., "Analysis of Estrogen Receptor Function In Vitro Reveals Three Distinct Classes of Antiestrogens," *Molecular Endocrinology*, 9(6):659-669 (1995).

Metzger, et al., "Conditional Site-specific Recombination in Mammalian Cells Using a Ligand-dependent Chimeric Cre Recombinase," *Proc. Natl. Acad. Sci. USA*, 92:6991-6995 (Jul. 1995).

Miller, et al., "Random Mutagenesis of Human Estrogen Receptor Ligand Binding Domain Identifies Mutations that Decrease Sensitivity to Estradiol and Increase Sensitivity to a Diphenol Indene-o1 Compound: Basis for a Regulatable Expression System," *J. Steroid Biochem. Molec. Biol.*, 64(3-4):129-135 (1998).

Montano, et al., "Human Estrogen Receptor Ligand Activity Inversion Mutants: Receptors that Interpret Antiestrogens as Estrogens and Estrogens as Antiestrogens and Discriminate Among Different Antiestrogens," *Molecular Endocrinology*, 19(3):230-242 (1996).

Nilsson, et al., "Mechanisms for Estrogen Action," *Physiological Reviews*, 81(4):1535-1565 (Oct. 2001).

No, et al., "Ecdysone-inducible Gene Expression in Mammalian Cells and Transgenic Mice," *Proc. Natl. Acad. Sci. USA*, 93:3346-3351 (Apr. 1996).

Peet, et al., "Engineering Novel Specifications for Ligand-activated Transcription in the Nuclear Hormone Receptor RXR," *Chemistry & Biology*, 5:13-21 (Jan. 14, 1998).

Roemer, et al., "Modulation of Cell Proliferation and Gene Expression by a p53-estrogen Receptor Hybrid Protein," *Proc. Natl. Acad. Sci. USA*, 90:9252-9256 (Oct. 1993).

Ruff, et al., "Estrogen Receptor Transcription and Transactivation Structure-function Relationship in DNA- and Ligand-binding Domains of Estrogen Receptors," *Breast Cancer Research*, 2:353-359 (Jul. 2000).

Sakhuja, et al., "Transcriptional Regulation of Gene Expression in a Gutless Adenoviral Vector Delivery System," *Molecular Therapy*, 5(5):abstract 75 (May 2002).

Sakhuja, et al., "Transcriptional Regulation of Gene Expression in a Gutless Adenoviral Vector Delivery System," Oral Presentation, *American Society of Gene Therapy 5th Annual Meeting*, Jun. 5-9, 2002 (presented Jun. 6, 2002).

Shiau, et al., "The Structural Basis of Estrogen Receptor/Coactivator Recognition and the Antagonism of This Interaction by Tamoxifen," *Cell*, 95:927-937 (Dec. 23, 1998).

Stafford, et al., "Mutations in the AF-2/Hormone-binding Domain of the Chimeric Activator GAL4-Estrogen Receptor VP16 Inhibit Hormone-dependent Transcriptional Activation and Chromatin Remodeling in Yeast," *The Journal of Biological Chemistry*, 273(51):342, 1998.

Superti-Furga, et al., "Hormone-dependent Transcriptional Regulation and Cellular Transformation by Fos-steroid Receptor Fusion Proteins," *Proc. Natl. Acad. Sci. USA*, 88:5114-5118 (Jun. 1991).

Tanenbaum, et al., "Crystallographic Comparison of the Estrogen and Progesterone Receptor's Ligand Binding Domains," *Proc. Natl. Acad. Sci. USA*, 95:5998-6003 (May 1998).

Tedesco, et al., "The Estrogen Receptor: A Structure-based Approach to the Design of New Specific Hormone-receptor Combinations," *Chemistry & Biology*, 8:277-287 (Feb. 2001).

Tora, et al., "The Cloned Human Eostrogen Receptor Contains a Mutation Which Alters its Hormone Binding Properties," *EMBO, J.*, 8(7):1981-1986 (1989).

Wang, et al., "A Regulatory System for Use in Gene Transfer," *Proc. Natl. Acad. Sci. USA*, 91:8180-8184 (Aug. 1994).

Whelan, et al., "Generation of Estrogen Receptor Mutants with Altered Ligand Specificity for Use in Establishing a Regulatable Gene Expression System," *J. Steroid Biochem. Molec. Biol.*, 58(1):3-12 (1996).

White, J., "Modified Steroid Receptors and Steroid-Inducible Promoters as Genetic Switches for Gene Therapy," *Advances in Pharmacology*, 40:339-367 (1997).

Wrenn, et al., "Structure-function Analysis of the Hormone Binding Domain of the Human Estrogen Receptor by Region-specific Mutagenesis and Phenotypic Screening in Yeast," *The Journal of Biological Chemistry*, 268(32):24089-24098 (Nov. 15, 1993).

Wurtz, et al., "Three-Dimensional Models of Estrogen Receptor Ligand Binding Domain Complexes, Based on Related Crystal Structures and Mutational and Structure—Activity Relationship Data," *J. Med. Chem.*, 41:1803-1814 (1998).

Xu, et al., "A Versatile Framework for the Design of Ligand-Dependent, Transgene-Specific Transcription Factors," *Molecular Therapy*, 3(2):262-273 (Feb. 2001).

Zerby, et al., "Regulation of Gene Expression in an Adenoviral Vector Delivery System," *Molecular Therapy*, 3(5): No. 72 (May 2001).

Zerby, et al., "Regulation of Gene Expression in an Adenoviral Vector Delivery System," Oral Presentation presented May 31, 2001 at *The Fourth Annual Meeting of the American Society of Gene Therapy* (May 30-Jun. 3, 2001; Seattle, Washington).

* cited by examiner

Figure 6

Fold Induction at 10 nM

| Region I | | | Region II | | |
|---|---|---|---|---|---|
| 388V/424Y/428A | | | H524G | | |
| LBB938 | 4-OHTAM | E₂ | LBF580 | 4-OHTAM | E₂ |
| 200 | 20 | 3 | 140 | 327 | 16 |
| 421V/428A | | | | | |
| LBB551 | 4-OHTAM | E₂ | | | |
| 247 | 414 | 103 | | | |

Figure 13

Gutless Adenoviral Vectors

| Ligand | Vector |
|---|---|
| Tamoxifen | ITR – CMV – 521 Transcription Factor – ITR |
| LBB938 | ITR – CMV – 388V-424Y-428A TF – ITR |
| LBG551 | ITR – CMV – 421V-428A TF – ITR |
| LBF580 | ITR – CMV – 524-G TF – ITR |
|  | ITR – 6X RE – Endostatin – ITR |

NUCLEIC ACIDS ENCODING ESTROGEN RECEPTOR LIGAND BINDING DOMAIN VARIANTS

This application claims the benefit of U.S. Provisional Application No. 60/294,839, filed May 31, 2001, incorporated herein by reference in its entirety.

FIELD OF THE INVENTION

The present invention relates generally to the fields of molecular endocrinology and receptor pharmacology. More specifically, the present invention relates to novel variations of the estrogen receptor and to compounds that selectively bind and activate or block these receptors. It further relates to molecular switches for gene therapy.

BACKGROUND OF THE INVENTION

The ability to regulate gene expression in vivo in transgenic animals, including humans, is of vital importance both to the investigation of gene function and to the control and utility of therapeutic gene expression in gene therapy in animals or humans.

A variety of approaches have been attempted to develop a reliable system for controlling gene expression in vivo. The first attempts were based on the use of promoters that could be induced by endogenous transcription factors in response to a controllable stimulus such as heat shock (Wurm F. M., Gwinn K. A. and Kingston R. E., "Inducible overproduction of the mouse c-myc protein in mammalian cells" *Proc. Natl. Acad. Sci. USA* 83: 5414-5418 (1986)) or heavy metal ions (Mayo K. E., Warren R. and Palmiter R. D., "The mouse metallothionein-1 gene is transcriptionally regulated by cadmium following transfection into human or mouse cells" *Cell* 29: 99-108 (1982)). However, it was found that induction ratios were low and the induction agent itself often activated a large number of unwanted endogenous genes.

To overcome these problems, attempts were made to develop inducible systems which use chimeric transcription factors that combine elements from mammalian, bacterial, yeast and viral transcription factors (for review, see Gossen M., Bonin A. L. and Bujard H., "Control of gene activity in higher eukaryotic cells by prokaryotic regulatory elements" *Trends in Biochem. Sci.* 18: 471-475 (1993)).

One example of the use of these systems is the use of the lac repressor, which can then be induced by isopropyl D-thiogalactopyranoside (IPTG) (Baim S. B., Labow M. A., Levine A. J. and Shenk T., "A chimeric mammalian transactivator based on the lac repressor that is regulated by temperature and isopropyl D-thiogalactopyranoside" *Proc. Natl. Acad. Sci. U.S.A.* 88: 5072-5076 (1991)). This system is seriously limited by the toxicity of IPTG in animals.

In an alternative system, the DNA binding domain of the tetracycline (tet) repressor from *E. coli* is combined with the activating domain of the herpes simplex virus protein VP16 (Gossen M. and Bujard H., "Tight control of gene expression in mammalian cells by tetracycline-responsive promoters" *Proc. Natl. Acad. Sci. U.S.A.* 89: 5547-5551 (1992)). The gene of interest is placed downstream of the multiple tet operator sequences. In the absence of tetracycline, the tet/VP 16 activator will bind the operator sequence and activate the downstream gene. In the presence of tetracycline, the gene of interest will not be transcribed because the binding of the tet/VP16 activator will be inhibited. This system has been shown to have the ability to control reporter gene expression in vivo in transgenic mice (Furth, P. A., St. Onge L., Boger H., Gruss P., Gossen M., Kistner A., Bujard H. and Hennighausen L., "Temporal control of gene expression in transgenic mice by a tetracycline-responsive promoter" *Proc. Natl. Acad. Sci. U.S.A.* 91: 9302-9306 (1994)). However, this system and its variants suffer from the serious disadvantage that tetracycline is used as the repressor and must always be present to keep the downstream gene of interest silent. In addition, the bacterial protein components may be immunogenic in humans.

The disadvantages of the systems described above have provided incentives for an entirely different approach to the control of therapeutic gene expression in, for example, gene therapy. This approach creates an inducible gene control system by fusing the hormone binding domain (HBD) or ligand binding domain (LBD) of a steroid hormone receptor with certain proteins (Wang Y., O'Malley B. W., Jr., Tsai S. Y. and O'Malley B. W., "A regulatory system for use in gene transfer" *Proc. Natl. Acad. Sci.* 91: 8180-8184 (1994)). In such a fusion product, a number of proteins will be inactive in the absence of hormone but resume normal activity in the presence of the hormone or hormone variant which binds at this domain.

The proteins used in such a system may have a wide variety of thus controllable activities. For example, these proteins may be regulator proteins specific for the control of the transcription of particular transgene. Many control systems of this type have been constructed using the HBD of the estrogen receptor (ER) (Hollenberg S. M., Cheng P. F. and Weintraub H., "Use of conditional MyoD transcription factor studies of MyoD transactivation and muscle determination" *Proc. Natl. Acad. Sci. U.S.A.* 90: 8028-8032 (1993); Braselmann S., Graninger P. and Busslinger M., "A selective transcriptional induction system for mammalian cells based on GAL4-estrogen receptor fusion proteins" *Proc. Natl. Acad. Sci.* 90: 1657-1661 (1993); Roemer K. and Friedmann T., "Modulation of cell proliferation and gene expression by a p53-estrogen receptor hybrid protein" *Proc. Natl. Acad. Sci. USA* 90: 9252-9256 (1993); Superti-Furga G., Bergers G., Picard D. and Busslinger M., "Hormone-dependent transcriptional regulation and cellular transformation by Fos-steroid receptor fusion proteins" *Proc. Natl. Acad. Sci. U.S.A.* 88: 5114-5118 (1991)). The ligand of the ER, 17β-estradiol is readily available, relatively cheap and many cell types lack an endogenous estrogen receptor. However, these systems employing the HBD of the wildtype estrogen receptor are potentially disadvantageous in that use of the hormone to control the inducible system will also activate endogenous steroid hormone receptors and thereby alter the activity of endogenous genes. Furthermore, the systems will be influenced by levels of endogenous β-estradiol.

One approach to regulating transgene expression and avoiding the activation of endogenous and unwanted genes has been the modification and use of chimeric nuclear hormone receptors, such as a steroid hormone receptor. Steroid hormone receptors are responsible for the regulation of complex cellular events, including transcription. The ovarian hormones, estrogen and progesterone, are responsible, in part, for the regulation of the complex cellular events associated with differentiation, growth and functioning of female reproductive tissues. These hormones also play important roles in development and progression of malignancies of the reproductive endocrine system.

The biological activity of steroid hormones is mediated directly by a hormone and tissue-specific intracellular receptor. The physiologically inactive form of the steroid receptor may exist as an oligomeric complex with proteins, such as heat-shock protein (hsp) 90, hsp70 and hsp56. Upon binding its specific ligand, the receptor changes conformation and dissociates from the inhibitory heteroligomeric complex. Subsequent dimerization allows the receptor to bind to specific DNA sites in the regulatory region of target gene promoters. Following binding of the receptor to DNA, the hormone is responsible for mediating a second function that allows the receptor to interact specifically with the transcription apparatus. Displacement of additional inhibitory proteins and DNA-dependent phosphorylation may constitute the final steps in this activation pathway.

Cloning of several members of the steroid receptor superfamily has facilitated the reconstitution of hormone-dependent transcription in heterologous cell systems. Subsequently, in vivo and in vitro studies with mutant and chimeric receptors have demonstrated that steroid hormone receptors are modular proteins organized into structurally and functionally defined domains. A well-defined 66-68 amino acid DNA binding domain (DBD) has been identified and studied in detail, using both genetic and biochemical approaches. The ligand (hormone) binding domain (LBD), located in the carboxyl-terminal half of the receptor, consists of about 300 amino acids. Thus, these nuclear receptors, such as the estrogen receptor (ER), are ligand-activated transcription factors that include a DNA binding domain (DBD) and a hormone binding domain (HBD) also known as a ligand binding domain (LBD). The LBD also contains sequences responsible for receptor dimerization, hsp interactions and one of the two transactivation sequences of the receptor. See, for example, Nilsson et al., "Mechanisms of Estrogen Action" *Physiol. Rev.* 81(4): 1535-1565 (2001), incorporated herein by reference.

In order to make a system utilizing these elements as adaptable and useful as possible, these chimeric regulator proteins are preferably altered in their DNA binding specificity, to make them specific for control of the desired transgene (see WO 01/30843A1, which is incorporated by reference herein for all purposes) and they are preferably altered in their ligand binding specificity so they will respond to a ligand that will not cause altered activity of other endogenous genes.

For example, a preferred pharmacological profile for the LBD of the chimeric regulator would include the following features:
1) Physiologic levels of endogenous hormones normally found in man do not activate the receptor;
2) The receptor could be activated by a custom designed, synthetic compound at levels (doses) that can be achieved in vivo without toxicity; and
3) At the required dose for transgene regulation, the synthetic compound is inactive, i.e., is neither an agonist nor antagonist, on the naturally occurring endogenous hormone receptors.

Gene replacement therapy requires the ability to control the level of expression of transfected genes from outside the body. Such a "molecular switch" preferably includes the properties of: specificity, selectivity, precision, safety and rapid clearance. The steroid receptor family of gene regulatory proteins is an ideal set of such molecules. These proteins are ligand activated transcription factors whose ligands can range from steroids to retinoids, fatty acids, vitamins, thyroid hormones and other specifically engineered small molecules. These compounds bind to receptors and either up-regulate or down-regulate. The compounds are cleared from the body by existing mechanisms and the compounds are non-toxic.

The efficacy of a ligand is a consequence of its interaction with the receptor. This interaction can involve contacts causing the receptor to become active (agonist) or for the receptor to be inactive (antagonist). The affinity of antagonist activated receptors for DNA is similar to that of agonist-bound receptor. Nevertheless, in the presence of the antagonist, the receptor cannot activate transcription efficiently. Thus, both up and down regulation are possible by this pathway.

Modified steroid hormone receptors have been developed for use for regulated expression of transgenes (see, e.g., U.S. Pat. Nos. 5,874,534 and No. 5,935,934 and PCT publication No. WO 98/18925, which claims priority to U.S. Provisional Application No. 60/029,964) by modifying the ligand specificity of the LBD. In addition, the DNA binding domain of the receptor has been replaced with a non-mammalian DNA binding domain selected from yeast GAL4 DBD, a viral DBD and an insect DBD binding domain to provide for regulated expression of a co-administered gene containing a region recognized by the non-mammalian DBD. These constructs, however, have several potential drawbacks and generally lack flexibility. The non-mammalian DBD is potentially immunogenic and the array of sequences recognized by these DBD's is limited, accordingly limiting gene targets. Therefore, there remains a need for versatile and effective gene regulators.

SUMMARY OF THE INVENTION

In this invention the construction of novel modified steroid hormone receptors which can regulate the expression of nucleic acid sequences is described. These constructs allow control of the transactivation function of the modified steroid hormone receptor. These modified constructs unexpectedly allow the mutant receptors to bind various ligands whose structures differ substantially from the naturally occurring ligands for these receptors. Provided also in this invention are synthetic ligands that are tamoxifen derivatives. However these synthetic ligands lack significant agonist or antagonistic action at the wild-type human estrogen receptor alpha. This property permits the construction of "molecular switches" which can be formulated to respond to these and other ligands which are synthetic and sufficiently different in structure from the naturally occurring ligands, e.g. the naturally occurring hormone estrogen, so that the switches can be used even in the presence of physiological concentrations of the naturally occurring ligand without problematic interference. These modified switches thereby provide a substantial improvement over prior attempts to control or regulate target genes.

Thus, there is provided in accordance with one aspect of the present invention a modified steroid hormone receptor protein. This modified steroid hormone receptor protein is capable of specific binding to various synthetic ligands.

In a preferred embodiment, the present invention provides a modified estrogen receptor alpha ligand binding domain comprising at least one amino acid modification in Region 1, at least one amino acid modification in Region 2, or at least one amino acid modification in each of both Regions 1 and 2, wherein said ligand binding domain interacts with a non-endogenous ligand as a result of said at least one amino acid modification. Preferably, the modified estrogen receptor alpha ligand binding domain is a modified human estrogen receptor alpha ligand binding domain.

According to one preferred embodiment, the at least one amino acid modification occurs at a position corresponding to one or more of positions 388, 391, 421, 424, and 428 of SEQ ID NO:55.

In a preferred embodiment, the methionine at the position corresponding to position 388 of SEQ ID NO:55 is replaced with another amino acid. In another preferred embodiment, the methionine at the position corresponding to position 388 of SEQ ID NO:55 is replaced with alanine. In another preferred embodiment, the methionine at the position corresponding to position 388 of SEQ ID NO:55 is replaced with phenylalanine. In another preferred embodiment, the methionine at the position corresponding to position 388 of SEQ ID NO:55 is replaced with valine. In another preferred embodiment, the methionine at the position corresponding to position 388 of SEQ ID NO:55 is replaced with tryptophan.

In a preferred embodiment, the leucine at the position corresponding to position 391 of SEQ ID NO:55 is replaced with another amino acid.

In a preferred embodiment, the methionine at the position corresponding to position 421 of SEQ ID NO:55 is replaced with another amino acid. In another preferred embodiment, the methionine at the position corresponding to position 421 of SEQ ID NO:55 is replaced with valine.

In a preferred embodiment, the isoleucine at the position corresponding to position 424 of SEQ ID NO:55 is replaced with another amino acid. In another preferred embodiment, the isoleucine at the position corresponding to position 424 of SEQ ID NO:55 is replaced with alanine. In another preferred embodiment, the isoleucine at the position corresponding to position 424 of SEQ ID NO:55 is replaced with methionine. In another preferred embodiment, the isoleucine at the position corresponding to position 424 of SEQ ID NO:55 is replaced with phenylalanine. In another preferred embodiment, the isoleucine at the position corresponding to position 424 of SEQ ID NO:55 is replaced with leucine. In another preferred embodiment, the isoleucine at the position corresponding to position 424 of SEQ ID NO:55 is replaced with valine. In another preferred embodiment, the isoleucine at the position corresponding to position 424 of SEQ ID NO:55 is replaced with tyrosine.

In a preferred embodiment, the leucine at the position corresponding to position 428 of SEQ ID NO:55 is replaced with another amino acid. In another preferred embodiment, the leucine at the position corresponding to position 428 of SEQ ID NO:55 is replaced with alanine. In another preferred embodiment, the leucine at the position corresponding to position 428 of SEQ ID NO:55 is replaced with valine.

In a particularly preferred embodiment, the methionine at the position corresponding to position 388 of SEQ ID NO:55 is replaced with another amino acid, the isoleucine at the position corresponding to position 424 of SEQ ID NO:55 is replaced with another amino acid, and the leucine at the position corresponding to position 428 of SEQ ID NO:55 is replaced with another amino acid. In an especially preferred embodiment, the methionine at the position corresponding to position 388 of SEQ ID NO:55 is replaced with valine, the isoleucine at the position corresponding to position 424 of SEQ ID NO:55 is replaced with tyrosine, and the leucine at the position corresponding to position 428 of SEQ ID NO:55 is replaced with alanine.

In a particularly preferred embodiment, the methionine at the position corresponding to position 421 of SEQ ID NO:55 is replaced with another amino acid, and the leucine at the position corresponding to position 428 of SEQ ID NO:55 is replaced with another amino acid. In an especially preferred embodiment, the methionine at the position corresponding to position 421 of SEQ ID NO:55 is replaced with valine, and the leucine at the position corresponding to position 428 of SEQ ID NO:55 is replaced with alanine.

According to another preferred embodiment, the least one amino acid modification occurs at a position corresponding to one or more of positions 521 and 524 of SEQ ID NO:55.

In a preferred embodiment, the glycine at the position corresponding to position 521 of SEQ ID NO:55 is replaced with another amino acid. In another preferred embodiment, the glycine at the position corresponding to position 521 of SEQ ID NO:55 is replaced with arginine.

In a particularly preferred embodiment, the histidine at the position corresponding to position 524 of SEQ ID NO:55 is replaced with another amino acid. In an especially preferred embodiment, the histidine at the position corresponding to position 524 of SEQ ID NO:55 is replaced with glycine. In another preferred embodiment, the histidine at the position corresponding to position 524 of SEQ ID NO:55 is replaced with alanine.

In accordance with another aspect of the present invention, there is provided a fusion receptor protein comprising a nucleic acid binding domain operatively linked to a modified estrogen receptor alpha ligand binding domain of the invention. In a preferred embodiment, the nucleic acid binding domain is a C2H2 binding domain, a GAL4 DNA binding domain, a virus DNA binding domain, an insect DNA binding domain, or a non-mammalian DNA binding domain. In an especially preferred embodiment, the nucleic acid binding domain is comprised of modular units from a Cys2/His2 zinc finger peptide.

In accordance with another aspect of the present invention, there is provided a fusion receptor protein comprising a nucleic acid binding domain operatively linked to a modified estrogen receptor alpha ligand binding domain of the invention, and further comprising a transactivation domain. In a preferred embodiment, the transactivation domain is selected from the group consisting of VP16, TAF-1, TAF-2, TAU-1, TAU-2 and p65 and the activation domains from members of the STAT family, including but not limited to STAT-6.

In accordance with another aspect of the present invention, there is provided an isolated nucleic acid molecule comprising a nucleotide sequence encoding a modified estrogen receptor alpha ligand binding domain of the invention.

In accordance with another aspect of the present invention, there is provided an isolated nucleic acid molecule comprising a nucleotide sequence encoding a fusion receptor protein of the invention.

In accordance with another aspect of the present invention, there is provided a chimeric construct comprising a promoter operatively linked to a nucleic acid molecule of the invention.

In accordance with another aspect of the present invention, there is provided a plasmid containing a chimeric construct of the invention.

In accordance with another aspect of the present invention, there is provided a cell containing a chimeric construct of the invention.

In accordance with another aspect of the present invention, there is provided a molecular switch for regulating expression of a promoter transcriptionally linked to a nucleic acid sequence of interest, comprising: (a) a fusion receptor protein of the invention, wherein the nucleic acid binding domain of said fusion receptor protein binds said promoter, and wherein the transactivation domain of said fusion receptor protein causes transcription from the promoter when said fusion receptor protein is bound to the promoter; and (b) a ligand that preferentially binds to the modified estrogen receptor alpha ligand binding domain of said fusion receptor protein, wherein binding activates the transcription domain to cause transcription of the nucleic acid sequence of interest.

In a preferred embodiment, the modified estrogen receptor alpha ligand binding domain is activated by the ligand at a concentration whereby the ligand is substantially inactive on wild-type estrogen receptor alpha. In a more preferred embodiment, the ligand is a tamoxifen derivative. In a particularly preferred embodiment, the modified estrogen receptor alpha ligand binding domain of the fusion receptor protein binds a compound selected from the group consisting of: 1) LBB938 4-((1Z))-3-bicyclo[hept-2-yl-1-{4-[2-(dimethylamino)ethoxy]phenyl}-2-phenylprop-1-enyl)phenol; 2) LBB551 carbamic acid, [(2Z)-3-[4-[2-(dimethylamino)ethoxy]phenyl]-3-(4-hydroxyphenyl)-2-phenyl-2-propenyl]-, methyl ester; 3) LBC081 carbamic acid, [(2E)-3-[4-[2-(dimethylamino)ethoxy]phenyl]-3-(4-hydroxyphenyl)-2-phenyl-2-propenyl]-, methyl ester; 4) LBF580 4-((l E)-1 - {4-[2-(dimethylamino)ethoxy]phenyl}-2-(4-morpholin-4-ylphenyl)prop-1 -enyl)phenol; and non-hydroxylated forms thereof.

In an especially preferred embodiment, the modified estrogen receptor alpha ligand binding domain of the fusion receptor protein comprises the following amino acid substitutions in Region 1: the methionine at the position corresponding to position 388 of SEQ ID NO:55 is replaced with valine, the isoleucine at the position corresponding to position 424 of SEQ ID NO:55 is replaced with tyrosine, and the leucine at the position corresponding to position 428 of SEQ ID NO:55 is replaced with alanine; and wherein the ligand is LBB938 4-((1Z))-3-bicyclo[hept-2-yl-1-{4-[2-(dimethylamino)ethoxy]phenyl}-2-phenylprop-1-enyl)phenol.

In another especially preferred embodiment, the modified estrogen receptor alpha ligand binding domain of the fusion receptor protein comprises the following amino acid substitutions in Region 1: the methionine at the position corresponding to position 421 of SEQ ID NO:55 is replaced with valine, and the leucine at the position corresponding to position 428 of SEQ ID NO:55 is replaced with alanine; and wherein the ligand is LBB551 carbamic acid, [(2Z)-3-[4-[2-(dimethylamino)ethoxy]phenyl]-3-(4-hydroxyphenyl)-2-phenyl-2-propenyl]-, methyl ester, or LBC081 carbamic acid, [(2E)-3-[4-[2-(dimethylamino)ethoxy]phenyl]-3-(4-hydroxyphenyl)-2-phenyl-2-propenyl]-, methyl ester.

In another especially preferred embodiment, the modified estrogen receptor alpha ligand binding domain of the fusion receptor protein comprises the following amino acid substitution in Region 2: the histidine at the position corresponding to position 524 of SEQ ID NO:55 is replaced with glycine; and wherein the ligand is LBF580 4-((1E)-1-{4-[2-(dimethylamino)ethoxy]phenyl}-2-(4-morpholin-4-ylphenyl)prop-1 -enyl)phenol.

In accordance with another aspect of the present invention, there is provided a method of activating expression of a nucleic acid sequence of interest, comprising: (a) transforming a cell with a chimeric construct of the invention and a target expression cassette comprising the nucleic acid sequence of interest; (b) expressing the fusion receptor protein in said transformed cell; and (c) contacting said transformed cell with a ligand that preferentially binds to the modified estrogen receptor alpha ligand binding domain of the fusion receptor protein, wherein binding activates the transcription domain of the fusion receptor protein to thereby activate expression of the nucleic acid sequence of interest.

In a preferred embodiment of the method of the invention, the modified estrogen receptor alpha ligand binding domain is activated by the ligand at a concentration whereby the ligand is substantially inactive on wild-type estrogen receptor alpha. In a more preferred embodiment, the ligand is a tamoxifen derivative. In a particularly preferred embodiment, the modified estrogen receptor alpha ligand binding domain of the fusion receptor protein binds a compound selected from the group consisting of: 1) LBB938 4-((1Z))-3-bicyclo[hept-2-yl-1-{4-[2-(dimethylamino)ethoxy]phenyl}-2-phenylprop-1-enyl)phenol; 2) LBB551 carbamic acid, [(2Z)-3-[4-[2-(dimethylamino)ethoxy]phenyl]-3-(4-hydroxyphenyl)-2-phenyl-2-propenyl]-, methyl ester; 3) LBC081 carbamic acid, [(2E)-3-[4-[2-(dimethylamino)ethoxy]phenyl]-3-(4-hydroxyphenyl)-2-phenyl-2-propenyl]-, methyl ester; 4) LBF580 4-((1E)-1-{4-[2-(dimethylamino)ethoxy]phenyl}-2-(4-morpholin-4-ylphenyl)prop-1-enyl)phenol; and non-hydroxylated forms thereof.

In an especially preferred embodiment of the method of the invention, the modified estrogen receptor alpha ligand binding domain of the fusion receptor protein comprises the following amino acid substitutions in Region 1: the methionine at the position corresponding to position 388 of SEQ ID NO:55 is replaced with valine, the isoleucine at the position corresponding to position 424 of SEQ ID NO:55 is replaced with tyrosine, and the leucine at the position corresponding to position 428 of SEQ ID NO:55 is replaced with alanine; and wherein the ligand is LBB938 4-((1Z))-3-bicyclo[hept-2-yl-1-{4-[2-(dimethylamino)ethoxy]phenyl}-2-phenylprop-1 -enyl)phenol.

In another especially preferred embodiment of the method of the invention, the modified estrogen receptor alpha ligand binding domain of the fusion receptor protein comprises the following amino acid substitutions in Region 1: the methionine at the position corresponding to position 421 of SEQ ID NO:55 is replaced with valine, and the leucine at the position corresponding to position 428 of SEQ ID NO:55 is replaced with alanine; and wherein the ligand is LBB551 carbamic acid, [(2Z)-3-[4-[2-(dimethylamino)ethoxy]phenyl]-3-(4-hydroxyphenyl)-2-phenyl-2-propenyl]-, methyl ester, or LBC081 carbamic acid, [(2E)-3-[4-[2-(dimethylamino)ethoxy]phenyl]-3-(4-hydroxyphenyl)-2-phenyl2-propenyl]-, methyl ester.

In another especially preferred embodiment of the method of the invention, the modified estrogen receptor alpha ligand binding domain of the fusion receptor protein comprises the following amino acid substitution in Region 2: the histidine at the position corresponding to position 524 of SEQ ID NO:55 is replaced with glycine; and wherein the ligand is LBF580 4-((1E)-1-{4-[2-(dimethylamino)ethoxy]phenyl}-2-(4-morpholin-4-ylphenyl)prop-1 -enyl)phenol.

In a preferred embodiment of the method of the invention, the transformed cell is in a human or animal, and contacting the transformed cell with a ligand comprises administering a pharmacological dose of the ligand to the human or animal.

In a preferred embodiment of the method of the invention, the chimeric construct and the target expression cassette are on separate DNA molecules and are co-transformed into the cell.

In accordance with another aspect of the present invention, there is provided the compound LBB938 which is 4-((1Z))-3-bicyclo[hept-2-yl-1-{4-[2-(dimethylamino) ethoxy]phenyl}-2-phenylprop-1 -enyl)phenol.

In accordance with another aspect of the present invention, there is provided a pharmaceutical composition which comprises an effective amount of compound LBB938 which is 4-((1Z))-3-bicyclo[hept-2-yl -1-{4-[2-(dimethylamino) ethoxy]phenyl}-2-phenylprop-1 -enyl)phenol, or a pharmaceutically acceptable salt thereof, together with one or more pharmaceutical carrier (s), diluent (s) and/or additives.

In accordance with another aspect of the present invention, there is provided the compound LBF580 4-((1E)-1-{4-[2-(dimethylamino)ethoxy]phenyl}-2-(4-morpholin-4-ylphenyl)prop-1-enyl)phenol, the structure of which is In accordance with another aspect of the present invention, there is provided a pharmaceutical composition which comprises an effective amount of LBF580 4-((1E)-1-{4-[2-(dimethylamino)ethoxy]phenyl}-2-(4-morpholin-4- ylphenyl)prop-1-enyl)phenol, or a pharmaceutically acceptable salt thereof, together with one or more pharmaceutical carrier (s), diluent (s) and/or additives.

In accordance with another aspect of the present invention, there is provided the compound LBB551, carbamic acid, [(2Z)-3-[4-[2-(dimethylamino)ethoxy]phenyl]-3-(4-hydroxyphenyl)-2-phenyl-2-propenyl]-, methyl ester.

In accordance with another aspect of the present invention, there is provided a pharmaceutical composition which comprises an effective amount of compound LBB55 1, carbamic acid, [(2Z)-3-[4-[2-(dimethylamino)ethoxy]phenyl]-3-(4-hydroxyphenyl)-2-phenyl-2-propenyl]-, methyl ester, or a pharmaceutically acceptable salt thereof, together with one or more pharmaceutical carrier (s), diluent (s) and/or additives.

In accordance with another aspect of the present invention, there is provided the compound LBC081, carbamic acid, [(2E)-3-[4-[2-(dimethylamino)ethoxy]phenyl]-3-(4-hydroxyphenyl)-2-phenyl-2-propenyl]-, methyl ester.

In accordance with another aspect of the present invention, there is provided a pharmaceutical composition which comprises an effective amount of compound LBC081, carbamic acid, [(2E)-3-[4-[2-(dimethylamino)ethoxy]phenyl]-3-(4-hydroxyphenyl)-2-phenyl-2-propenyl]-, methyl ester, or a pharmaceutically acceptable salt thereof, together with one or more pharmaceutical carrier (s), diluent (s) and/or additives.

A molecular switch of the invention may be used for regulating expression of a nucleic acid sequence in gene therapy in humans and animals. It is also useful as a molecular switch in plants and in transgenic animals. In preferred embodiments of the molecular switch, the native DNA binding domain in unmodified form is used and the ligand binding domain is modified to only bind a compound selected from the group consisting of non-natural ligands, synthetic ligands and non-native ligands.

Additional embodiments of the present invention include a method for regulating the expression of a nucleic acid cassette in gene therapy. The method includes the step of attaching the molecular switch to a nucleic acid cassette used in gene therapy. A sufficient dose of the nucleic acid cassette with the attached molecular switch can then be introduced into an animal or human to be treated. The molecular switch can then be up regulated or down regulated by dosing the animal or human with a ligand, which binds the modified binding site.

Other and further features and advantages will be apparent from the following description of the presently preferred embodiments of the invention which are given for the purposes of disclosure when taken in conjunction with the accompanying drawings.

BRIEF DESCRIPTION OF THE DRAWINGS

In the drawings, which form a portion of the specification:

FIG. 13 shows a schematic diagram of the gutless adenoviral vectors encoding either the novel transcription factors (TF) or the regulatable endostatin transgene. The novel cognate ligands are also displayed for each TF vector.

DETAILED DESCRIPTION OF THE INVENTION

This invention provides novel mutant estrogen receptor ligand binding domains (LBDs) and corresponding non-natural small molecule ligands. These mutant ER-LBD-ligand pairs fullfill many of the criteria for an ideal molecular-switch regulating system. These combinations of ER-LBD and small molecule ligand were made by structure based modifications in both the ER-LBD and the ligand. The approach was related to the "bumps and holes" strategy used to alter the specificity of small molecule-protein interaction in several systems including ER (See Belshaw and Schreiber, *J. Am. Chem.* Soc. 119:1805-1806, 1997 and Tedesco et. Al. *Chem & Biol.* 8:277-287, 2001). The results as demonstrated by the embodiments of the present invention demonstrate that the combination of rational design and regional mutagenesis is an efficient approach to identify novel and functional receptor targets for small molecule ligands.

Figure 1:
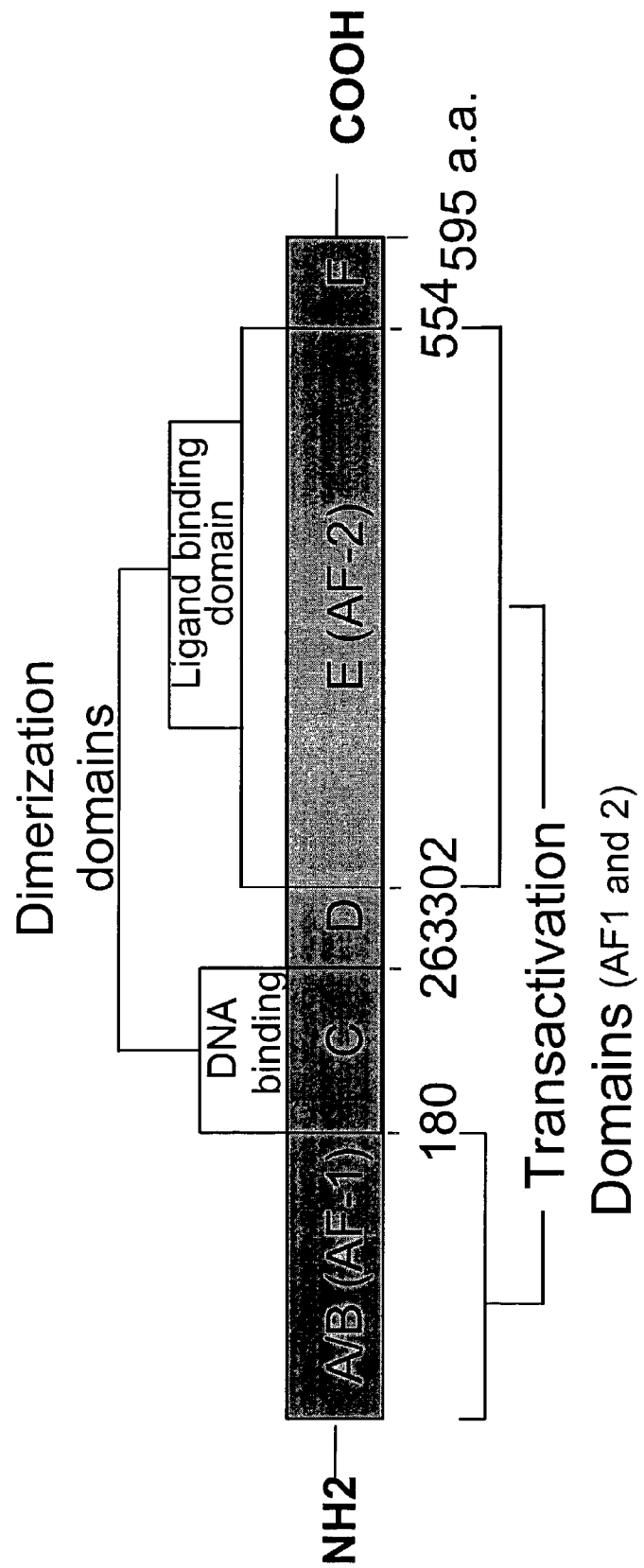
FIG. 1 is a schematic depiction of the functional domains (A-F) of the human estrogen receptor (ER) taken from FIG. 3 in White, John H. "Modified Steroid Receptors and Steroid-Inducible Promoters as Genetic Switches for Gene Therapy" *Advances in Pharmacology, Volume* 40, Academic Press (1997), incorporated herein by reference.
Figure 2:
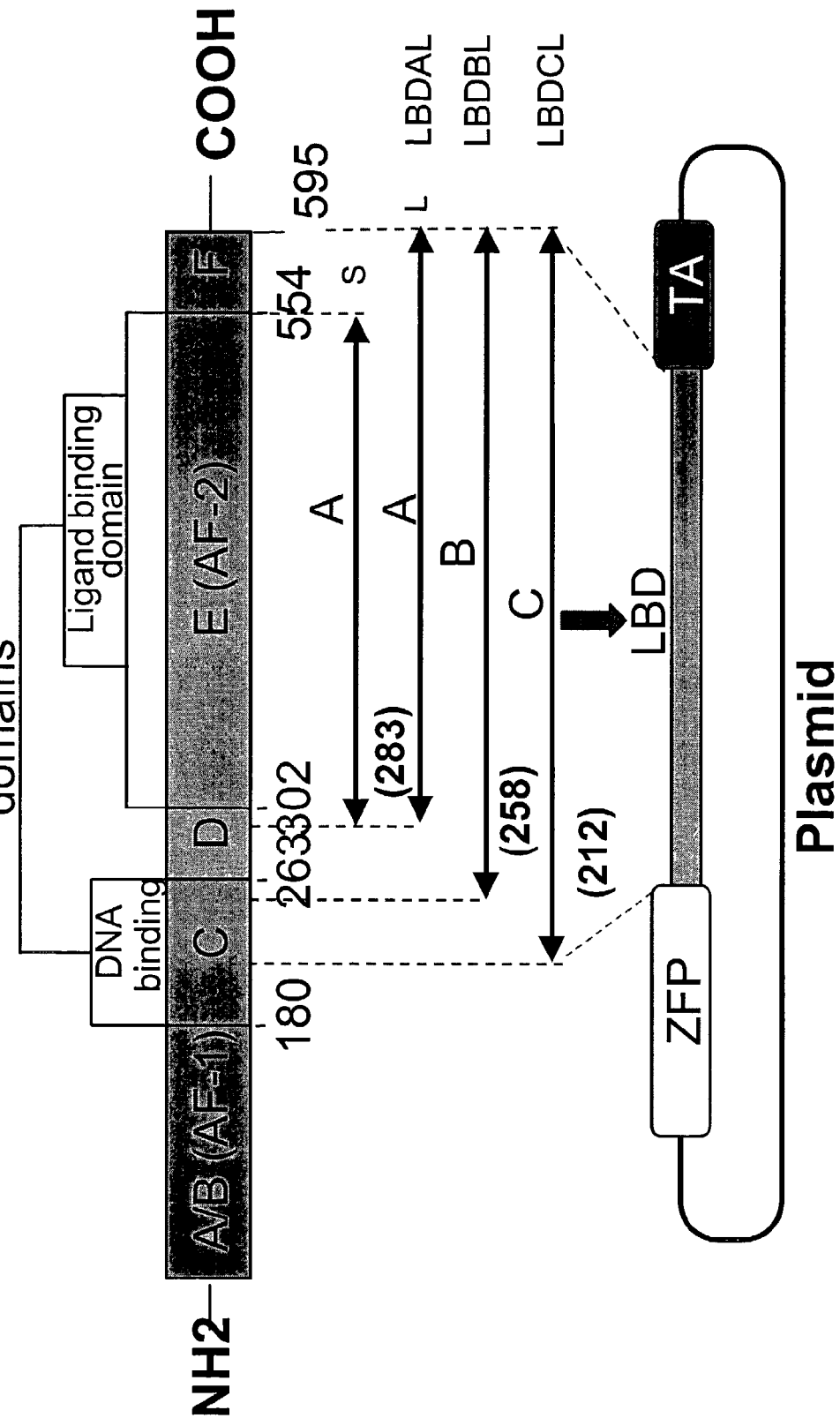
FIG. 2 is a schematic depiction of the cloning strategy for the construction of the recombinant molecular constructs, whereby the DNA binding domain is replaced.
Figure 3:
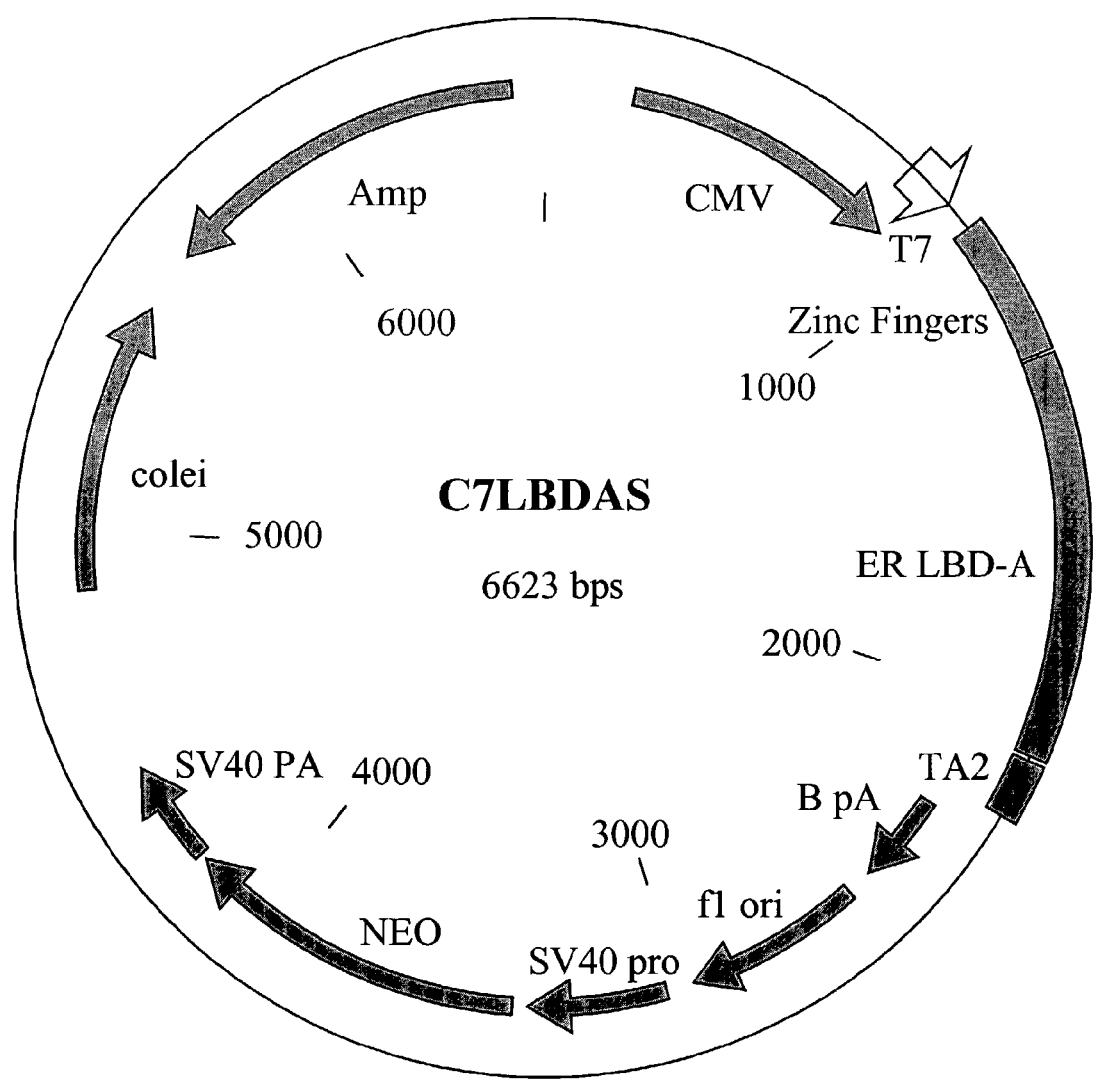
FIG. 3 is a schematic map of the expression vector for C7LBDAS based on the plasmid pCDNA3.1 (SEQ ID NO:1) nucleotide sequence, (SEQ ID NO:2) amino acid sequence.
Figure 4:
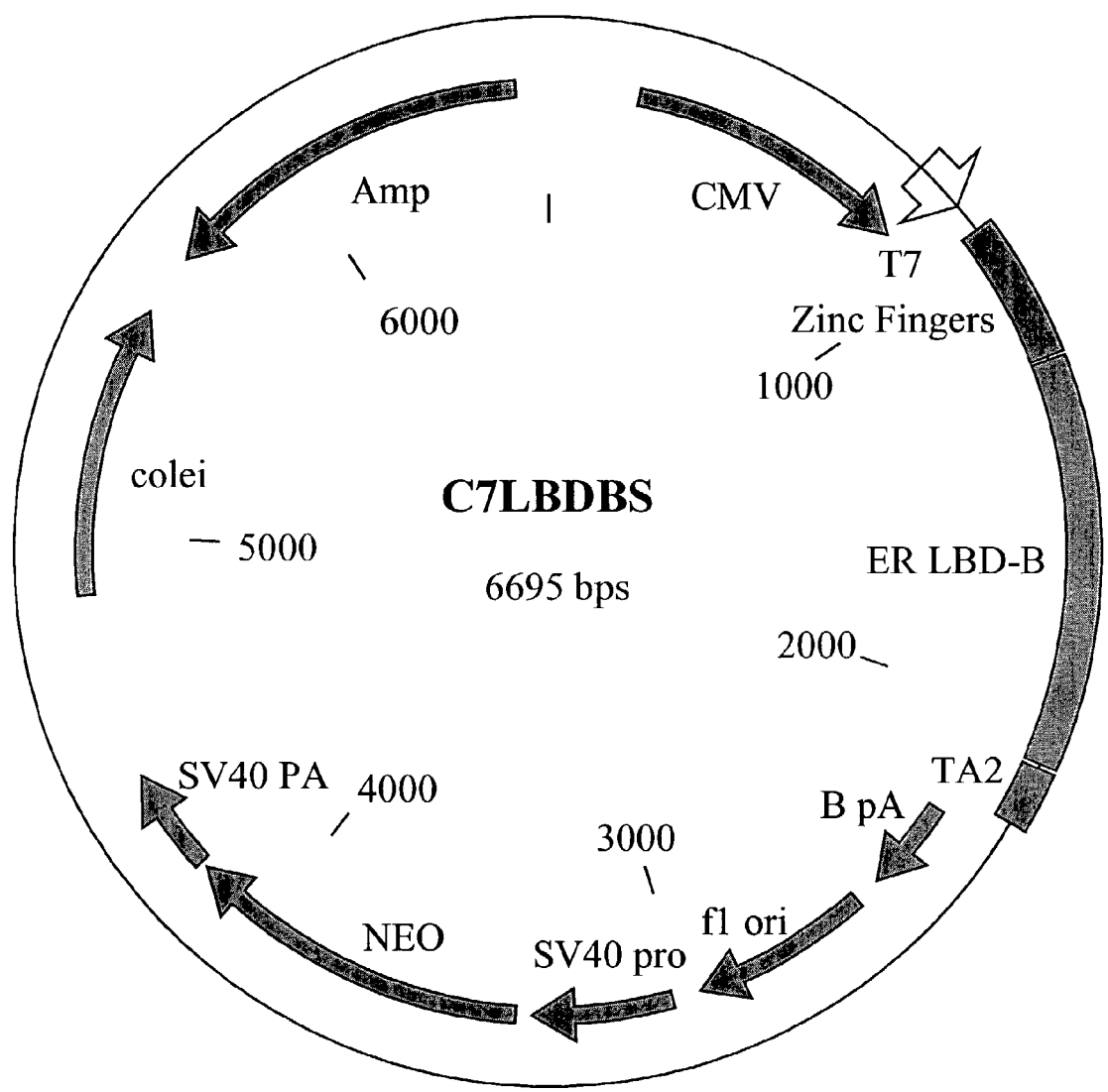
FIG. 4 is a schematic map of the expression vector for C7LBDBS based on the plasmid pCDNA3.1. (SEQ ID NO 3) nucleotide sequence, (SEQ ID NO:4) amino acid sequence.

The polypeptides of the present invention are constructed by producing selective amino acid substitutions in the estrogen receptor ligand binding domain (ER-LBD). Three fragments of the human estrogen receptor ligand binding domain (LBD) were used. These were fragments A, B, and C (with reference to FIG. 2) with or without the F region. LBD fragments without the F region are referred to herein as short forms and LBD fragments with the F region are referred to herein as long forms. Thus there are six fragments of the LBD referred to herein: three short forms, LBDAS, LBDBS, and LBDCS, and three long forms, LBDAL, LBDBL, and LBDCL.

Mutagenesis of fusion proteins C7LBDA and C7LBDB (Example 4) was performed using oligonucleotide mediated site directed mutagenesis (Stratagene; Quikchange, Site-Directed Mutagenesis kit) to substitute an amino acid of choice at various sites on the ER-LBD. This is described in detail in Example 4 including the sequences of the oligonucleotides used for the mutagenesis.

The fusion protein C7-LBD-A is composed of the specific Cys2 His2 zinc finger array defined as C7 combined with LBD-A, which is the specific fragment of ER LBD used. Three ER-LBD fragments are defined: fragment A=ER amino acids 283-554, fragment B=ER amino acids 258-554, fragment C=ER amino acids 212-554. All references to mutants of the ER-LBD will employ human estrogen receptor nomenclature; for example, G 521 R means a mutant ER-LBD which has an arginine substituted for the glycine at amino acid position 521 in wild-type ER-LBD.

In a preferred embodiment, the mutated ER LBD protein includes a mutated estrogen receptor ligand binding region within the region of amino acids 212-554, 258-554, or 283-554.

Mutagenesis studies of the estrogen receptor ligand binding employing the strategy of protein engineering and drug design referred to as the "bumps and holes" approach has shown several large and distinct regions of the receptor ligand binding pocket. See also, Ruff et al., "Structure-function relationship in DNA- and ligand-binding domains of estrogen receptors" *Breast Cancer Res*. 2: 353-359 (2000) and Eiler et al., "Overexpression, purification, and crystal structure of native ERα LBD" *Protein Expr. Purif.* 22: 165-173 (2001), both of which are incorporated herein by reference.

Based on the analyses of the ER-LBD protein-tamoxifen crystal structure "Region 1" is broadly defined as the area adjacent or proximal to the ethyl side chain of 4-OH-tamoxifen. More particularly, Region 1 is comprised of those amino acids within the ER ligand binding domain, any portion of which come within approximately 9 angstroms of the terminal carbon of the ethyl side chain of 4-OH-Tam, also known as position C10 in 4-OH-Tam. Region 1 includes but is not limited to amino acids M388, L391, M421, I424 and L428.

"Region 2" is broadly defined as the area where the D ring of estrogen would be positioned. More particularly, Region 2 is comprised of those amino acids within the ER ligand binding domain, any portion of which come within approximately 9 angstroms of the para position carbon in the ring of 4-OH-Tam that corresponds to the D-ring of estrogen, also known as position C14 in 4-OH-Tam. Region 2 includes but is not limited to amino acid residues G521 and H524.

The substitution of the wild-type amino acid at one or more of these amino acid sites in the ER-LBD with an amino acid of larger or smaller physical size or with different hydrophobic or other physical characteristics results in a ligand binding region with altered ligand responsiveness or selectivity.

Therefore one embodiment of the invention is a steroid hormone receptor protein with one or more of the above amino acids substituted with another amino acid with different physical characteristic so as to alter the ligand binding specificity of the protein.

In a preferred embodiment, the steroid hormone receptor is the ER-LBD, or some portion thereof, i.e., the human estrogen receptor alpha.

In one preferred embodiment, the substituted amino acids are at positions 388, 424 and 428 in the ER LBD.

In a particularly preferred embodiment, the amino acid substitutions are: valine at position 388 in place of methionine in wt ER LBD; tyrosine at position 424 in place of isoleucine in wt ER LBD; and alanine at position 428 in place of leucine in wt ER LBD. This mutant ER LBD is referred to as "388V/424Y/428A".

In another embodiment of the invention, the substituted amino acids are at position 421 and 428 in the ER-LBD.

In a particularly preferred embodiment, the amino acid substitutions are: valine at position 421 in place of methionine in wt ER LBD and alanine at position 428 in place of leucine in wt ERLBD. This mutant ERLBD is referred to as "421V/428A".

In another embodiment of the invention, a single amino acid substitution at position 524 is made.

In a particularly preferred embodiment, this is the substitution of glycine at position 524 of the ER-LBD for histidine in the wild-type ER-LBD. This mutant is referred to as "H524G"

Mutants of the wild-type ER LBD produced by substituting the amino acids at one or more of positions 388, 391, 421, 424, 428, 521 and 524 show ligand binding affinities that are markedly different from the wild-type ER LBD. These mutants may show little or no response to estrogen or to tamoxifen, but are specifically activated by the custom-made novel synthetic compounds of this invention.

For example, as shown in Table 1 below, the in vitro pharmacological profiles on transactivation of C7 ER 388V/424Y/428A comparing estrogen ($E_2$), 4-hydroxy tamoxifen (4-OHT) and the novel synthetic compound LBB 938. As can be seen, the $EC_{50}$ (nM) for $E_2$ is 216.5, for 4-OHT is 157.7 and for LBB 938 is 28.4.

TABLE 1

Pharmacological potency of ER-LBD 388V/424Y/428A transactivation

| | LBB938 | 4-OHT | $E_2$ |
|---|---|---|---|
| EC50 ± STDEV (nM) | 28.4 ± 10.5* | 157.7 ± 57.5 | 216.5 ± 42.3 |

HeLa cells were cotransfected with pC7ERLBD 388V/424Y/428A and p6x2C7Luc reporter plasmids and were treated with 0.1 to 1000 nM compounds as described in Example 1. Sigmoidal dose-response curve fitting for each compound was performed as described in Example 5 (Drug activation on wt ER). EC50 values represent the mean from two or more experiments.
*p < 0.05, compared to 4-OHT or estradiol, the difference in EC50 value is statistically significant.

Thus, the mutant ER LBD 388V/424Y/428A is approximately eight times as sensitive to LBB 938 as to the normal ligand for the wild-type receptor, i.e., estrogen. Thus, in one embodiment of the invention, the compound LBB 938 can be used as a ligand to activate ER LBD 388V/424Y/428A as part of a molecular switch. The levels of LBB 938 required to activate the LBD are obtainable in vitro or in vivo. In addition, normal endogenous levels of estrogen, in animals, including humans should have little or no effect on the functioning of the molecular switch since these levels are in the sub nanomolar region.

Thus, one aspect of the invention is the use of the 388V/424Y/428A mutant in the LBD of a molecular switch and the novel compound LBB 938 to control activation of the switch.

Another aspect of the invention is the use of the mutant LBD 421V/428A as part of a molecular switch with the use of either compound LBB 551 or LBC 081 as the ligand used to activate the switch. As shown in Table 2 below, the pharmacological profile of carbamated tamoxifen transactivation on C7 ER 421V/428A, the $EC_{50}$(nM) of both LBB 551 and LBC 081 are similar to that of $E_2$, i.e., 4.89, 11.66 and 7.23, respectively. However, a concentration of 7.23 nM of estrogen is much higher than normal endogenous estrogen concentration in humans. Therefore the ability of endogenous levels of estrogen to activate the LBD containing the 421V/428A mutant is negligible. However, concentrations of either LBB 551 or LBC 081 sufficient to activate a molecular switch incorporating the LBD mutant 421V/428A could easily be obtained by administration of the drug to the subject. Furthermore, the level of LBB 551 or LBC 081 required to activate the 421V/428A switch is far below the IC50 of either of these compounds on wild-type ER (See Table 4).

TABLE 2

Pharmacological potency of ER-LBD 421V/428A transactivation

| | LBB551 | LBC081 | 4-OHT | $E_2$ |
|---|---|---|---|---|
| EC50 ± STDEV (nM) | 4.89 ± 1.01 | 11.66 ± 4.86 | 0.044 ± 0.001 | 7.23 ± 3.96 |

HeLa cells were cotransfected with pC7ERLBD 388V/424Y/428A and p6x2C7Luc reporter plasmids and were treated with 0.003 to 1000 nM compounds as described in Example 1 (Cell based reporter assay). EC50 values represent the mean from two or more experiments.

Thus, another aspect of the present invention is the use of the 421V/428A mutant in the LBD of a molecular switch to be controlled/activated by administration of either compound LBB 551 or LBC 081.

Another aspect of the invention is the use of the mutant LBD H524G as part of a molecular switch with the use of the novel compound LBF 580 as the ligand used to activate the switch. FIG. 6 shows the fold induction of H524G by a variety of ligands at a concentration of 10 nM. At this concentration, LBF 580 is capable of almost nine times the degree of induction of H524G as compared to estrogen. Table 3 below shows the EC50 of estrogen for the H524G mutant is 18.47 mM which is far above the normal endogenous level of estrogen. Thus, this mutant is not significantly activated by physiological, i.e., subnanomolar concentrations, of estrogen. However, Table 4 below shows that the IC50 of this compound for wild-type estrogen receptor is 252.3. This demonstrates the large concentration range over which this compound could be used to activate the H524G mutant while having little or no effect on wild-type estrogen receptor.

TABLE 3

Pharmacological potency of ER-LBD H524G transactivation

| | LBF580 | 4-OHT | $E_2$ |
|---|---|---|---|
| EC50 ± STDEV (nM) | ≦25* | 2.39 ± 0.29 | 18.47 ± 11.7 |

*Data not show.

The ability of the novel compounds of the invention to serve as ligands to activate molecular switches in vivo is also shown in Table 4 below, which shows the reduced inhibitory activity of the four novel modified tamoxifen derivatives on $E_2$ transactivation on wild-type ER. The inhibitory activity of these compounds on wild-type ER is minimal compared to the inhibitory activity of the parent compound 4-hydroxy tamoxifen.

TABLE 4

Inhibition of $E_2$ activity on wild-type ER by modified tamoxifen derivatives

| | LBB938 | LBB551 | LBC081 | LBF580 | 4-OHT |
|---|---|---|---|---|---|
| IC50 ± STDEV (nM) | 387.7 ± 12.1* | 955.3 ± 378.7* | 844.6 ± 142.7* | 253.3 ± 58.5* | 0.86 ± 0.07 |

COS-7 cells were cotransfected with pHEGO and pERETkLuc reporter plasmids and treated with $E_2$ + 0.1 to 1000 nM compounds as described in Example 5 (Drug activation on wt ER).
IC50 values represent the mean from two or more experiments.
* $p < 0.05$, compared to 4-OHT, the difference in IC50 value is statistically significant.

Thus, the utility of the use, in a molecular switch, of the disclosed combinations of specific mutant of the ER LBD and the specific novel tamoxifen derivative is seen, in that the mutant ER LBD's are minimally, if at all, responsive to physiological concentration of estrogen, and so any of these mutants could be used in a molecular switch without problematic interference from endogenous estrogen levels. In addition, the novel ligands have minimal activity on the wild-type ER receptor. This property avoids the side effects produced by the administration of pharmacologically effective inhibitors of estrogen to animals including humans.

The present invention further provides plasmids containing mutated steroid hormone receptor proteins. Plasmids of the present invention may contain mutant proteins of any of the hormones in the steroid hormone receptor superfamily.

The present invention also provides transfected cells containing plasmids having mutated steroid hormone receptor proteins inserted therein. Useful cells for transfection include yeast, mammalian and insect cells. The present invention also provides stable cell lines transformed with the plasmids of the present invention.

Another alternative embodiment of the present invention is a molecular switch for regulating expression of a heterologous nucleic acid sequence in gene therapy. In one embodiment of this aspect of the present invention, the molecular switch for regulating expression of a heterologous nucleic acid cassette in gene therapy, comprises a modified steroid receptor which includes a natural steroid receptor DNA binding domain attached to a modified ligand binding domain.

In the preferred embodiment of the molecular switch, the modified ligand binding domain is from human estrogen receptor alpha and binds only ligand compounds which are non-natural ligands, synthetic ligands or non-native ligands.

One skilled in the art readily recognizes that the modified ligand binding domain may bind native ligands, such as endogenous estrogen, but there is insignificant binding and thus very little, if any, regulation.

In preferred embodiments, the modified steroid receptor is a human estrogen receptor alpha with the DNA binding domain replaced with a DNA binding domain selected from the group consisting of: $Cys_2His_2$ type (C2H2), GAL-4 DNA, virus DNA binding domain, insect DNA binding domain and a non-mammalian DNA binding domain.

The molecular switch can be further modified by the addition of a transactivation domain. The transactivation domains which are usually used include VP 16, TAF-1, TAF-2, TAU-1 and TAU-2 and p65. One skilled in the art will readily recognize that a variety of other transactivation domains are available.

In a preferred embodiment the molecular switch comprises a mutated human estrogen receptor alpha ligand binding domain and the $Cys_2His_2$ zinc finger DNA binding domain and a transactivation domain such as TA2.

One skilled in the art will readily recognize the molecular switch can be made tissue specific by selecting the appropriate transactivation domains, ligand binding domains and DNA binding domains. In particular, one skilled in the art readily recognizes that by adding a transactivation domain which is specific to a given tissue the molecular switch will only work in that tissue. Also, the addition of a tissue-specifics cis-element to the target gene will aid in providing tissue-specific expression.

The present invention also envisions a method of regulating gene expression of a nucleic acid cassette in gene therapy. This method comprises the step of attaching the molecular switch to a nucleic acid cassette used in gene therapy. In the preferred embodiment, the nucleic acid sequence which is expressed is heterologous. The combined nucleic acid cassette/molecular switch is then administered in a pharmacological dose to a animal or human to be treated or to a transgenic animal or to a plant.

One skilled in the art readily appreciates that the combined nucleic acid cassette/molecular switch can be introduced into the cell in a variety of ways both in vivo and ex vivo. The introduction can be by transfection or transduction. After the nucleic acid cassette/molecular switch is introduced into the cell, the cassette in the resultant transformed cell can be either up-regulated (turned on) or down-regulated (turned off) by introducing to the animal or human a pharmacological dose of a ligand which binds the modified ligand binding site.

In one embodiment of the present invention there is a method for regulating nucleic acid cassette expression in gene therapy comprising the step of linking a molecular switch to a nucleic acid cassette. This molecular switch/nucleic acid cassette is introduced into a cell to form a transformed cell. The transformed cell is then inserted in a pharmacological dose into a human or animal for gene therapy.

In another embodiment the molecular switch/nucleic acid cassette is directly injected into a targeted cell in vivo for gene therapy.

Polypeptides that function as ligand activated transcriptional regulators and nucleic acid molecules encoding such polypeptides are provided. The polypeptides are fusion proteins that are ligand activated transcriptional regulator that can be targeted to any desired endogenous or exogenous gene. Variants of the fusion protein can be designed to have different selectivity and sensitivity for endogenous and exogenous ligands.

Nucleic acid molecules encoding the fusion proteins, expression vectors containing the nucleic acids and cells containing the expression vectors are provided. The fusion protein or nucleic acids, particularly vectors, that encode the fusion protein can be introduced into a cell and, when expressed in the cell, regulate gene expression in a ligand-dependent manner Fusion Proteins The fusion proteins provided herein contain a ligand binding domain (designated herein LBD) from an intracellular receptor, preferably a LBD that has modified ligand specificity compared to the native intracellular receptor from which the LBD originates, and a nucleic acid binding domain (designated herein DBD) that can be tailored for any desired specificity. The fusion proteins may also include a transcriptional regulating domain (designated herein TRD), particularly a repressor or activator domain. The domains are operatively linked whereby the resulting fusion protein functions as a ligand-regulated targeted transcription factor.

When delivered to the nucleus of a cell, the domains, which are operatively linked, together act to modulate the expression of a targeted gene, which may be a native gene in a cell or a gene that also is delivered to a cell. Hence the targeted gene can be an endogenous cellular gene or an exogenously supplied recombinant polynucleotide construct. The fusion protein may also include a transcriptional regulating domain that is selected to activate, enhance or suppress transcription of a targeted gene.

In another embodiment, the fusion protein binds to a naturally occurring gene and modulates the transcription of the naturally occurring gene in a ligand-dependent way. In another embodiment, the fusion protein binds to an exogenously supplied recombinant construct and modulates the transcription of the exogenously supplied recombinant construct in a ligand-dependent way.

In a preferred embodiment, the isolated recombinant fusion protein forms a dimer when bound to a polynucleotide. The dimer can be a homodimer or a heterodimer. In one embodiment, the dimer includes at least one DNA binding domain, at least one, preferably two, ligand binding domains and at least one transcription-modulating domain.

Ligand Binding Domain (LBD)

In a preferred embodiment, the LBD is derived from an intracellular receptor, particularly a steroid hormone receptor. The receptors from which the LBD is derived include, but is not limited to, glucocorticoid receptors, mineralocorticoid receptors, thyroid hormone receptors, retinoic acid receptors, retinoid X receptors, Vitamin D receptors, COUP-TF receptors, ecdysone receptors, Nurr-1 receptors, orphan receptors and variants thereof. Receptors of these types include, but are not limited to, estrogen receptors, progesterone receptors, glucocorticoid-a receptors, glucocorticoid-β receptors, androgen receptors and thyroid hormone receptors. LBDs preferably are modified to alter ligand specificity so that they preferentially bind to an exogenous ligand, such as a drug, compared to an endogenous ligand.

When intended for human gene therapy, the ligand binding domain preferably retain sufficient identity to a human ligand binding domain to avoid substantial immunological response, preferably at least about 90% sequence identity, more preferably at least about 95% sequence identity, and most preferably at least about 99% sequence identity.

The LBD is preferably modified so that it does not bind to the endogenous ligand for the receptor from which the LBD is derived, but to a selected ligand to permit fine tuned regulation of targeted genes. Hence, in certain embodiments, the ligand-binding domain has been modified to change its ligand selectivity compared to its selective in the native receptor. Preferably the modified ligand-binding domain is not substantially activated by endogenous ligands. Any method for altering ligand specificity, including systematic sequence alteration and testing for specificity, and selection protocols (see, e.g., U.S. Pat. No. 5,874,534 and Wang et al., (1994) *Proc. Natl. Acad. Sci. U.S.A.* 91:8180-8184) can be used.

Nucleic Acid Binding Domain (DBD)

To achieve targeted and specific transcriptional regulation the DBD includes at least one zinc finger modular unit and is engineered to bind to targeted genes. The zinc finger nucleic acid binding domain contains at least two zinc finger modules that bind to selected sequences of nucleotides. Any zinc finger or modular portions thereof can be used. The DBD replaces or supplements the naturally-occurring zinc finger domain in the receptor from which the ligand binding domain is derived.

The nucleic acid binding domain (DBD) includes at least one, preferably at least two, modular units of a zinc finger nucleic acid binding polypeptide, each modular unit specifically recognizing a three nucleotide sequence of bases. The resulting DBD binds to a contiguous sequence of nucleotides of from 3 to about 18 nucleotides. As noted, the DBD contains modular zinc-finger units, where each unit is specific for a trinucleotide. Modular zinc protein units can be combined so that the resulting domain specifically binds to any targeted sequence, generally DNA, such that upon binding of the fusion protein to the targeted sequence transcription of the targeted gene is modulated.

The zinc finger-nucleotide binding portion of the fusion protein can be derived or produced from a wild-type zinc finger protein by truncation or expansion, or as a variant of a wild-type-derived polypeptide by a process of site directed mutagenesis, or by combination of a variety of modular units or by a combination of procedures.

$Cys_2His_2$ (C2H2) type zinc finger proteins are exemplary of the zinc fingers that can replace the naturally occurring DNA binding domain in an intracellular receptor, such as the C4-C4 type domain in a steroid receptor, to form a functional ligand-responsive transcription factor fusion protein. By virtue of the zinc finger, the resulting fusion protein exhibits altered DNA binding specificity compared to the unmodified intracellular receptor.

The optimal portion of the ligand binding domain (LBD) of the receptor to use, the zinc finger array and extent thereof and the stoichiometry and orientation of DNA binding can be empirically determined as exemplified herein for a steroid receptor.

In preferred embodiments the zinc-finger portion of the fusion protein binds to a nucleotide sequence of the formula $(GNN)_n$, where G is guanidine, N is any nucleotide and n is an integer from 1 to 6, and typically n is 3 to 6. Preferably, the zinc-finger modular unit is derived from C2H2 zinc-finger peptide.

Transcription Regulating Domain (TRD)

The fusion proteins also can include transcription regulating domains. In preferred embodiments, the transcription regulating domain includes a transcription activation domain. Preferably, the transcription regulating domain has at least about 90% sequence identity to a mammalian, including human if the fusion protein is intended for human gene therapy, transcription regulating domain to avoid inducing undesirable immunological responses. More preferably this sequence identity is at least about 95%, and most preferably this sequence identity is at least about 99%.

The transcription regulating domain can be any such domain known to regulate or prepared to regulate eukaryotic transcription. Such TRDs are known, and include, but are not limited to, VP16, VP64, TA2, STAT-6, p65, or portions derived from these and derivatives, multimers and combinations thereof that exhibit transcriptional regulation properties. The transcription regulating domain can be derived from an intracellular receptor, such as a nuclear hormone receptor transcription activation (or repression) domain, and is preferably a steroid hormone receptor transcription activation domain or variant thereof that exhibits transcriptional regulation properties. Transcription domains include, but are not limited to, TAF-1, TAF-2, TAU-1, TAU-2, and variants thereof.

The transcription regulating domain may be a viral transcription activation domain or variant thereof. Preferably, the viral transcription regulating domain comprises a VP16 transcription activation domain or variant thereof.

The transcription regulating domain can include a transcription repression domain. Such domains are known, and include, but are not limited to, transcription repression domains selected from among ERD, KRAB, SID, Deacetylase, and derivatives, multimers and combinations thereof, such as KRAB-ERD, SID-ERD, $(KRAB)_2$, $(KRAB)_3$, KRAB-A, $(KRAB-A)_2$, $(SID)2$ $(KRAB-A)$-SID and SID-(KRAB-A).

Nucleic Acid Constructs

Also provided are nucleic acid molecules that encode the resulting fusion proteins. The nucleic acids can be included in vectors, suitable for expression of the proteins and/or vectors suitable for gene therapy. Cells containing the vectors are also provided. Typically the cell is a eukaryotic cell. In other embodiments, the cell is a prokaryotic cell.

Also provided are expression cassettes that contain a gene of interest, particularly a gene encoding a therapeutic product, such as an angiogenesis inhibitor, operatively linked to a transcriptional regulatory region or response element, including sequences of nucleic acids to which a fusion proteins provided herein binds and controls transcription, particularly upon binding of a ligand to the LBD of the fusion polypeptide. Such expression cassettes can be included in a vector for gene therapy, and are intended for administration with, before or after, administration of the fusion protein or nucleic acid encoding the fusion protein. Genes of interest for exogenous delivery typically encode therapeutic proteins, such as growth factors, growth factor inhibitors or antagonists, tumor necrosis factor (TNF) inhibitors, anti-tumor agents, angiogenesis agents, anti-angiogenesis agents, clotting factors, apoptotic and other silicide genes.

Compositions, Combinations and Kits

Also provided are compositions that contain the fusion proteins or the vectors that encoded the fusion proteins. Combinations of the fusion proteins or nucleic acids encoding the proteins and nucleic acid encoding a targeted gene with regulatory regions selected for activation by the fusion protein are also provided.

Compositions, particularly pharmaceutical compositions containing the fusion polypeptides in a pharmaceutically acceptable carrier are also provided. In addition, compositions, particularly pharmaceutical compositions containing the synthetic ligands of the invention are provided.

Combinations of the expression cassette and fusion polypeptide or nucleic acid molecules, particularly expression vectors that encode the fusion polypeptide are provided. The combinations may include separate compositions or a single composition containing both elements. Kits containing the combinations and optionally instructions for administration thereof and other reagents used in preparing and administering the combinations are also provided.

Hence compositions suitable for gene therapy that contain nucleic acid encoding the fusion protein, typically in a vector suitable for gene therapy are provided. Preferred vectors include viral vectors, preferably adenoviral vectors, and lentiviral vectors. In other embodiments, non-viral delivery systems, including DNA-ligand complexes, adenovirus-ligand-DNA complexes, direct injection of DNA, $CaPO_4$ precipitation, gene gun techniques, electroporation, liposomes and lipofection are provided.

The compositions suitable for regulating gene expression contain an effective amount of the fusion protein or a polynucleotide encoding the ligand activated transcriptional regulatory fusion protein and a pharmaceutically acceptable excipient. Such compositions can further include a regulatable expression cassette encoding a gene and at least one response element for the gene recognized by the nucleotide binding domain of the fusion polypeptide.

The regulatable expression cassette is designed to include a sequence of nucleic acids with which the nucleic acid binding domain of the ligand activated transcriptional regulatory fusion protein interacts. It also preferably includes operatively linked transcriptional regulatory sequences that are regulatable by the TRD of the fusion protein. Typically, the regulatable expression cassette includes 3 to 6 response elements.

Methods

Methods for regulating expression of endogenous and exogenous genes are provided. The methods are practiced by administering to a cell a composition that contains an effective amount or concentration of the fusion protein or of nucleic acid molecule, such as a vector that encodes the fusion protein. The nucleic acid binding domain (DBD) of the fusion protein is selected to bind to a targeted nucleic acid sequence in the genome of the cell or in an exogenously administered nucleic acid molecule, and the transcription regulating domain (TRD) is selected to regulate transcription from a selected promoter, which typically is operatively linked the targeted nucleic acid binding domain. The exogenously administered nucleic acid molecule comprises an expression cassette encoding a gene of interest and operatively linked to a regulatory region that contains elements, such as a promoter and response elements.

As noted the targeted regulatory region and gene of interest may be endogenously present in the cell or separately administered as part of an expression cassette encoding the gene of interest. If separately administered, it is administered as part of a regulatable expression cassette that includes a gene and at least one response element for the gene recognized by the nucleotide binding domain of the fusion protein.

At the same time or at a later time, a composition containing a ligand that binds to the ligand binding domain of the fusion protein is also administered. The ligand can be administered in the same composition as the fusion protein (or encoding nucleic acid molecule) or in a separate composition. The ligand and fusion protein may be administered sequentially, simultaneously or intermittently.

Hence, gene therapy is effected by administering a ligand that binds to the LBD of the fusion protein. Preferably the ligand is a non-natural or synthetic ligand and the LBD has been modified from the native form present in native intracellular receptors to preferentially and selectively interact with the non-natural ligand. Upon administration, the ligand binds to the ligand binding domain of the fusion protein, whereby the DBD of the fusion protein, either as a monomer or dimer, interacts with a targeted gene and transcription of the targeted gene is repressed or activated. As noted, the targeted gene may be an endogenous gene or an exogenously administered gene.

In other embodiments, the methods for regulating gene expression in a cell are effected by administering to the cell a composition containing an effective amount of the nucleic acid molecule that encodes the ligand activated transcriptional regulatory fusion protein, a regulatable expression cassette containing a gene operatively linked to at least one response element for the gene recognized by the nucleotide binding domain of the polypeptide encoded by the polynucleotide, and a pharmaceutically acceptable excipient; and administering to the cell a ligand that binds to the ligand binding domain of the encoded polypeptide, where the nucleotide binding domain of the encoded polypeptide to binds to the response element and activates or represses transcription of the gene.

Results exemplified herein demonstrate ligand activated transcription of a targeted gene and demonstrate the utility of the fusion protein containing a zinc finger DNA binding domain, such as a mammalian C2H2 DNA binding domain, a modified or mutated ligand binding domain from an intracellular receptor, such as an estrogen receptor, and, optionally, a heterologous transcription regulating domain for the purpose of obtaining ligand-dependent control of expression of a transgene introduced into mammalian cells. Hence it is shown herein that heterologous zinc finger domains can be combined with a variety of mutated intracellular receptors to achieve ligand-dependent gene expression of a targeted gene.

The present invention shows that receptors can be modified to allow them to bind various ligands whose structure differs dramatically from the naturally occurring ligands. For description of how to make the ER mutants of this invention see Example 4.

Selective substitutions of the wild-type amino acid sequence, including substitution of specific amino acids in place of wild-type amino acids at specific sites and truncation, result in altered affinity and altered function of the ligand. By screening receptor mutants, receptors can be customised to respond to ligands that do not activate the host cells own receptors. Thus regulation of a desired transgene can be achieved using a ligand which will bind to and regulate a customised receptor.

Steroid receptors and other mammalian transcription regulators can function in yeast. This fact, coupled with the ease of genetic manipulation of yeast makes it a useful system to study the mechanism of steroid hormone action.

Definitions

Unless defined otherwise, all technical and scientific terms used herein have the same meaning as is commonly understood by one of skill in the art to which this invention belongs. All patents, applications, published applications and other publications and sequences from GenBank and other data bases referred to anywhere in the disclosure herein are incorporated by reference in their entirety and for all purposes.

As used herein, the term "inactive" or "substantially inactive" means, in the context of comparing the activity of a synthetic ligand on a mutant receptor versus a wild-type receptor, that these receptor/drug combinations will allow the selective regulation of a transgene in the absence of any consequential activity on the wild-type receptor. As such, the receptor/drug combinations have the following properties: the synthetic ligand has an EC50 (in nanomolar concentration) [where EC50=concentration providing 50% of maximum activation] which is at least 10 fold lower than the compounds IC50 (nanomolar concentration yielding 50% inhibition of activity) on wild-type receptor. For example: LBB 938 has an EC50 on its preferred target 388V/424Y/428A of approximately 28 nM and an IC50 on wild-type ER of over 380 nM. When a compound is used at a dose less than or equal to 1/10 the IC50 concentration, the inhibitory effect on wild-type ER is generally at or below 10% of total activity, such a compound would be considered inactive or substantially inactive on the wild-type receptor.

As used herein, the "ligand binding domain" (LBD) of the fusion proteins provided herein refers to the portion of the fusion protein responsible for binding to a selected ligand. The LBD optionally and preferably includes dimerization and inactivation functions. The LBDs in the proteins herein are derived from the approximately 300 amino acid carboxyl-terminal half of intracellular receptors, particularly those that are members of the steroid hormone nuclear receptor superfamily. It is the portion of the receptor protein with which a ligand interacts thereby inducing a cascade of events leading to the specific association of an activated receptor with regulatory elements of target genes. In these receptors the LDB includes the hormone binding function, the inactivation function, such as through interactions with heat shock proteins (hsp), and dimerization function. The LBDs used herein include such LBDs and modified derivatives thereof, particularly forms with altered ligand specificity.

As used herein, the "transcription regulating domain" (TRD) refers to the portion of the fusion polypeptide provided herein that functions to regulate gene transcription. Exemplary and preferred transcription activation domains include but are not limited to; VP16, VP64, TA2, STAT-6, p65, or portions derived from these and derivatives. Exemplary and preferred transcription repressor domains include but are not limited to; ERD, KRAB, SID, Deacetylase, and derivatives, multimers and combinations thereof such as KRAB-ERD, SID-ERD, (KRAB)$_2$, (KRAB)$_3$, KRAB-A, (KRAB-A)$_2$, (SID)$_2$ (KRAB-A)-SID and SID-(KRAB-A).

As used herein, a "transcriptional regulatory region" refers to a region that drives gene expression in the target cell. Transcriptional regulatory regions suitable for use herein include but are not limited to the human cytomegalovirus (CMV) immediate-early enhancer/promoter, the SV40 early enhancer/promoter, the JC polyomavirus promoter, the albumin promoter, PGK and the α-actin promoter coupled to the CMV enhancer.

As used herein, the term "nucleic acid cassette" refers to the genetic material of interest which can express a protein, or a peptide, or RNA after it is incorporated transiently, permanently or episomally into a cell. The nucleic acid cassette is positionally and sequentially oriented in a vector with other necessary elements such that the nucleic acid in the cassette can be transcribed and, when necessary, translated in the cell.

Chimeric Gene/Chimeric Construct: A recombinant DNA sequence in which a promoter or regulatory DNA sequence is operatively linked to, or associated with, a DNA sequence that codes for an mRNA or which is expressed as a protein, such that the regulator DNA sequence is able to regulate transcription or expression of the associated DNA sequence. The regulator DNA sequence of the chimeric gene or chimeric construct is not normally operatively linked to the associated DNA sequence as found in nature.

Corresponding To: in the context of the present invention, "corresponding to" means that when the amino acid sequence of a query estrogen receptor is aligned with the amino acid sequence of a subject estrogen receptor (for example, the human ERα sequence given in SEQ ID NO:X), the amino acids in the query estrogen receptor sequence that "correspond to" certain enumerated positions of SEQ ID NO:X are those that align with these positions of SEQ ID NO:X, but are not necessarily in the same numerical positions of the subject estrogen receptor's amino acid sequence.

As used herein, the "DNA binding domain" (DBD), or alternatively the nucleic acid (or nucleotide) binding domain, refers to the portion of the fusion polypeptide provided herein that provides specific nucleic acid binding capability. The use of the abbreviation DBD is not meant to limit it to DNA binding domains, but is also intended to include polypeptides that bind to RNA. The nucleic acid binding domain functions to target the protein to specific genes by virtue of the ability to bind to specific DNA sequences engineered into the promoter. The DBD targets the fusion protein to the selected targeted gene or genes, which gene(s) may be endogenous or exogenously added.

Associated With/Operatively Linked: Refers to two DNA sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence. As used herein, "operatively linked" also means that elements of the fusion polypeptide, for example, are linked such that each perform or functions as intended. For example, the activator is attached to the binding domain in such a manner that, when bound to a target nucleotide via that binding domain, the activator acts to promote transcription. Linkage between and among elements may be direct or indirect, such as via a linker. The elements are not necessarily adjacent. Hence a repressor domain of a TRD can be linked to a DNA binding domain using any linking procedure well known in the art. It may be necessary to include a linker moiety between the two domains. Such a linker moiety is typically a short sequence of amino acid residues that provides spacing between the domains. So long as the linker does not interfere with any of the functions of the binding or repressor domains, any sequence can be used.

As used herein, a "fusion protein" is a protein that contains portions or fragments of two or more naturally-occurring proteins operatively joined or linked to form the fusion protein in which each fragment retains a function or a modified function exhibited by the naturally occurring proteins. The fragments from the naturally occurring protein may be modified to alter the original properties.

"Receptor polypeptide" as used herein refers to polypeptides, e.g. fusion proteins, which can either activate or inhibit the expression of a target nucleic acid sequence in response to an applied chemical ligand. The receptor polypeptide is comprised of a ligand binding domain, a DNA binding domain and a transactivation domain. The ligand binding domain comprises a sequence of amino acids whose structure binds non-covalently a complementary chemical ligand. Hence, a ligand binding domain and its chemical ligand form a complementary binding pair. The DNA binding domain comprises a sequence of amino acids which binds non-covalently a specific nucleotide sequence known as a response element (RE). One or more response elements are located in the 5' regulatory region of the target expression cassette. Each RE comprises a pair of half-sites, each half-site having a 5-6 base pair core where a single DNA binding domain recognizes a single half-site. The half-sites may be arranged in relative linear orientation to each other as either direct repeats, palindromic repeats or inverted repeats. The nucleotide sequence, spacing and linear orientation of the half-sites determine which DNA binding domain or domains will form a complementary binding pair with the response element. The transactivation domain comprises one or more sequences of amino acids acting as subdomains which affect the operation of transcription factors during preinitiation and assembly at the TATA box. The effect of the transactivation domain is to allow repeated transcription initiation events, leading to greater levels of gene expression.

A "receptor expression cassette" comprises a nucleotide sequence for a 5' regulatory region operably linked to a nucleotide sequence which encodes a receptor polypeptide and an untranslated 3' termination region (stop codon and polyadenylation sequence). The 5' regulatory region is capable of promoting expression in transformed cells.

A "target expression cassette" comprises a nucleotide sequence for a 5' regulatory region operably linked to a target nucleic acid sequence of interest, which e.g. may encode a protein whose expression is either activated or inhibited by the receptor polypeptides in the presence of a chemical ligand. The 5' regulatory region of the target expression cassette comprises a core promoter sequence, an initiation of transcription sequence and the response element or response elements necessary for complementary binding of the receptor polypeptides. The 5' regulatory region is capable of promoting expression in transformed cells. The target expression cassette also possesses a 3' termination region (stop codon and polyadenylation sequence).

As used herein, "modulating" envisions the activation of, or the inhibition or suppression of expression from a promoter when it is over-activated, or enhancement of expression from such a promoter when it is underactivated.

As used herein, "steroid hormone receptor superfamily" refers to the superfamily of intracellular receptors that are steroid receptors. Representative examples of such receptors include, but are not limited to, the estrogen (both alpha and beta), progesterone, glucocorticoid-$\alpha$, glucocorticoid-$\beta$, mineralocorticoid, androgen, thyroid hormone, retinoic acid, retinoid X, Vitamin D, COUP-TF, ecdysone, Nurr-1 and orphan receptors.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Bejacmin/Cummings Pub. co., p.224).

As used herein, a "delivery plasmid" is a plasmid vector that carries or delivers nucleic acids encoding a therapeutic gene or gene that encodes a therapeutic product or a precursor thereof or a regulatory gene or other factor that results in a therapeutic effect when delivered in vivo in or into a cell line, such as, but not limited to a packaging cell line, to propagate therapeutic viral vectors.

As used herein, "recombinant expression vector" or "expression vector" refers to a plasmid, virus or other vehicle known in the art that has been manipulated by insertion or incorporation of heterologous DNA, such as nucleic acid encoding the fusion proteins herein or expression cassettes provided herein. Such expression vectors contain a promotor sequence for efficient transcription of the inserted nucleic acid in a cell. The expression vector typically contains an origin of replication, a promoter, as well as specific genes that permit phenotypic selection of transformed cells.

As used herein, a DNA or nucleic acid "homolog" refers to a nucleic acid-that includes a preselected conserved nucleotide sequence, such as a sequence encoding a therapeutic polypeptide. By the term "substantially homologous" is meant having at least 80%, preferably at least 90%, most preferably at least 95% homology therewith or a less percentage of homology or identity and conserved biological activity or function.

As used herein, "host cells" are cells in which a vector can be propagated and its DNA expressed. The term also includes any progeny of the subject host cell. It is understood that all progeny may not be identical to the parental cell since there may be mutations that occur during replication. Such progeny are included when the term "host cell" is used. Methods of stable transfer where the foreign DNA is continuously maintained in the host are known in the art.

The terms "homology" and "identity" are often used interchangeably. In this regard, percent homology or identity may be determined, for example, by comparing sequence information using a GAP computer program. The GAP program uses the alignment method of Needleman and Wunsch ((1970) *J. Mol. Biol.* 48:443), as revised by Smith and Waterman ((1981) *Adv. Appl. Math*. 2:482). Briefly, the GAP program defines similarity as the number of aligned symbols (i.e., nucleotides or amino acids) which are similar, divided by the total number of symbols in the shorter of the two sequences. The preferred default parameters for the GAP program may include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., *ATLAS OF PROTEIN SEQUENCE AND STRUCTURE*, National Biomedical Research Foundation, pp. 353-358 (1979); (2) a penalty of 3.0 for each gap and an additional 0.10 penalty for each symbol in each gap; and (3) no penalty for end gaps.

Whether any two nucleic acid molecules have nucleotide sequences that are at least 80%, 85%, 90%, 95%, 96%, 97%, 98% or 99% "identical" can be determined using known computer algorithms such as the "FAST A" program, using for example, the default parameters as in Pearson et al. (1988) *Proc. Natl. Acad. Sci. USA* 85:2444. Alternatively the BLAST function of the National Center for Biotechnology Information database maybe used to determine identity In general, sequences are aligned so that the highest order match is obtained. "Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in*

*Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carillo et al. (1988) *SIAM J Applied Math* 48:1073). Methods commonly employed to determine identity or similarity between two sequences include, but are not limited to, those disclosed in Guide to Huge Computers, Martin J. Bishop, ed., Academic Press, San Diego, 1994, and Carillo et al. (1988) *SIAM J Applied Math* 48:1073. Methods to determine identity and similarity are codified in computer programs. Preferred computer program methods to determine identity and similarity between two sequences include, but are not limited to, GCG program package (Devereux, J. et al., *Nucleic Acids Research* 12(I):387 (1984)), BLASTP, BLASTN, FASTA (Atschul, S. F. et al., *J. Molec Biol* 215:403 (1990)).

Therefore, as used herein, the term "identity" represents a comparison between a test and a reference polypeptide or polynucleotide. For example, a test polypeptide may be defined as any polypeptide that is 90% or more identical to a reference polypeptide. As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons may be made between a test and reference polynucleotides. Such differences may be represented as point mutations randomly distributed over the entire length of an amino acid sequence or they may be clustered in one or more locations of varying length up to the maximum allowable, e.g. 10/100 amino acid difference (approximately 90% identity). Differences are defined as nucleic acid or amino acid substitutions, or deletions.

As used herein, "primer" refers to an oligonucleotide containing two or more deoxyribonucleotides or ribonucleotides, preferably more than three, from which synthesis of a primer extension product can be initiated. For purposes herein, a primer of interest is one that is substantially complementary to a zinc finger-nucleotide binding protein strand, but also can introduce mutations into the amplification products at selected residue sites. Experimental conditions conducive to synthesis include the presence of nucleoside triphosphates and an agent for polymerization and extension, such as DNA polymerase, and a suitable buffer, temperature and pH.

As used herein, "genetic therapy" or "gene therapy" involves the transfer of heterologous DNA to the certain cells, target cells, of a mammal, particularly a human, with a disorder or conditions for which such therapy is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product, or it may encode a product, such as a peptide or RNA that in some manner mediates, directly or indirectly, expression of a therapeutic product. Genetic therapy may also be used to deliver nucleic acid encoding a gene product that replaces a defective gene or supplements a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof. Genetic therapy may also involve delivery of an inhibitor or repressor or other modulator of gene expression.

As used herein, "heterologous DNA" is DNA that encodes RNA and proteins that are not normally produced in vivo by the cell in which it is expressed or that mediates or encodes mediators that alter expression of endogenous DNA by affecting transcription, translation, or other regulatable biochemical processes. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

Hence, herein heterologous DNA or foreign DNA, includes a DNA molecule not present in the exact orientation and position as the counterpart DNA molecule found in the genome. It may also refer to a DNA molecule from another organism or species (i.e., exogenous).

As used herein, a "therapeutically effective product" is a product that is encoded by heterologous nucleic acid, typically DNA, that, upon introduction of the nucleic acid into a host,. a product is expressed that ameliorates or eliminates the symptoms, manifestations of an inherited or acquired disease or that cures the disease.

Typically, DNA encoding a desired gene product is cloned into a plasmid vector and introduced by routine methods, such as calcium-phosphate mediated DNA uptake (see, (1981) *Somat. Cell. Mol. Genet.* 7:603-616) or microinjection, into producer cells, such as packaging cells. After amplification in producer cells, the vectors that contain the heterologous DNA are introduced into selected target cells.

As used herein, an expression or delivery vector refers to any plasmid or virus into which a foreign or heterologous DNA may be inserted for expression in a suitable host cell—i.e., the protein or polypeptide encoded by the DNA is synthesized in the host cell's system. Vectors capable of directing the expression of DNA segments (genes) encoding one or more proteins are referred to herein as "expression vectors." Also included are vectors that allow cloning of cDNA (complementary DNA) from mRNAs produced using reverse transcriptase.

As used herein, a "gene" refers to a nucleic acid molecule whose nucleotide sequence encodes an RNA or polypeptide. A gene can be either RNA or DNA. Genes may include regions preceding and following the coding region (leader and trailer) as well as intervening sequences (introns) between individual coding segments (exons).

As used herein, "isolated" with reference to a nucleic acid molecule or polypeptide or other biomolecule means that the nucleic acid or polypeptide has separated from the genetic environment from which the polypeptide or nucleic acid were obtained. It may also mean altered from the natural state by the hand of man. For example, a polynucleotide or a polypeptide naturally present in a living animal is not "isolated," but the same polynucleotide or polypeptide separated from the coexisting materials of its natural state is "isolated," as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source.

Thus, by "isolated" the nucleic acid is typically free of the coding sequences of those genes that, in a naturally-occurring genome immediately flank the gene encoding the nucleic acid of interest. Isolated DNA may be single-stranded or double-stranded, and may be genomic DNA, cDNA, recombinant hybrid DNA, or synthetic DNA. It may be identical to a native DNA sequence, or may differ from such sequence by the deletion, addition, or substitution of one or more nucleotides.

Purified, as it refers to preparations made from biological cells or hosts means any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. The procedures may include for example, but are not limited to, ammonium sulfate fractionation, gel filtration, ion exchange change chromatography, affinity chromatography, density gradient centrifugation and electrophoresis. A recombinantly produced version of a compounds can be substantially purified by the one-step method described in Smith et al. (1988) Gene 67:31-40.

A preparation of DNA or protein that is "substantially pure" should be understood to mean a preparation free from naturally occurring materials with which such DNA or protein is normally associated in nature. "Essentially pure" should be understood to mean a "highly" purified preparation that contains at least 95% of the DNA or protein of interest.

As used herein, "modified" or "mutated" means altered from its natural state by the hand of man. In the context of the modified estrogen receptor alpha ligand binding domain of the invention, having modifications in one or both of Regions 1 and 2, "modified" is intended to encompass amino acid mutations, substitutions, insertions, and deletions.

A cell extract that contains the DNA or protein of interest should be understood to mean a homogenate preparation or cell-free preparation obtained from cells that express the protein or contain the DNA of interest. The term "cell extract" is intended to include culture media, especially spent culture media from which the cells have been removed.

As used herein, "modulate" refers to the suppression, enhancement or induction of a function. For example, zinc finger-nucleic acid binding domains and variants thereof may modulate a promoter sequence by binding to a motif within the promoter, thereby enhancing or suppressing transcription of a gene operatively linked to the promoter cellular nucleotide sequence. Alternatively, modulation may include inhibition of transcription of a gene where the zinc finger-nucleotide binding polypeptide variant binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript.

As used herein, "inhibit" refers to the suppression of the level of activation of transcription of a structural gene operably linked to a promoter.

As used herein, a "promoter" region of a gene, in the context of the molecular switch-dependent, i.e. regulatable promoter, expression cassette, means the combination of a so-called minimal promoter operatively linked to one or more repeats of a defined Cys2-His2 zinc finger array binding site. A minimal promoter is understood to mean a region of any cellular or viral promoter typically containing the TATA box and transcription start site, but devoid of most or all enhancer elements. As such, the minimal promoter has a low basal transcription level relative to the full promoter region. Examples of minimal promoters used in this application include a short fragment from the SV40 promoter and an approximately 40 bp region containing the TATA box from the c-fos gene.

As used herein, the term "basal activity" means the level of gene expression observed in the absence of a specific stimulus. In the case of the molecular switch and regulated expression cassette, basal activity refers to the level of transgene expression observed in the absence of the activator ligand. If a gene is to be activated, proteins known as transcription factors attach to the promoter region of the gene. This assembly resembles an "on switch" by enabling an enzyme to transcribe a second genetic segment from DNA into RNA. In most cases the resulting RNA molecule serves as a template for synthesis of a specific protein; sometimes RNA itself is the final product.

The term "effective amount" when used in the context of the administration of a synthetic ligand means an amount of the ligand to produce a concentration sufficient to activate the ligand binding region of the molecular switch being use.

As used herein, a polypeptide "variant" or "derivative" refers to a polypeptide that is a mutagenized form of a polypeptide or one produced through recombination but that still retains a desired activity, such as the ability to bind to a ligand or a nucleic acid molecule or to modulate transcription.

As used herein, a ligand binding domain that is a "mutant," "modified," "modification," "variant" or "derivative" or other such term refers to an alteration of the domain in question from a native or wild-type ligand binding domain to one produced through amino acid substitution. Thus, a "mutant," "variant" or "derivative" includes a ligand binding domain in which one or more wild-type amino acids are substituted with alternate amino acids, and includes primary sequence changes. Similar terms are used to refer to "mutant," "variant" or "derivative" transcription effector domains.

As used herein a "zinc finger-nucleotide binding motif" refers to any two or three-dimensional feature of a nucleotide segment to which a zinc finger-nucleotide binding derivative polypeptide binds with specificity. Included within this definition are nucleotide sequences, generally of five nucleotides or less, as well as the three dimensional aspects of the DNA double helix, such as, but are not limited to, the major and minor grooves and the face of the helix. The motif is typically any sequence of suitable length to which the zinc finger polypeptide can bind. For example, a three finger polypeptide binds to a motif typically having about 9 to about 14 base pairs. Preferably, the recognition sequence is at least about 16 base pairs to ensure specificity within the genome. Therefore, zinc finger-nucleotide binding polypeptides of any specificity are provided. The zinc finger binding motif can be any sequence designed empirically or to which the zinc finger protein binds. The motif may be found in any DNA or RNA sequence, including regulatory sequences, exons, introns, or any non-coding sequence.

As used herein, the terms "pharmaceutically acceptable," "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the composition.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

As used herein with regard to nucleic acid molecules, including DNA fragments, the phrase "operatively linked" means the sequences or segments have been covalently joined, preferably by conventional phosphodiester bonds, into one strand of DNA, whether in single or double stranded form such that operatively linked portions functions as intended. The choice of vector to which transcription unit or a cassette provided herein is operatively linked depends directly, as is well known in the art, on the functional properties desired, e.g., vector replication and protein expression, and the host cell to be transformed, these being limitations inherent in the art of constructing recombinant DNA molecules.

As used herein, a sequence of nucleotides adapted for directional ligation, i.e., a polylinker, is a region of the DNA expression vector that (1) operatively links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. In one embodiment, the directional ligation means is provided by nucleotides present in the upstream translatable DNA sequence, downstream translatable DNA sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

As used herein, a "secretion signal" is a leader peptide domain of a protein that targets the protein to the periplasmic membrane of gram negative bacteria. A preferred secretion signal is a pelB secretion signal. The predicted amino acid residue sequences of the secretion signal domain from two pelB gene product variants from *Erwinia carotova* are described in Lei et al. (*Nature* 331: 543-546, 1988). The leader sequence of the pelB protein has previously been used as a secretion signal for fusion proteins (Better et al. (1988) *Science* 240:1041-1043; Sastry et al. (1989) *Proc. Natl. Acad. Sci. USA* 86:5728-5732; and Mullinax et al. (1990) *Proc. Natl. Acad. Sci. USA*, 87:8095-8099). Amino acid residue sequences for other secretion signal polypeptide domains from *E. coli* are known (see, e.g.,Oliver, In Neidhard, F. C. (ed.), *Escherichia coli* and *Salmonella Typhimurium*, American Society for Microbiology, Washington, D.C., 1:56-69 (1987)).

As used herein, "ligand" refers to any compound interacts with the ligand binding domain of a receptor and modulate its activity; ligands typically activate receptors. Ligand can also include compounds that activate the receptor without binding. A natural ligand is a compound that normally interacts with the receptor.

As used herein, "non-natural" ligands or "non-native" ligands or "synthetic" ligands refer to compounds that are normally are not found in mammals, such as humans, that bind to or interact with the ligand binding domain of a receptor. Hence, the term "non-native ligands" refers to those ligands that are not naturally found in the specific organism (man or animal) in which gene therapy is contemplated. For example, synthetic ligands may be made entirely by chemical synthesis or may be chemically altered naturally occurring compounds such as tamoxifen.

As used herein, "cell-proliferative disorder" denotes malignant as well as non-malignant disorders in which cell populations morphologically appear to differ from the surrounding tissue. The cell-proliferative disorder may be a transcriptional disorder that results in an increase or a decrease in gene expression level. The cause of the disorder may be of cellular origin or viral origin. Treatment can be prophylactic in order to make a plant cell, for example, resistant to a virus, or therapeutic, in order to ameliorate an established infection in a cell, by preventing production of viral products.

As used herein, "cellular nucleotide sequence" refers to a nucleotide sequence that is present within a cell. It is not necessary that the sequence be a naturally occurring sequence of the cell. For example, a retroviral genome that is integrated within a host's cellular DNA, would be considered a "cellular nucleotide sequence". The cellular nucleotide sequence can be DNA or RNA and includes introns and exons, DNA and RNA. The cell and/or cellular nucleotide sequence can be prokaryotic or eukaryotic, including a yeast, virus, or plant nucleotide sequence.

As used herein, "administration" of a therapeutic composition can be effected by any means, and includes, but is not limited to, subcutaneous, intravenous, intramuscular, intrasternal, infusion techniques, intraperitoneally administration and parenteral administration.

Regulatable Cassette

In embodiments in which the targeted gene is an exogenous gene, particularly a gene that encodes a therapeutic product, the gene is provided as in an expression cassette operatively linked to a promoter and regulatory region with which the fusion protein specifically interacts.

The cassette includes at least one polynucleotide domain recognized by the corresponding zinc finger domain present in the fusion protein and a suitable promoter to direct transcription of the exogenous gene.

Typically, the regulatable expression cassette contains three to six response elements and interacts with nucleic acid binding domain of the ligand activated transcriptional regulatory fusion protein.

Typically the exogenous gene encodes a therapeutic product, such as a growth factor, that can supplement peptides, polypeptides or proteins encoded by endogenous expressed genes, thereby providing an effective therapy. In several embodiments the gene encodes a suitable reporter molecule that can be detected by suitable direct or indirect means. The cassette can be inserted into a suitable delivery vehicle for introduction into cells. Such vehicles include, but are not limited to, human adenovirus vectors, adeno-associated vectors, murine or lenti virus derived retroviral vectors, and a variety of non-viral compositions including liposomes, polymers, and other DNA containing conjugates.

Use of the Fusion Proteins for Gene Regulation

Delivery of the Nucleic Acids

There are available to one skilled in the art multiple viral and non-viral methods suitable for introduction of a nucleic acid molecule into a target cell. Genetic modification of a cell may be accomplished using one or more techniques well known in the gene therapy field (*Human Gene Therapy*, April 1994, Vol. 5, p. 543-563; Mulligan, R. C. 1993). Some of the technologies described herein are also applicable to the study of gene expression in in vitro systems or in animal models.

The ability to regulate transgene expression, as defined in the examples herein, can be applied to a wide variety of applications for gene therapy. The ability to control expression of an exogenously introduced transgene is important for the safety and efficacy of most or all envisioned cell and gene therapies. Control of transgene expression can be used to accomplish regulation of a therapeutic protein level, ablation of a desired cell population, either the vector containing cells or others, or activation of a recombinase or other function resulting in control of vector function within the transduced cells. Further, such control permits termination of a gene therapy treatment if necessary.

A number of vector systems useful for gene therapy have been described previously in this application. Vectors for gene therapy include any known to those of skill in the art, and include any vectors derived from animal viruses and artificial chromosomes. The vectors may be designed for integration into the host cell's chromosomes or to remain as extrachromosomal elements. Such vectors include, but are not limited to human adenovirus vectors, adeno-associated viral vectors, retroviral vectors, such as murine retroviral vectors and lentivirus-derived retroviral vectors.

Figure 5:
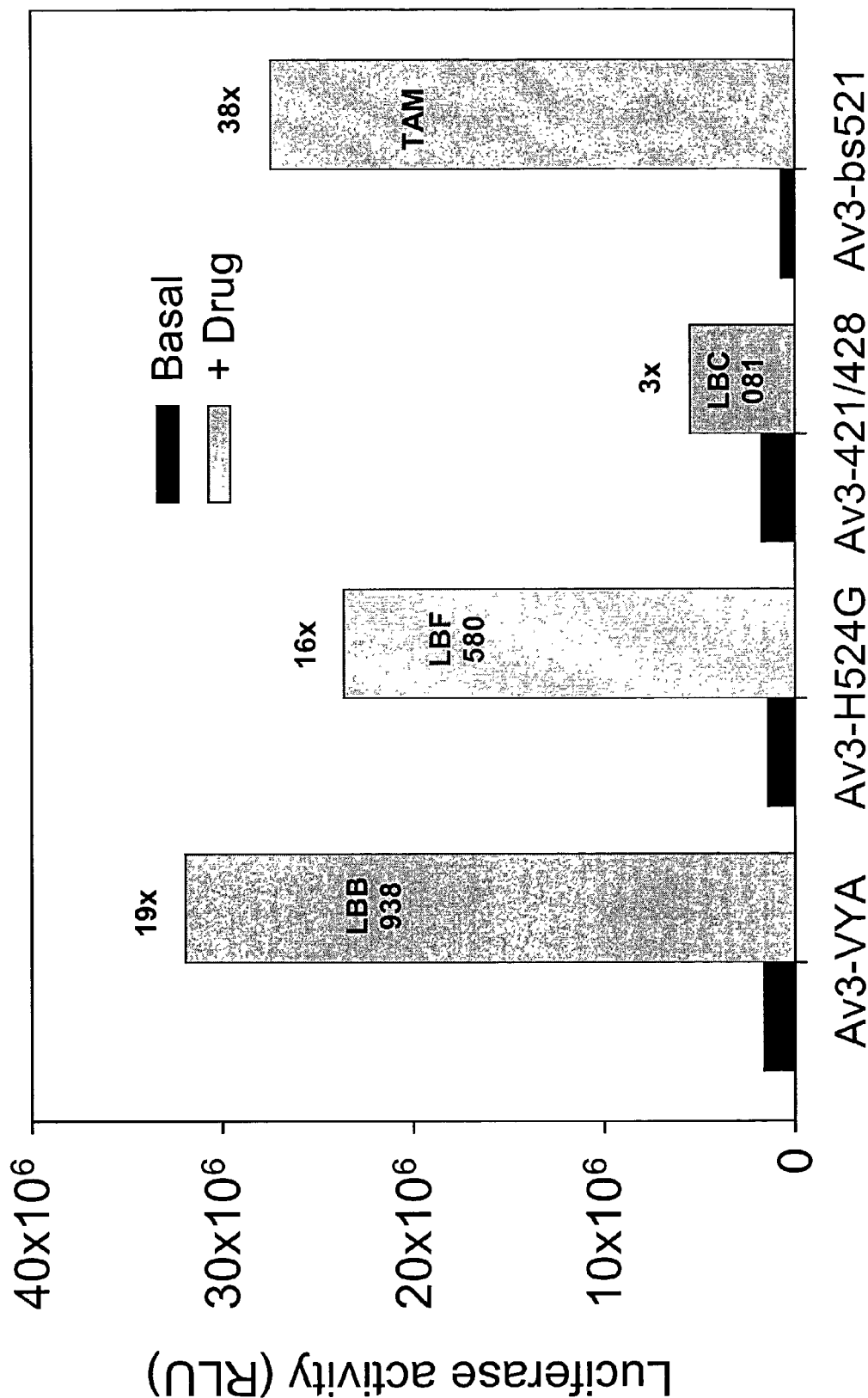
FIG. 5 shows transactivation on adenoviral-delivered ER variants FIG. 6. shows the fold induction at 10 nM for estrogen, 4-hydroxy tamoxifen and the specific synthetic ligand for each of the three mutant ER LBD's

For example, the ER LBD mutants of the present invention were constructed into a replication defective adenoviral vector (Av3) backbone DNA sequence so that this regulatory system could be delivered into cells for clinical application and testing. An Av3 vector containing a series of C7 binding sites linked to an SV40 minimal promoter and luciferase transgene (C7-SV40-luc) was also constructed and delivered simultaneously with each of the Av3 ER LBD mutant vectors. The cells were then exposed to the corresponding ligand to test the capability of the adenoviral-delivered ER mutants to respond to their corresponding ligands and then mediate the transcription of the luciferase transgene in the context of an adenoviral vector. The results are shown in FIG. 5. The Av3-388V/424Y/428A responded to LBB 938 and the luciferase activity was enhanced 19 fold over the basal level. The Av3-H524G construct responded to treatment with LBF 580 and luciferase activity was increased 16 times over the basal level. The level of responsiveness of these two ER mutants was comparable to the level of responsiveness of Av3-bs521, which is the protypical regulator for mediating tamoxifen-induced transgene expression after systemic delivery into mice by the Av3 vector. Xu et al., *Molecular Therapy*, 3:262-273, 2000. The response of Av3-421/428 when treated with LBC 081 was three times basal activity.

Also contemplated herein are any of the variety of non-viral compositions for targeting and/or delivery of genetic material, including, but are not limited to, liposomes, polymers, and other DNA containing compositions, and targeted conjugates, such as nucleic acids linked to antibodies and growth factors. Any delivery system is intended for use of delivery of the nucleic acid constructs encoding the fusion polypeptide and also targeted exogenous genes. Such vector systems can be used to deliver the fusion proteins and the inducible transgene cassette either in vitro or in vivo, depending on the vector system. With adenovirus, for instance, vectors can be administered intravenously to transduce the liver and other organs, introduced directly into the lung, or into vascular compartments temporarily localized by ligation or other methods. Methods for constructing such vectors, and methods and uses thereof are known to those skilled in the field of gene therapy.

In one embodiment, one vector encodes the fusion protein regulator and a second vector encodes the inducible transgene cassette (the target expression cassette). Vectors can be mixed or delivered sequentially to incorporate into cells the regulator and transgene at the appropriate amounts. Subsequent administration of and effective amount of the ligand by standard routes would result in activation of the transgene.

In another embodiment, the nucleic acid encoding the fusion protein and the inducible transgene can be included in the same vector construction. In this instance, the nucleic acid encoding the fusion protein would be positioned within the vector and expressed from a promoter in such a way that it did not interfere with the basal expression and inducibility of the transgene cassette. Further, the use of cell or tissue specific promoters to express the fusion protein confers an additional level of specificity on the system. Dual component vectors and use for gene therapy are known (see, e.g., Burcin et al. (1999) *Proc. Natl. Acad. Sci. USA* 96: 335-360, which describes an adenovirus vector fully deleted of viral backbone genes).

In another embodiment, gene therapy can be accomplished using a combination of the vectors described above. For example, a retroviral vector can deliver a stably integrated, inducible transgene cassette into a population of cells either in vitro (ex vivo) or in vivo. Subsequently, the integrated transgene can be activated by transducing this same cell population with a second vector, such as an adenovirus vector capable of expressing the fusion protein, followed by the administration of the specific ligand inducing agent. This is particularly useful where "one time" activation of the transgene is desired, for example as a cellular silicide mechanism. An example of this application is the stable integration of an inducible transgene cassette containing the herpes simplex virus thymidine kinase gene (HSV Tk). Subsequent activation of this gene confers sensitivity to ganciclovir and allows ablation of this modified cell.

Viral Delivery Systems

Viral transduction methods for delivering nucleic acid constructs to cells are contemplated herein. Suitable DNA viral vectors for use herein includes, but are not limited to an adenovirus (Ad), adeno-associated virus (AAV), herpes virus, vaccinia virus or a polio virus. A suitable RNA virus for use herein includes but is not limited to a retrovirus or Sindbis virus. It is to be understood by those skilled in the art that several such DNA and RNA viruses exist that may be suitable for use herein. Adenoviral vectors have proven especially useful for gene transfer into eukaryotic cells and are widely available to one skilled in the art and is suitable for use herein.

Adeno-associated virus (AAV) has been used as a gene transfer system with applications in gene therapy. See U.S. Pat. Nos. 5,139,941; 5,436,146; and 5,622,856. Herpes simplex virus type-1 (HSV-1) vectors are available and are especially useful in the nervous system because of its neurotropic property. See U.S. Pat. No. 5,288,641. Vaccinia viruses, of the poxvirus family, have also been developed as expression vectors. Each of the above-described vectors is widely available and is suitable for use herein.

Retroviral vectors are capable of infecting a large percentage of the target cells and integrating into the cell genome. Preferred retroviruses include lentiviruses, and also include, but are not limited to, HIV, BIV and SIV. See U.S. Pat. Nos. 5,665,577; 5,994,136; 6,013,516; 5,672,510; 5,707,865 and 5,817,491.

Various viral vectors that can be used for gene therapy as taught herein include adenovirus (See U.S. Pat. No. 5,935,935), herpes virus, vaccinia, adeno-associated virus (AAV), or, preferably, an RNA virus such as a retrovirus, and also include a modified viral vector, such as an adenovirus, known as a "gutless" vector. Preferably, the retroviral vector is a derivative of a murine or avian retrovirus, or is a lentiviral vector. The preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector is made target specific.

Retroviral vectors can be made target specific by inserting, for example, a polynucleotide encoding a protein. Preferred targeting is accomplished by using an antibody to target the retroviral vector. Those of skill in the art know of, or can readily ascertain without undue experimentation, specific polynucleotide sequences which can be inserted into the retroviral genome to allow target specific delivery of the retroviral vector containing the zinc. finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Gutless Viral Vectors

In a particularly preferred embodiment of the present invention the viral vector used is a "gutless" adenoviral vector. Such vectors are devoid of all viral coding regions and contain only the essential adenovirus packaging signals and the transgene expression cassette. (See Example 6). They may be prepared by techniques known to those of skill in the art. Sandig et al. PNAS 97:1002-1007 (2000)

Nonviral Delivery Systems

"Non-viral" delivery techniques for gene therapy include DNA-ligand complexes, adenovirus-ligand-DNA complexes, direct injection of DNA, $CaPO_4$ precipitation, gene gun techniques, electroporation, liposomes and lipofection. Any of these methods are available to one skilled in the art and would be suitable for use herein. Other suitable methods are available to one skilled in the art, and it is to be understood that the herein may be accomplished using any of the available methods of transfection.

Another targeted delivery system is a colloidal dispersion system. Colloidal dispersion systems include macromolecule complexes, nanocapsules, microspheres, beads, and lipid-based systems including oil-in-water emulsions, micelles, mixed micelles, and liposomes, which are preferred. Liposomes are artificial membrane vesicles which are useful as delivery vehicles in vitro and in vivo. It has been shown that large unilamellar vesicles (LUV), which range in size from 0.2-4.0 μm can encapsulate a substantial percentage of an aqueous buffer containing large macromolecules. RNA, DNA and intact virions can be encapsulated within the aqueous interior and be delivered to cells in a biologically active form (Fraley et al., *Trends Biochem. Sci.*, 6:77, 1981).

Lipofection may be accomplished by encapsulating an isolated nucleic acid molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as provide herein, an isolated nucleic acid molecule.

Liposomes have been used for delivery of polynucleotides in plant, yeast and bacterial cells as well as mammalian cells. In order for a liposome to be an efficient gene transfer vehicle, characteristics among the following should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting uses the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system are ligands and receptors permitting the targeted delivery system to find and "home in" on the desired cells. A ligand may be any compound of interest that interacts with another compound, such as a receptor.

In general, surface membrane proteins that bind to specific effector molecules are referred to as receptors. Antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting antibody-zinc finger-nucleotide binding protein-containing liposomes directly to the malignant tumor. Since the zinc finger-nucleotide binding protein gene product may be indiscriminate with respect to cell type in its action, a targeted delivery system offers a significant improvement over randomly injecting non-specific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an the antigenic epitope on the target cells. Liposomes may also be targeted to cells expressing receptors for hormones or other serum factors.

Administration

Delivery of Constructs to Cells

The cells may be transfected in vivo, ex vivo or in vitro. The cells may be transfected as primary cells isolated from a patient or a cell line derived from primary cells, and are not necessarily autologous to the patient to whom the cells are ultimately administered. Following ex vivo or in vitro transfection, the cells may be implanted into a host. Genetic modification of the cells may be accomplished using one or more techniques well known in the gene therapy field (see, e.g., (1994) *Human Gene Therapy* 5:543-563).

Administration of a nucleic acid molecules provided herein to a target cell in vivo may be accomplished using any of a variety of techniques well known to those skilled in the art. The vectors of the herein may be administered orally, parentally, by inhalation spray, rectally, or topically in dosage unit formulations containing conventional pharmaceutically acceptable carriers, adjuvants, and vehicles. Suppositories for rectal administration of the drug can be prepared by mixing the drug with a suitable non-irritating excipient such as cocoa butter and polyethylene glycols that are solid at ordinary temperatures but liquid at the rectal temperature and therefore melt in the rectum and release the drug.

The dosage regimen for treating a disorder or a disease with the vectors and/or compositions provided is based on a variety of factors, including the type of disease, the age, weight, sex, medical condition of the patient, the severity of the condition, the route of administration, and the particular compound employed. Thus, the dosage regimen may vary widely, but can be determined empirically using standard methods.

The pharmaceutically active compounds (i.e., vectors or ligands) can be processed in accordance with conventional methods of pharmacy to produce medicinal agents for administration to patients, including humans and other mammals. For oral administration, the pharmaceutical composition may be in the form of, for example, a capsule, a tablet, a suspension, or liquid. The pharmaceutical composition is preferably made in the form of a dosage unit containing a given amount of DNA or viral vector particles (collectively referred to as "vector"). For example, these may contain an amount of vector from about $10^3$-$10^{15}$ viral vector particles, preferably from about $10^6$-$10^{12}$ viral particles. A suitable daily dose for a human or other mammal may vary widely depending on the condition of the patient and other factors, but, once again, can be determined using routine methods. The vector may also be administered by injection as a composition with suitable carriers including saline, dextrose, or water.

While the nucleic acids and/or vectors herein can be administered as the sole active pharmaceutical agent, they can also be used in combination with one or more vectors or other agents. When administered as a combination, the therapeutic agents can be formulated as separate compositions that are given at the same time or different times, or the therapeutic agents can be given as a single composition.

Ligands similarly may be delivered by any suitable mode of administration, including by oral, parenteral, intravenous, intramuscular and other known routes. Any known pharmaceutical formulations is contemplated.

Ligands

As noted, the ligands may be naturally-occurring ligands, but are preferentially non-natural ligands with which the LBD is modified to specifically interact. Methods for modifying the LBD are known, as are methods for screening for such ligands. Ligands include, non-natural ligands, hormones, anti-hormones, synthetic hormones, synthetic compounds or chemically modified naturally occurring compounds and other such compounds. Examples of synthetic ligands include, but are not limited to, the following: 1) LBB938 4-((1Z))-3-bicyclo[hept-2-yl-1- {4-[2-(dimethylamino)ethoxy]phenyl}-2-phenylprop-1-enyl)phenol; 2) LBB551 carbamic acid, [(2Z)-3-[4-[2-(dimethylamino) ethoxy]phenyl]-3-(4-hydroxyphenyl)-2-phenyl-2-propenyl]-, methyl ester; 3) LBC081 carbamic acid, [(2E)-3-[4-[2-(dimethylamino)ethoxy]phenyl]-3-(4-hydroxyphenyl)-2- phenyl-2-propenyl]-, methyl ester and 4) LBF580 4-((1E)-1-{4-[2-(dimethylamino)ethoxy]phenyl}-2-(4-morpholin-4-ylphenyl)prop-1-enyl)phenol.

Additional non-natural ligands include, in general, synthetic non-steroidal compounds, including synthetic derivatives of tamoxifen.

Pharmaceutical Compositions and Combinations

Also provided is a pharmaceutical composition containing a therapeutically effective amount of the fusion protein, or a nucleic acid molecule encoding the fusion protein in a pharmaceutically acceptable carrier. Pharmaceutical compositions containing one or more fusion proteins with different ligand binding domains are contemplated. Also provided are pharmaceutical compositions containing the expression cassettes, and also compositions containing the ligands. Combinations containing a plurality of compositions are also provided. Also provided are pharmaceutical compositions containing various ligands, including but not limited to synthetic ligands.

Preparation of the Compositions

The preparation of a pharmacological composition that contains active ingredients dissolved or dispersed therein is well known. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. Tablets and other solid forms are contemplated.

The active ingredient can be mixed with excipients that are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, as well as pH buffering agents and the like which enhance the effectiveness of the active ingredient.

The therapeutic pharmaceutical composition can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and others.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

Methods of Gene Regulation

Method of regulating expression of endogenous and exogenous genes are provided. In particular, ligand-dependent methods are provided.

In practicing the methods, a target nucleic acid molecule containing a sequence that interacts with the nucleic acid binding domain of the fusion protein is exposed to an effective amount of the fusion protein in the presence of an effective binding amount of a ligand, which can be added simultaneous with or subsequent to the fusion protein. The nucleic acid binding domain of the fusion protein binds to a portion of the target nucleic acid molecule and the ligand binds to the ligand binding domain of the fusion protein. Exposure can occur in vitro, in situ or in vivo.

Treatment

Methods for gene therapy are provided. The fusion proteins are administered either as a protein or as a nucleic acid encoding the protein and delivered to cells or tissues in a mammal, such as a human. The fusion protein is targeted either to a specific sequence in the genome (an endogenous gene) or to an exogenously added gene, which is administered as part of an expression cassette. Prior to, simultaneous with or subsequent to administration of the fusion protein, a ligand that specifically interacts with the LBD in the fusion protein is administered. In embodiments, in which the targeted gene is exogenous, the expression cassette, which can be present in a vector, is administered, simultaneous with or subsequent to administration of the fusion protein.

These methods are intended for treatment of any genetic disease, for treatment of acquired disease and any other conditions. Diseases include, cell proliferative disorders, such as cancer. Such therapy achieves its therapeutic effect by introduction of the fusion protein that includes the zinc finger-nucleotide binding polypeptide, either as the fusion or protein or encoded by a nucleic acid molecule that is expressed in the cells, into cells of animals having the disorder. Delivery of the fusion protein or nucleic acid molecule can be effected by any method known to those of skill in the art, including methods described herein. For example, it can be effected using a recombinant expression vector such as a chimeric virus or a colloidal dispersion system.

The fusion proteins provided herein can be used for treating a variety of disorders. For example the proteins can be used for treating malignancies of the various organ systems, including but are not limited to, lung, breast, lymphoid, gastrointestinal, and genito-urinary tract adenocarcinomas, and other malignancies such as most colon cancers, renal-cell carcinoma, prostate cancer, non-small cell carcinoma of the lung, cancer of the small intestine, and cancer of the esophagus. A polynucleotide encoding the zinc finger-nucleotide binding polypeptide is also useful in treating non-malignant cell-proliferative diseases such as psoriasis, pemphigus vulgaris, Behcet's syndrome, and lipid histiocytosis.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by, for example, Ausubel (ed.), *Current Protocols in Molecular Biology*, John Wiley and Sons, Inc. (1994); J. Sambrook and D. W. Russell,

*Molecular Cloning: A Laboratory Manual*, 3rd Ed., Cold Spring Harbor Laboratory, Cold Spring Harbor, N.Y. (2001); and by T. J. Silhavy, M. L. Berman, and L. W. Enquist, *Experiments with Gene Fusions*, Cold Spring Harbor Laboratory, Cold Spring Harbor, N.Y. (1984).

Example 1

Cell Based Reporter Assay

Ligand-dependent Regulation of Transgene Expression by ZFP-LBD Fusion Proteins

In order to evaluate the ability of the fusion proteins C7LBD A, B, and the related LBD mutants to regulate transgene expression, a standard co-transfection reporter assay was performed. A reporter construct, henceforth known as 6×2C7pGL3Luc, containing six copies of a directly repeated C7 binding site (6×2C7) inserted upstream of an SV40 promoter fragment and reporter gene encoding firefly luciferase (pGL3Pro; Promega) was transfected along with the designated fusion protein and assayed as described below. Note the consensus C7 binding site is 5'-GCG TGG GCG-3'.

Cultured cells (HeLa, Cos, Hep3B or other) were seeded at $5\times10^4$ cells/well in a 24 well plate prior to the day of transfection in DMEM Phenol-free media, supplemented with L-glutamine and 5% (v/v) charcoal-dextran stripped Fetal Bovine serum (sFBS). Cells were transfected using the Qiagen Superfect Transfection method. For each well 1 µg of total DNA, containing 0.5 µg luciferase reporter plasmid (6×2C7pGL3Luc), 0.1 µg of chimeric activator DNA (e.g., C7LBDA, C7LBDB, or mutants thereof), and 0.4 µg of an inert carrier plasmid DNA (p3Kpn), was mixed with 60 µL of DMEM phenol-free/serum free media, and 5 µL of Superfect reagent. In general, about 10 ng to about 0.5 µg of chimeric activator DNA was used for each well.

The mixture was vortexed for 10 seconds and incubated at room temperature for 10 minutes, followed by the addition of 350 µL of DMEM phenol-free 5% sFBS media. Cells were washed once with Dulbecco's phosphate buffered saline (DPBS) and the transfection mixture placed on the cells. Cells were washed once with DPBS following a 2.5 hour incubation at 37 degrees Celsius, and re-fed with DMEM Phenol-free 5% sFBS media.

At approximately 24 hours post-transfection, cells were treated with an inducing agent, such as the test compounds, 17 β-Estradiol or 4 OH-Tamoxifen as indicated, in a concentration range from 1 to 1000 nM final concentration in DMEM Phenol-free 5% sFBS. Cells were treated 24 hours later by washing once with DPBS and adding 200 µL 1X reporter lysis buffer (Promega). Plates were frozen at -80° C. and on the day of assay thawed at room temperature for 1.5 hours on an orbital shaker at 100 RPM. After allowing for cellular debris to settle, lysate was transferred to a new tube, diluted 1:10 with 1X reporter lysis buffer and 10 µL transferred to 96 well opaque plates. The luciferase assay was performed as per the manufacturers suggestions (Promega) and the plates were analyzed with a Tropix TR717 Microplate Luminometer.

Example 2

Adenoviral Vectors

Construction and Evaluation of the $Cys_2$-$His_2$ Zinc Finger DBD-ER LBD Regulators in Adenoviral Vectors To deliver the two components of the regulatory system to mammalian cells, either ex vivo or in vivo, a series of adenoviral vectors were constructed. These vectors contained either the ZFP-LBD fusion protein regulator linked to the immediate early CMV promoter or the regulatable transgene, linked to the 6×2C7 array of C7 binding sites and the minimal promoter from SV40 or c-fos TATA as described previously. The fusion protein regulator vector and regulatable transgene vector are then mixed at various ratios and delivered to cells or animals by standard methods. The methods described here can be used to construct and evaluate any of the mutated LBD variants that are the subject of this application.

Construction of an adenovirus vector is routine and generally, the procedure involves three main steps: first a shuttle plasmid containing the viral left ITR, viral packaging signal, a promoter element, a transgene of interest linked to the promoter element and followed by a poly adenylation sequence, and some additional DNA sequences, viral or non-viral, required for recombination is prepared. Second, this left end shuttle plasmid, along with the remainder of the viral genome (i.e. the right end of the vector) are transfected into a host cell and joined through DNA recombination to form a complete vector genome. This recombination step may result from sequence homology between the two vector halves or may be aided by the use of site specific recombinases such as Cre and their corresponding LoxP recombination sequences. Finally, the newly formed virus is amplified up and purified in a series of steps. The details of the construction of these vectors are briefly described below.

Left End Shuttle Plasmid Construction for ZFP-LBD Fusion Protein Regulators

Figure 7:
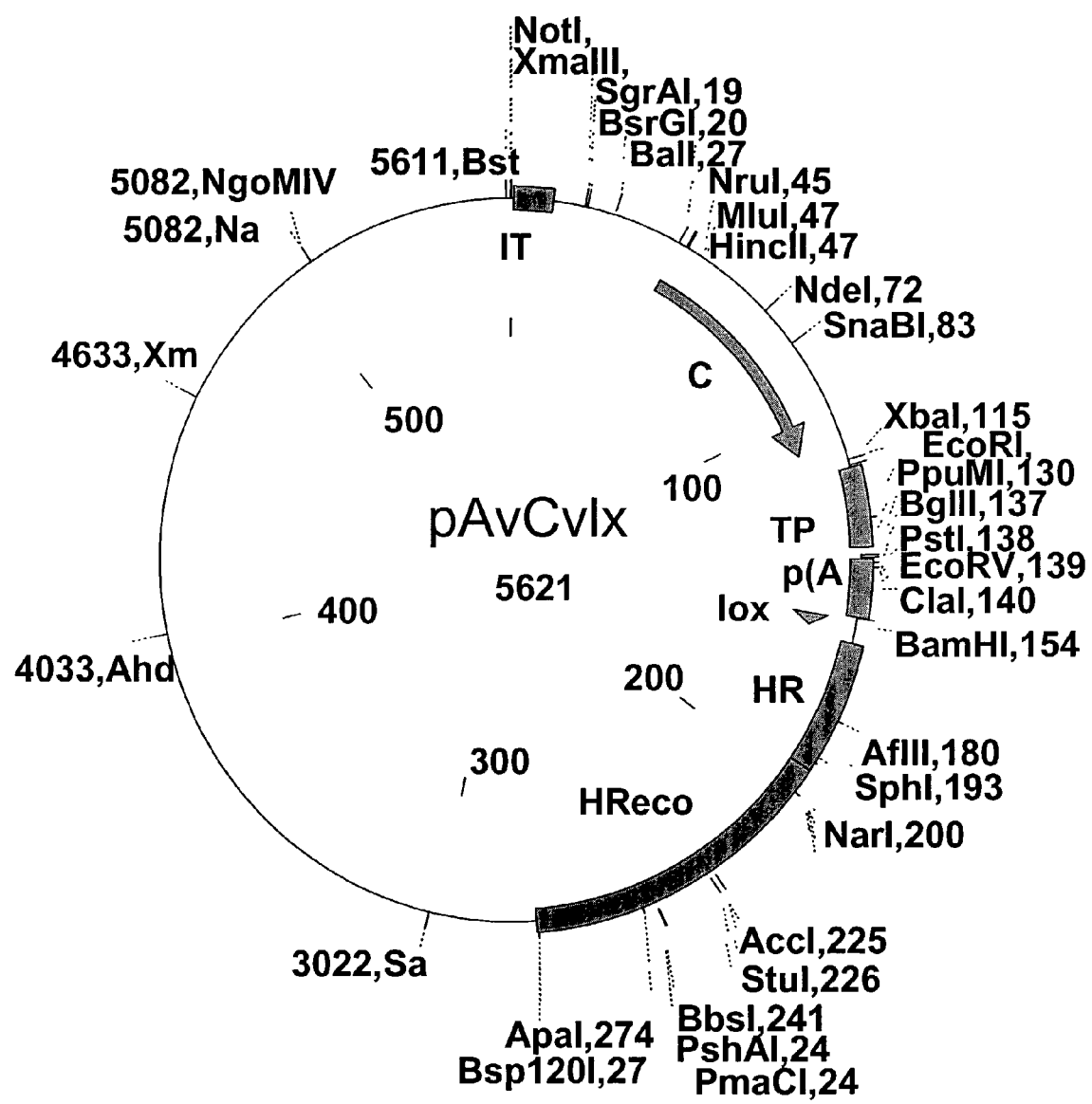
FIG. 7 shows a restriction map for the plasmid designated pAvCVLx. This is a "left end" shuttle plasmid for adenovirus vector construction.

Shuttle plasmids containing the left viral ITR, CMV immediate early promoter and ZFP-LBD regulator were prepared in the plasmid pAvCV1x. See FIG. 7. Note that this vector contains a loxP recombination site just downstream of the poly adenylation sequence. DNA encoding the intact reading frame for the chimeric regulators C7LBD Bs(G521R), C7LBD Bs(388V-424Y-428A), C7LBD Bs(524G) and C7LBD Bs(421V-428A) were excised from the appropriate pCDNA constructions by digestion with restriction enzymes EcoRI and Not I. The ZFP-LBD DNA fragments were modified with Klenow to fill in the restriction site overhangs and blunt end ligated into the EcoRV at bp 1393 site of pAvCv1x to generate pAvCv-C7LBD Bs(G521R), pAvCv- C7LBD Bs(388V-424Y-428A), pAvCv-C7LBD Bs(524G) and pAvCv-C7LBD Bs(421V-428A).

Construction of Left End Shuttle Plasmids Containing Regulatable Transgene Cassettes Regulatable transgene cassettes were prepared containing the 6×2C7 binding sites and SV40 minimal promoter fragment linked to the Luciferase transgene as in pGL3 6×2C7-Luc (described in previous example).

These vectors were constructed in two steps. First, a fragment containing the CMV promoter and tripartite leader sequence (TPL) of pAvCvlx (FIG. 7) was excised by digestion with MulI and BglII, which cut at bp 473 and 1375 respectively. The restriction site overhangs were filled in with Klenow. Blunt ended DNA fragments containing the 6×2C7-SV40 enhancer/promoter regions of the previously described reporter plasmid was ligated into this backbone to create the pAV-6×2C7SV40 shuttle plasmid. Next, a DNA fragment containing the Luciferase transgenes was ligated into the EcoRV site of the shuttle plasmids to create pAv6×2C7SV40-Luc (lox).

Construction of a Right End Vector Plasmid

Figure 8:
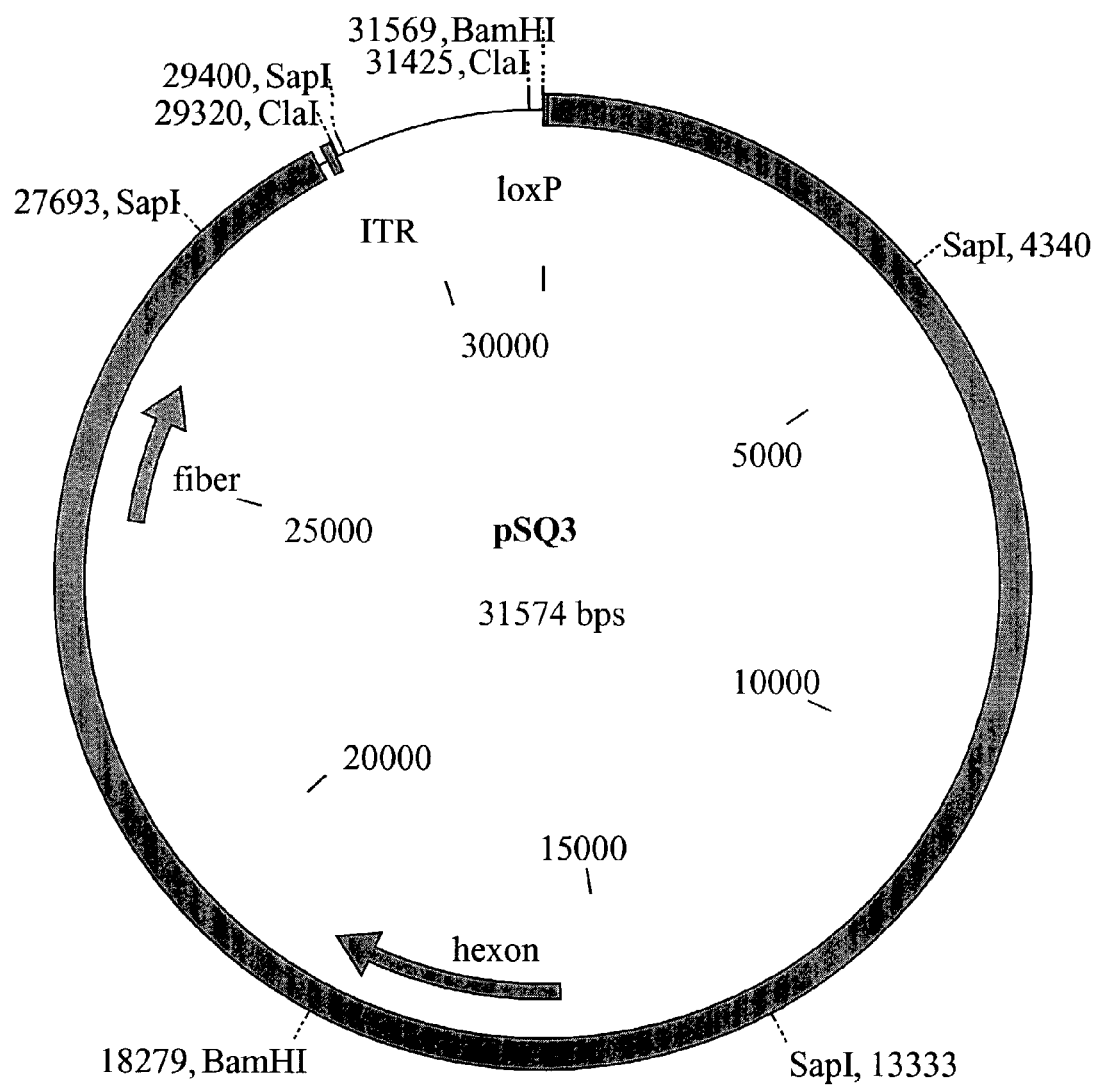
FIG. 8 shows a restriction map for the plasmid designated pSQ3. This is a "right end" shuttle plasmid for adenovirus vector construction.

To complete the vector construction, a plasmid containing the remainder of the viral vector genome is required. This plasmid, referred to as pSQ3 (FIG. 8), contains a pBR322- derived backbone, ampicillin resistance gene and the adenovirus serotype 5 genome, beginning at Ad5 bp 3329, through the right ITR, with deletions in the E2a and E3 region as described previously (Gorziglia et al. (1996) *J. Virol.* 70:4173-4178). In addition, this plasmid has two important features, a loxP site inserted at the Bam HI site (bp 31569) just upstream of the Ad5 sequences, and a Cla I site at the end of the viral 5' ITR. This Cla I site is used to linearize the plasmid and expose the right ITR during vector construction.

Vector Assembly and Propagation

Adenoviral vectors encoding fusion protein regulators, Av3CV-C7LBDBS(G521R), Av3CV-C7LBDBS(524G), Av3CV-C7LBDBS(388V-424Y-428A) and Av3CV-C7LBDBS(421V-428A) and the vector containing a regulatable luciferase transgene, Av3SV-LUC were constructed. Each vector was generated by a standard procedure. Briefly, for each vector construct, three plasmids, pSQ3 (pre digested with ClaI), the appropriate left end shuttle plasmid (e.g. pAvCv-C7LBD Bs(G521R), or pAv6×2C7SV40-Luc (lox), pre-digested with NotI and Afl II, and an expression plasmid for the Cre recombinase, pCMV-CRE, were cotransfected at a weight ratio of 3:1:1 into dexamethasone induced AE1-2a cells (Gorziglia et al.) using Promega's Profection Kit. About 1 week after transfection, cells were harvested and lysed by 4 cycles of freeze/thaw. The resulting cell lysate was passed onto fresh dexamethasone induced AE1-2a cells and the culture maintained about a week until cytopathic effect (CPE) was observed. This process was repeated several cycles until sufficient material was obtained to purify the vector by CsCl equilibrium density centrifugation. Once purified, vectors are quantitated by lysing in buffer containing 10 nM Tris, 1 mM EDTA, 0.1% SDS for 15 minutes at 56° C., cooling and reading the absorbance at 260 nm wavelength (OD260). The OD260 reading is converted to a virus particle concentration using 1 OD260 unit=$1.1\times10^{12}$ particles/ml.

Results

In vitro Regulation with Adenovirus Vectors

The ability to regulate expression of a transgene delivered by an adenovirus vector was demonstrated by the following experiment. HeLa cells were infected with a mixture of two adenovirus vectors, one containing a fusion protein regulator (e.g. Av3-C7LBD-B(G521R), the other containing the 6×2C7SV40-luc cassette. The two vectors were used at a dose of 50 vector particles per cell and 250 vector particles per cell of the transgene and regulator vectors respectively. Twenty four hours after vector transduction, the cells were treated where appropriate with 100 nM of the test compound. Following an additional 24 hrs incubation, the cells were lysed and assayed for luciferase activity as previously described. The results of this experiment are summarized in FIG. 5.

These data indicate that all three mutant LBD and novel compound combinations tested were able to stimulate luciferase reporter gene activity in a drug-dependent manner. Although response of the 421V-428A mutant to LBC081 was a modest 3 fold induction, both 388V-424Y-428A and 524G responded to their respective compounds with induction levels comparable to that obtained with 4-OHT on the G521R mutant.

Conclusions

These in vitro results demonstrate that the ZFP-LBD fusion proteins can be efficiently delivered via an adenovirus vector and can be expressed in sufficient amounts to provide drug-dependent control of a transgene in cells. Furthermore, the data show that the basal level of expression from the 6×2C7-minimal promoter constructs tested in an adenovirus vector give relatively low levels of expression, even when the fusion protein is expressed in the same cell.

Example 3

Lentiviral Vectors

Construction and Evaluation of the $Cys_2$-$His_2$ Zinc Finger DBD-ERLBD Regulators in Lentiviral Vectors In order to demonstrate controlled gene expression in an integrated vector system, a regulatory system (e.g. C7LBD-As(G521R) similar to that described in the previous adenoviral vector example (Example 2) can be used to develop a series of lentiviral vectors. These vectors preferably contain either the ZFP-LBD fusion protein linked to the immediate early CMV promoter or a regulatable transgene (either eGFP or luciferase) linked to the 6×2C7 array of C7 binding sites and either the minimal promoter from SV40 or the C-fos gene minimal TATA box region. The fusion protein-encoding vector and the regulatable transgene vector can then be used to generate lentiviral vector supernatant. The supernatant can be used to stably transduced human cells either singly or in parallel. Stable cell lines containing the integrated vectors can then be induced with the appropriate activating drug (e.g., 4-OH-tamoxifen) and gene expression is measured as fold induction in the presence and absence of drug.

Construction of Lentiviral Vectors Encoding the ZFP-LBD Fusion Protein or the Regulatable Transgene.

The generation of lentiviral vectors and vector supernatant involves 3 main steps: first a gene or region of interest is inserted into shuttle vector backbone plasmid containing all of the viral cis-elements for transcription, packaging, reverse transcription, and integration. Second, the lentiviral vector shuttle plasmid is co-transfected into human 293 cells along with plasmids providing the packaging functions (gag, pol, and env). Typically the transfections include 10 μg of vector plasmid, 10 μg of packaging plasmid and 1 μg envelope plasmid (Vesicular Stomatitis virus G envelope) using a Profection Calcium Phosphate transfection kit. Third, the culture supernatant containing the lentiviral vector is harvested (between 24 and 48 hours post transfection) and used to transduce naïve human target cells.

Construction of HIV-1 Based Vectors

An HIV-1-based vector system containing an internal CMV promoter was constructed from an infectious HIV-$1_{IIIB}$ provirus cDNA (pHIV-IIIB) The infectious proviral cDNA was generated by PCR from DNA isolated from H-9 cells chronically infected with HIV-$1_{IIIB}$. The gag/pol and env sequences of pHIVIIIB were removed by digestion and excision of a PstI-KpnI fragment. Replacing the gag/pol and env sequences was a PstI/Kpn polylinker containing unique multiple cloning sites to form the intermediate vector p2XLTR. The Rev response element (RRE) fragment from HIVIIIB, required for proper vector RNA processing, was inserted downstream of the truncated gag sequences of p2XTR to form the construct pHIVec. An AseI-XbaI CMV-eGFP reporter fragment derived from pEGFP-N1 (Clontech, Palo Alto, Calif. ) was cloned into the NdeI-Xba site of pHIVec to generate pHIVCMVGFP. pHIVCMV-X was generated by removal of the eGFP fragment by KpnI digestion and religation.

Construction of pHIVCMV-C7LBD/A(G521R)

The C7LBD/A(G521R) coding fragment is excised from the appropriate expression plasmid by restriction digestion and cloned into pHIVCMV-X downstream of the CMV promoter. As a control for induction, an HIV vector containing a constitutive transactivator and DBD chimera is generated, pHIVCMV-C7VP16. A HindIII-NotI restriction fragment from pCDNA3-C7VP16 containing the C7VP16 coding fragment is inserted downstream of the CMV promoter at the Sma site of pHIVecCMV-X.

Construction of pHIV6×2C7Sv and pHIV6×2C7TATA Luciferase Vectors

A BamHI-XbaI restriction fragment containing the 6×2C7TATA luciferase fragment is isolated from pTATA6× 2C7Luc and cloned downstream of the RRE at the SpeI-XbaI restriction sites. A MluI-BstBI restriction fragment containing the 6×2C7Sv luciferase fragment is isolated from pGL3-6×2C7SvLuc and cloned downstream of the RRE at the Spe-XbaI restriction sites.

Evaluation of the ZFP-LBD Fusion Proteins and Regulatable Lentiviral Vectors Transduction of HeLa Cells by Inducible Lentiviral Vectors Subconfluent HeLa cells are transduced with either HIV6×2C7SvLuc or HIV6×2C7TATALuc vector supernatant for 24 hours followed by transduction with HIVAS521R lentiviral vector supernatant. Cells are allowed to recover from infection for 24 hours in fresh culture medium after which 4-OH-tamoxifen (100 or 1000 nM) was added to the culture for an additional 24 hours. Cells were lysed in a standard luciferase lysis buffer, subjected to freeze thaw and analyzed for luciferase activity using a luciferase assay kit (Promega). The results show that cells infected with either HIV6×2C7SvLuc or HIV6×2C7TATALuc followed by transduction with HIVCMVAS521R resulted in a 13.1 and 11.7 fold stimulation in luciferase activity respectively, when given 4-OH-tamoxifen.

Lentiviral Transduction of Lentiviral Integrated Target Vector Populations

HeLa cells that had been previously transduced with either HIV6×2C7SvLuc or HIV6×2C7TATALuc are carried in culture for 9 passages without exposure to any ZFP-LBD fusion protein. On passage 10, cells are transduced with HIVCMVAS521R for 24 hours followed by the addition of 100 nM tamoxifen for an additional 24 hours. The results show that the transgene within an integrated HIV6× 2C7SvLuc or HIV6×2C7TATALuc vector can be upregulated by C7LBD-As(G521R) in a tamoxifen-dependent manner. Induction of the integrated HIV6×2C7SvLuc or HIV6×2C7TATALuc vectors is 31.4- and 22.5-fold, respectively. These data demonstrate the effectiveness of the C2H2-LBD regulator for controlling expression of a transgene that is stably integrated into the host cell chromosome.

Example 4

Modifications of the Estrogen Receptor Ligand Binding Domain Improve Ligand Selectivity Modification of certain amino acid residues within the estrogen receptor ligand binding domain can enable selective activation of the receptor by synthetic ligands. The structure-activity relationship (SAR) for wild-type ER interaction with estradiol is relatively well known and allows one to design modifications to reduce or eliminate estradiol activity on the modified receptor. For example, a single point mutation of ER residue 521 from glycine to arginine has been described which dramatically decreases the binding affinity of estradiol to wt ER, but this mutation has little effect on the binding of the synthetic anti-estrogen 4-hydroxytamoxifen (4-OHT) [Danielian, P. S., White, R., Hoare, S. A., Fawell, S. E. and Parker, M. G. (1993). Identification of Residues in the estrogen receptor that confer differential sensitivity to estrogen and hydroxytamoxifen. Mol. Endo. 7: 232-240.]

Likewise, the mutation of the ER residue 400 from glycine to valine significantly reduces the responsiveness of the wt ER to estradiol, but this mutation has little effect on 4-OHT binding [Tora, L., Mullick, A., Metzger, D., Ponglikitmongkol, M., Park, I., Chambon, P. (1989). The cloned human oestrogen receptor contains a mutation which alters its hormone binding properties. Embo J., 8: 1981-1986.] Finally, a single point mutation of ER M421 also reduces the receptor's response to estradiol (N Miller & J Whelan, J. Steroid Biochem. Molec. Biol. 64:129-135, 1998).

More recently, the availability of X-ray crystal structures describing the ER LBD complexed with the agonist estradiol or antagonists raloxifen or tamoxifen [Andrzej M. Brzozowski et al. Molecular basis of agonism and antagonism in the estrogen receptor, Nature 1997 389:753-758; Andrew K. Shiau, Danielle Barstad, Paula M. Loria, Lin Cheng, Peter J. Kushner, David A. Agard, and Geoffrey L. Greene. The Structural Basis of Estrogen Receptor/Coactivator Recognition and the Antagonism of This Interaction by Tamoxifen, Cell 1998 95: 927.] have greatly added to our molecular understanding of the ligand-receptor interactions. Given both the structural information and the SAR of ER-LBD interaction with steroids and nonsteroids, sufficient information is now available to enable the design of novel synthetic compounds with high selectivity for a specifically modified receptor LBD (Tedesco et al., Chemistry & Biology, 2001, 8:277-287).

Region 1 Modifications

Through analysis of the ER-tamoxifen and ER-estradiol co-crystal structures (refs as above), several regions within the ER LBD amenable to concomitant protein and ligand modifications were identified. The first region, referred to here as Region 1 (R1) is broadly defined as the area adjacent or proximal to the ethyl side chain of tamoxifen. More particularly, Region 1 is comprised of those amino acids within the ER ligand binding domain, any portion of which come within approximately 9 angstroms of the terminal carbon of the ethyl side chain of 4-OH-Tam, also known as position C10 in 4-OH-Tam. The key residues within Region 1 include but are not limited to M388, L391, M421, 1424, and L428. In general, residues within Region 1 were modified to smaller amino acid side chains in order to make space for bulky substituents added to the ethyl side chain of tamoxifen.

In one example, oligonucleotide-mediated site directed mutagenesis was performed (Stratagene; Quikchange Site-Directed Mutagenesis Kit) on plasmids encoding the fusion proteins ER-LBD-C7LBDa and C7LBDb to substitute valine for methionine at residue 421 and alanine for leucine at residue 428. The sequences of the oligonucleotides used for 421V/428A mutagenesis were:

GTAGAGGGCGTGGTGGAGATCTTCGACATG GCCCTGGCTACATC (SEQ ID NO: 17) for the coding strand and GATGTAGCCAGGGCCATGTCGAAGATCTCCAC CACGCCCTCTAC (SEQ ID NO: 18) for the noncoding strand, where the nucleotide underlined in bold represents the change from the wild-type sequence.

Templates were added at 10 ng to 50 ng per reaction with 125 ng of each primer in 10 M KCl, 10 mM $(NH_4)_2SO_4$, 20 mM Tris-HCl (pH 8.8), 2mM $MgSO_4$, 0.1% Triton X-100, 0.1. mg/ml BSA, dNTP mix, and 2.5U Pfu Turbo™ DNA polymerase. The reactions were carried out on a Perkin Elmer GeneAmp PCR system 9600 thermal-cycle using an initial temperature of 94 degrees Celsius for 30 seconds to denature the template, followed by 15 cycles at 95 degrees Celsius for 30 seconds, 53 degrees Celsius for 1 minute, and 68 degrees Celsius for 6 minutes, with a single round of extension at 72 degrees Celsius for 2.5 minutes. PCR samples were treated with 10U DpnI for 1 hr at 37 degrees Celsius to digest the non-mutagenized parent template.

DH5α supercompetent Epicurean Coli® XL-1 cells were transformed by combining 1 µL of the DpnI treated PCR samples with 50 µL of the cells in chilled Falcon 2059 tubes, incubated on ice for 30 minutes, heat shocked at 42 degrees Celsius for 45 seconds and chilled on ice for 2 minutes. A 500 µL aliquot of SOC media pre-warmed to 42 degrees Celsius was added to the transformation reaction and incubated for 1 hour at 37 degrees Celsius with shaking. The transformed cells were plated onto LB plates containing 100 µg/ml ampicillin and incubated for at least 16 hours.

In another example, a collection of Region 1 mutations were made by combining modifications at residues 388, 424 and 428. The ER-LBD 388/424/428 mutant collection was constructed by first selecting for plasmid DNA clones mutated to contain either valine or alanine at residue 428. Using 428A and 428V as templates, residues of varying size and hydrophobicity were substituted for the native M388 and I424 residues. Methionine 388 was replaced with either valine (V or Val), alanine (A or Ala), Phenylalanine (F or Phe) or tryptophan (W or Trp); Isoleucine 424 was replaced with either alanine, methionine (M or Met) or phenylalanine (F or Phe). Specific oligonucleotide primers were designed to incorporate the mutants. The sequences of these oligonucleotide primers are listed in Table 5. The sequence of the oligonucleotides used to obtain one particularly interesting mutant ER-LBD388V/424Y/428A are cited here:

GCTAGAGATCCTGGTGATTGGTCTCGTC for 388V (SEQ ID NO:19),

GGCATGGTGGAGTACTTCGACATGGCC for 424Y (SEQ ID NO:20) and

GATCTTCGACATGGCCCTGGCTACATCATC for 428A. (SEQ ID NO:21)

Amino acids at 388 and 424 were substituted simultaneously using in vitro Site-Directed Mutagenesis System (Promega GeneEditor™ kit) as follows. Templates were added at 0.2 µg per reaction with 0.25 pmol Selection oligonucleotide and 1.25 pmol each mutagenic oligonucleotide in 200 mM Tris-HCl (pH 7.5), 100 mM $MgCl_2$, 500 mM NaCl, 10 u T4 DNA polymerase and 3 u T4 DNA ligase. The mutant strand synthesis and ligation were carried out at 37 degrees Celsius for 90 minutes.

BMH71-18 muts cells were transformed by combining 1.5 µL mutagenesis reaction with 100 µL of the cells in chilled Falcon 2059 tubes, incubated on ice for 10 minutes, heat shocked at 42 degrees Celsius for 45 seconds and chilled on ice for 2 minutes. A 900 µL aliquot of SOC media pre-warmed to 42 degrees Celsius was added to the transformation reaction and incubated for 1 hour at 37 degrees Celsius with shaking. Mutation efficiency is enhanced by the initial transformation into the BMH cells (Promega GeneEditor User's Manual). DNA was isolated using Qiagen mini prep column and 10 ng DNA was used to transform JM109 cells in GeneEditor Antibiotic Selection Mix to isolate the mutants. The transformed cells were plated onto LB plates containing 100 µg/ml ampicillin and incubated for at least 16 hours. DNA was isolated and sequenced to confirm the mutation.

The first round mutants were then tested for their activation by a series of ethyl sidechain-modified 4-OHT derivatives using a cell-based reporter gene assay as described in example 1. The SAR of this mutant collection suggested that small amino acid sidechains at positions 388 and 428 and a larger sidechain at residue 424 were preferred for activation by the test compounds. To further optimize the drug activity and specificity, a second round of mutagenesis was carried out. Beginning with plasmids containing 388V/428A or 388A/428A, various amino acids containing polar and bulky sidechains, specifically Phe, Leu, Met, Val and Tyr, were substituted at residue 424. In addition, these same substitutions at 424 were also made in the context of 421V/428A in order to compare the activation pattern in these two mutant collections. The mutagenesis reaction was carried out using PCR-based oligonucleotide mediated site directed mutagenesis as described above (Stratagene; Quikchange Site-Directed Mutagenesis Kit). The sequences of the oligonucleotide primers used to modify residue 424 are listed in Table 6.

TABLE 5

Sequences of oligonucleotide primers used in mutation of ER-LBD 388 and 424 sites

| Mutants | Coding strand |
|---------|---------------|
| 424A/428V | GGCATGGTGGAGGCCTTCGACATGGTGC (SEQ ID NO:22) |
| 424F/428V | GGCATGGTGGAGTTC TTCGACATGGTGC (SEQ ID NO:23) |
| 424M/428V | GGCATGGTGGAGATG TTCGACATGGTGC (SEQ ID NO:24) |
| 424A/428A | GGCATGGTGGAGGCCTTCGACATGGCCC (SEQ ID NO:25) |
| 424F/428A | GGCATGGTGGAGTTC TTCGACATGGCCC (SEQ ID NO:26) |
| 424M/428A | GGCATGGTGGAGATG TTCGACATGGCCC (SEQ ID NO:27) |
| 388A | GCTAGAGATCCTGGCCATTGGTCTCGTC (SEQ ID NO:28) |
| 388F | GCTAGAGATCCTGTTC ATTGGTCTCGTC (SEQ ID NO:29) |
| 388V | GCTAGAGATCCTGGTG ATTGGTCTCGTC (SEQ ID NO:30) |
| 388W | GCTAGAGATCCTGTGG ATTGGTCTCGTC (SEQ ID NO:31) |

TABLE 6

Sequences of oligonucleotide primers used in mutation of ER-LBD 424

| Mutants | Coding strand | Noncoding strand |
|---------|---------------|------------------|
| 424 permutation in the context of either 388A/428A or 388V/428A | | |
| 424F/428A | GGCATGGTGGAGTTCTTCG ACATGGCC (SEQ ID NO:32) | GGCCATGTCGAAGAACTCC ACCATGCC (SEQ ID NO:33) |

TABLE 6-continued

Sequences of oligonucleotide primers used in mutation of ER-LBD 424

| Mutants | Coding strand | Noncoding strand |
|---|---|---|
| 424L/428A | GGCATGGTGGAGCTGTTCG ACATGGCC (SEQ ID NO:34) | GGCCATGTCGAACAGCTCC ACCATGCC (SEQ ID NO:35) |
| 424M/428A | GGCATGGTGGAGATGTTCG ACATGGCC (SEQ ID NO:36) | GGCCATGTCGAACATCTCC ACCATGCC (SEQ ID NO:37) |
| 424V/428A | GGCATGGTGGAGGTGTTCG ACATGGCC (SEQ ID NO:38) | GGCCATGTCGAACACCTCC ACCATGCC (SEQ ID NO:39) |
| 424Y/428A | GGCATGGTGGAGTACTTCG ACATGGCC (SEQ ID NO:40) | GGCCATGTCGAAGTACTCC ACCATGCC (SEQ ID NO:41) |

424 permutation in the context of 421V/428A

| 421V/424F/ 428A | GGCGTGGTGGAGTTCTTCG ACATGGCC (SEQ ID NO:42) | GGCCATGTCGAAGAACTCC ACACGCC (SEQ ID NO:43) |
| 421V/424L/ 428A | GGCGTGGTGGAGCTGTTCG ACATGGCC (SEQ ID NO:44) | GGCCATGTCGAACAGCTCC ACCACGCC (SEQ ID NO:45) |
| 421V/424M/ 428A | GGCGTGGTGGAGATGTTCG ACATGGCC (SEQ ID NO:46) | GGCCATGTCGAACATCTCC ACCACGCC (SEQ ID NO:47) |
| 421V/424V/ 428A | GGCGTGGTGGAGGTGTTCG ACATGGCC (SEQ ID NO:48) | GGCCATGTCGAACACCTCC ACCACGCC (SEQ ID NO:49) |
| 421V/424Y/ 428A | GGCGTGGTGGAGTACTTCG ACATGGCC (SEQ ID NO:50) | GGCCATGTCGAAGTACTCC ACCACGCC (SEQ ID NO:51) |

Mutants were named with amino acid number followed by the substituted residue. Val or V = valine, Ala or A = alanine, Leu or L = leucine, Phe or F = phenylalanine, Trp or W = tryptophan, Met or M = methionine, Tyr or Y = tyrosine. Size of amino acid sidechain = Ala < Val < Met < Phe < Tyr < Trp. Letters underlined in bold represent mutated nucleotides.

Region 2 Modifications

A second region of the ER LBD suitable for modification is broadly defined as the area proximal to the D ring of estradiol. More particularly, this region, referred to here as Region 2, is comprised of those amino acids within the ER ligand binding domain, any portion of which come within approximately 9 angstroms of the para position carbon in the ring of 4-OH-Tam that corresponds to the D-ring of estrogen, also known as position C14 in 4-OH-Tam. Region 2 includes but is not limited to a histidine at residue 524 and a glycine at position 521. Based on protein crystal images, modifications at the para-position of the estradiol D ring, or the para-position of the ring within tamoxifen that resides in the D ring position will directly impinge on residue H524. Previous studies have identified the importance of H524 for estrogen activity on ER (Kirk Ekena et al, 1996, J. Biol Chem, 271: 20053-59). However, in a preferred embodiment, our application involves two additional parameters unavailable from the previous studies: the mutant is preferably activated by a synthetic ligand, and the synthetic ligand is preferably weak or inactive on wild-type ER.

Mutant H524G and Ligand LBF580

In another example, oligonucleotide-mediated site directed mutagenesis was performed as described above (Stratagene; Quikchange Site-Directed Mutagenesis Kit) on plasmids encoding the fusion proteins ER-LBD-C7LBDa and C7LBDb to substitute either alanine or glycine for histidine at residue 524.

The sequence of the oligonucleotides used for the H524G modification were GCATGGAG GGCCTGTACAGCATGAAG (SEQ ID NO:52) for the coding strand and CTTCATGCTGTACAG GCCCTCCATGC (SEQ ID NO:53) for the noncoding strand. Mutated plasmids were isolated and their sequence confirmed. The function of the new mutants was evaluated using a cell-based reporter gene assay as described in Example 1. In an assay looking at fold induction at 10 nM, the compound LBF 580 was highly active on the H524G mutant but very weak on the H524A mutant with a ratio of fold activation of 138 to 4. This indicated a highly selective interaction between 524G and LBF580. Furthermore, LBF580 is very weak on wt ER, having an IC50 of nearly 300 nM. Since the 524G mutant can be induced 140 fold by just 10 nM of LBF580 (FIG. 6), this combination can be used under conditions where the compound will be inactive on wt ER. Finally, though 524G is moderately induced (16 fold) by 10 nM estradiol (FIG. 6), the response at physiologic levels of 0.3 nM should be insignificant and not limit the potential of this mutant receptor for in vivo applications.

TABLE 7

SEQ ID NO's for wild-type and mutant C7LBD constructs:

For C7LBDAS;

1) C7LBDAS (wt), Nucleic acid sequence (SEQ ID NO:1), Amino acid sequence (SEQ ID NO:2)
2) C7LBDAS 388V/424Y/428A, Nucleic acid sequence (SEQ ID NO:5), Amino acid sequence (SEQ ID NO:6)
3) C7LBDAS 421V/428A, Nucleic acid sequence (SEQ ID NO:7), Amino acid sequence (SEQ ID NO:8)
4) C7LBDAS H524G, Nucleic acid sequence (SEQ ID NO:9), Amino acid sequence (SEQ ID NO:10)

For C7LBDBS:

5) C7LBDBS (wt), Nucleic acid sequence (SEQ ID NO:3), Amino acid sequence (SEQ ID NO:4)
6) C7LBDBS 388V/424Y/428A, Nucleic acid sequence (SEQ ID NO:11), Amino acid sequence (SEQ ID NO:12)
7) C7LBDBS 421V/428A, Nucleic acid sequence (SEQ ID NO:13), Amino acid sequence (SEQ ID NO:14)
8) C7LBDBS H524G, Nucleic acid sequence (SEQ ID NO:15), Amino acid sequence (SEQ ID NO:16).

Example 5

Drug Activity on Wild-type ER (pHEGO)

Reagents

Wild-type ER plasmid (pHEGO) (accession number M12674 (SEQ ID NO:54 and SEQ ID NO:55), incorporated herein by reference) was obtained from P. Chambow's lab, Strasbourg, France. SuperFect and phenol-free DMEM were obtained from Qiagen Inc. (Valencia, Calif.) and Biowhittaker (Walkersville, Md.) respectively. Luciferase assay kit was from Promega and the luminescence was quantitated by Luminometer (Tropix, Bedford, Mass.). Test compounds were synthesized in house.

Methods

Inhibition of $E_2$-induced activation by selected compounds COS-7 cells were plated at $5\times10^4$ cells/well in 24 well plates the day before transfection, and refed with phenol-free DMEM supplemented with 5% stripped FBS and L-glutamine (hereafter referred to as steroid-free media). For transfection, 0.5 microgram of pERE2tkluc reporter plasmid, 20 ng of pHEGO, and 0.5 microgram of pCIneo inert carrier DNA were combined with 60 microliter serum-free DMEM and 5 microliter Qiagen Superfect transfection reagent, vortexed for 10s, and set at room temperature for 10 min. Each sample was diluted with 350 microliters of steroid-free media, mixed, and added to each well. Following 2 hr 30 min incubation at 37° C., cells were washed once with Dulbecco's phosphate buffered saline (DPBS), and refed with steroid-free media. Approximately 24 hr posttransfection, cells were treated with varying concentrations of tamoxifen, 3 nM $E_2$ and/or the appropriate test compounds at 0.1 nM to 1000 nM final concentration. Approximately 24 hr after treatment, cells were washed once with DPBS, then 200 microliter of reporter lysis buffer was added per well and frozen at $-80°$ C. Cells were thawed at room temperature on an orbital shaker for 1 hr 30 min. A 10 microliter aliquot of lysate was transferred to 96 well opaque plates, and relative luciferase units (RLU) determined on a luminometer using the appropriate firefly luciferase substrate.

To determine percent inhibition of $E_2$-induced activation by the various test compounds, the following formula was used:

$$\% \text{ inhibition} = \frac{T - RLU \text{ at specific dose of test compound}}{\text{specific activity}}$$

where T is the maximal activity in RLU at 3nM $E_2$, and specific activity is T—nonspecific activity (RLU at 1000 nM tamoxifen in the presence of 3 nM $E_2$). Note that the nonspecific activity is a noncompetable element in the assay system.

Preparation of test compounds R1 compounds were dissolved in DMSO to make 10 mM stocks. In order to dissolve them completely, all the solutions were warmed in 55° C. or boiled water bath for 10 to 20 min before use. The DMSO in cell culture medium was maintained to 0.01% for all the drug concentration tested as well as the vehicle control.

Calculation of EC50 and IC50 by tamoxifen Nonlinear curve fitting was performed by using Graph Pad Prism (Graph Pad Software, Inc., San Diego, Calif.) to determine the values of EC50 and IC50.

Example 6.

Gutless Adenoviral Vectors

Construction of the $Cys_2$-$His_2$ Zinc Finger DBD-ER LBD Regulators in "Gutless" Adenoviral Vectors To efficiently deliver the two components of the regulatory system to mammalian cells, either ex vivo or in vivo, a series of gutless adenoviral vectors were constructed. These vectors are similar to those described previously (Example 2), and contain either the ZFP-LBD fusion protein regulator linked to the immediate early CMV promoter or the regulatable transgene, linked to the 6×2C7 array of C7 binding sites and the minimal promoter from SV40 TATA. The fusion protein regulator vector and regulatable transgene vector are then mixed at various ratios and delivered to cells or animals by standard methods.

Gutless adenoviral vectors are devoid of adenoviral coding regions and contain only the essential adenovirus packaging signals, ITRs, and the transgene expression cassette(s). Gutless adenoviral vectors have been demonstrated to be improved over first generation vectors with respect to an increased duration of transgene expression in mice (Schiedner et al., "Genomic DNA transfer with a high capacity adenovirus vector results in improved in vivo gene expression and decreased toxicity" *Nature Genetics* 18: 180-183 (1998); Morral et al., "High doses of a helper-dependent adenoviral vector yields supraphysiological levels of alpha-1-antitrypsin with negligible toxicity" *Hum. Gene Ther.* 9: 2709-2713 (1998); Reddy et al., "Sustained human factor VIII expression in hemophilia A mice following systemic delivery of a gutless adenoviral vector" *Mol. Ther.* 5: 63-73 (2002)) and non-human primates (Morral et al., "Administration of helper-dependent adenoviral vectors and sequential delivery of different vector serotype for long-term liver-directed gene transfer in baboons" *Proc. Natl. Acad. Sci. USA* 96: 12813-12821 (1999)), and reduced vector toxicity and immunogenicity (Schiedner et al., 1998; Morral et al., 1998; 1999; Reddy et al., 2002).

Gutless vectors are grown in the presence of a helper virus that supplies the structural proteins required for replication and packaging. The differential packaging strategy for the preferential packaging of the gutless vector rather than the helper virus is used. The packaging signal in the helper virus is surrounded by lox sites. In the presence of Cre recombinase, the packaging signal is removed. The gutless vector, in contrast, contains a functional packaging signal. Therefore, in the producer cells, in the presence of Cre recombinase, the gutless vector is preferentially packaged. The majority of mature vector particles are the gutless vector. Most of the helper virus contamination of the gutless vector is removed by CsCl gradient purification.

First, a vector plasmid is constructed, which contains either the fusion protein regulator, or the regulatable transgene as described previously (Example 2). These two expression cassettes are incorporated into a gutless vector backbone plasmid, containing the adenoviral sequences required for replication and packaging (ITRs and packaging signal), as well as a DNA stuffer sequence to increase the vector size to within adenovirus packaging limitations (28-38 kb; Parks R J, Graham Fla., "A helper-dependent system for adenovirus vector production helps define a lower limit for efficient DNA packaging" *J. Virol.* 71:3293-8 (1997)). The gutless vector is generated from this plasmid following transfection into an adenoviral producer cell line in the presence of helper virus. The producer cell line supplies any adenoviral genes that are needed to complement the helper virus and also express a recombinase that mediates the excision of the packaging signal from the helper virus. The helper virus contains a functional adenoviral packaging signal flanked by recombinase recognition sites. The helper virus can also have one or more essential adenovirus genes deleted, if the complementing cell line can complement for these deletions in trans.

Procedure

Construct Gutless Adenovirus Plasmids.

Figure 9:
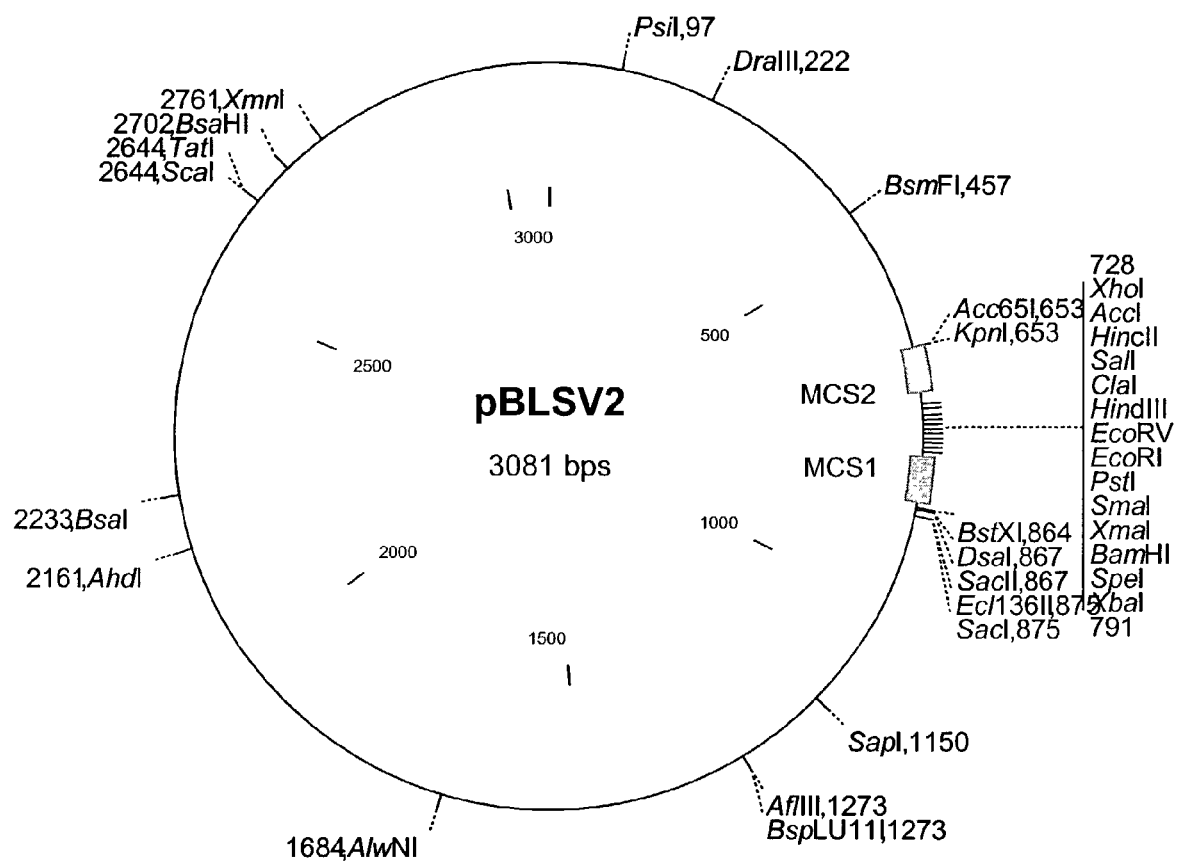
FIG. 9 shows a schematic diagram of pBLSV2.
Figure 10:
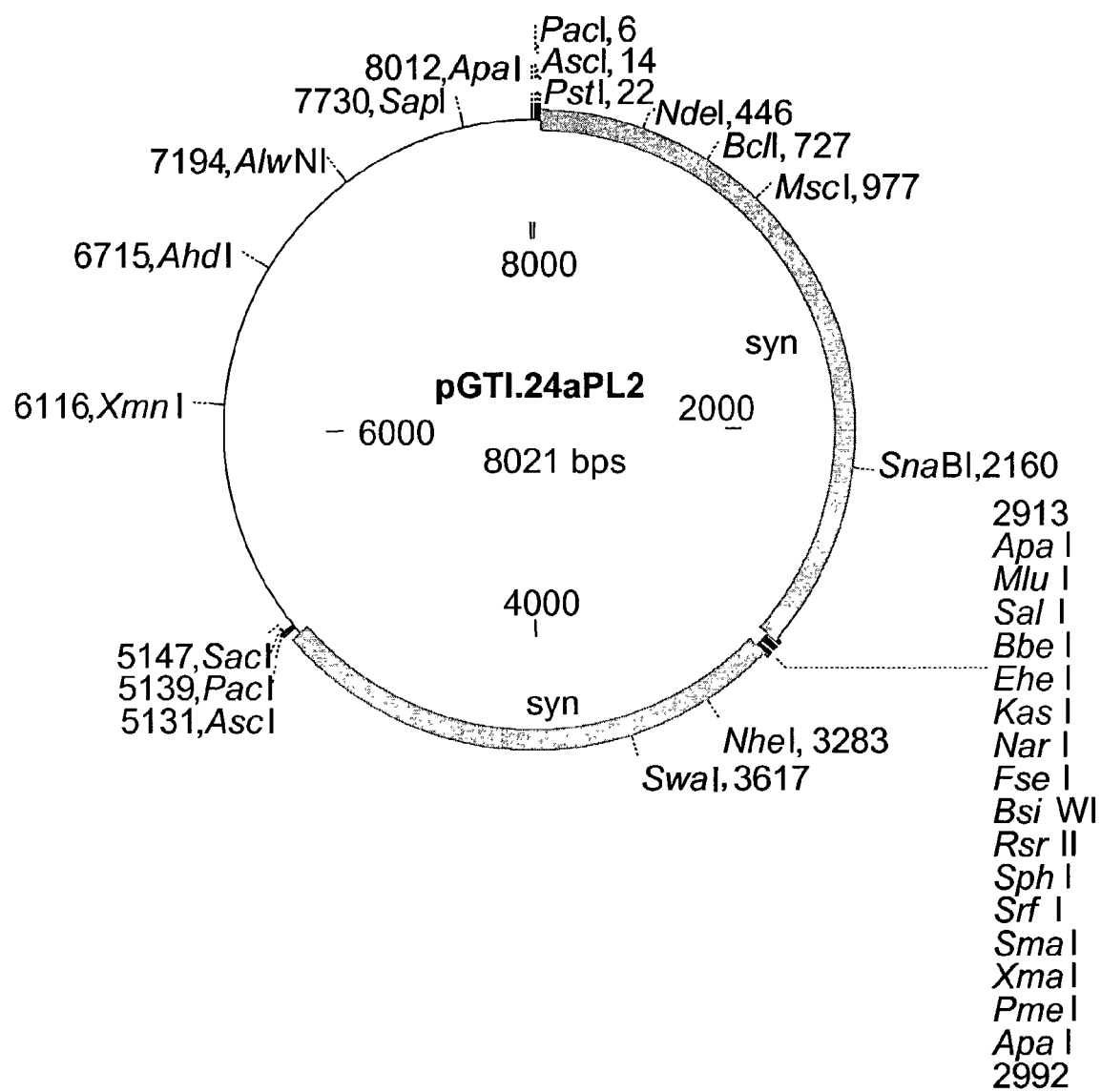
FIG. 10 shows a schematic diagram of the gutless vector cloning plasmid, pGTI.24aPL2.
Figure 11:
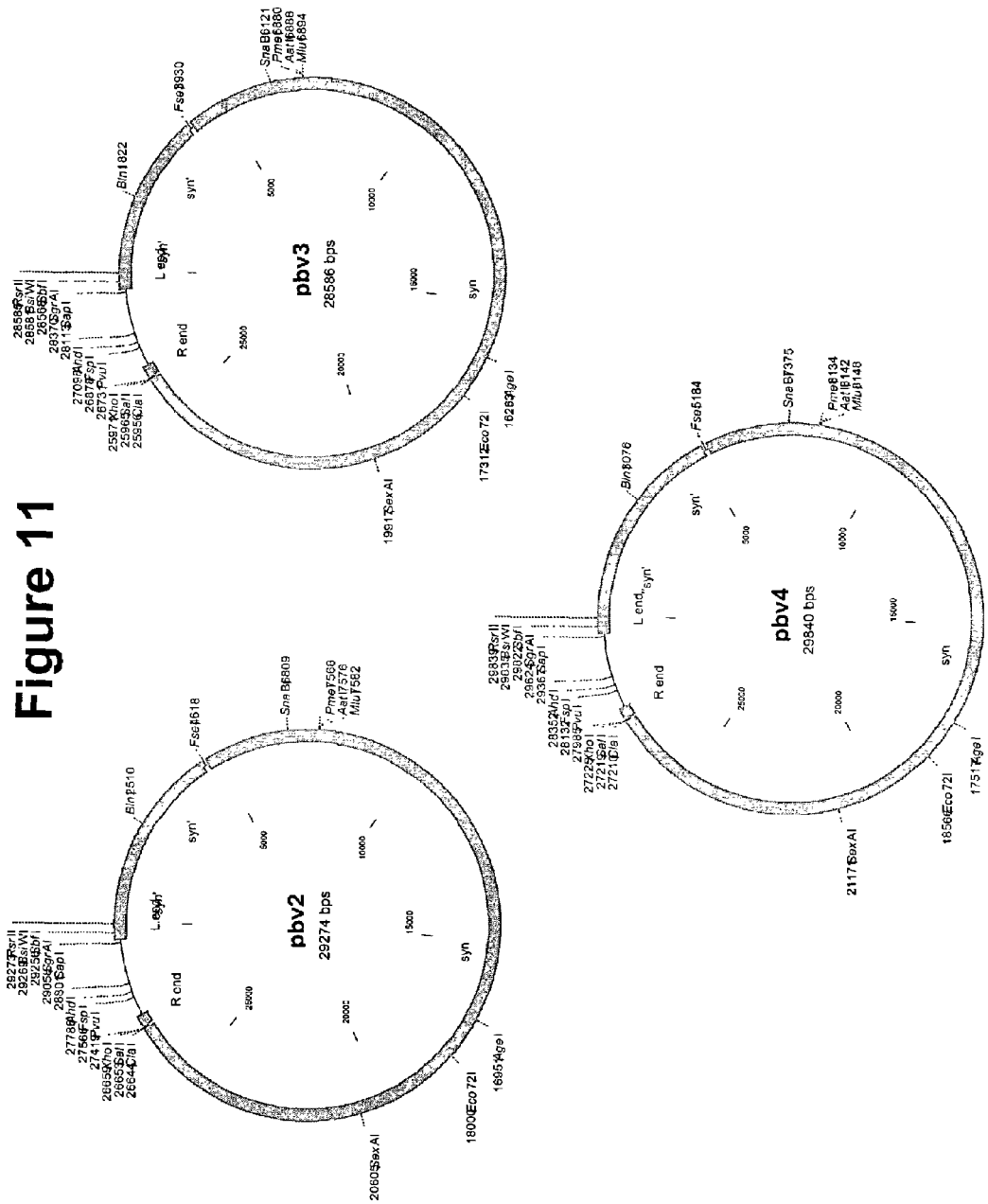
FIG. 11 shows a schematic diagram of the plasmids pBV2, pBV3 and pBV4.

The plasmids contain the viral left ITR, viral packaging signal, the ZFP-LBD fusion protein regulator linked to the immediate early CMV promoter or the regulatable transgene linked to the 6×2C7 array of C7 binding sites and the minimal promoter from SV40 or c-fos TATA (as described previously), some additional "stuffer" DNA sequences (U.S. patent application 60/344,073, filed Dec. 28, 2001, entitled "Adenoviral Vectors Including Stuffer DNA Sequences With Increased Amounts of Adenine and Thymine"), and the right ITR. The ITRs flank the construct. Specifically, the transcription factor G521R gutless vector plasmid was constructed by isolating the G52 1 R transgene expression cassette (Xu et al., "A versatile framework for the design of ligand-dependent, transgene-specific transcription factors" *Mol. Ther.* 3: 262-273 (2001)) derived from pAvCv-C7LBD (G521R) described previously by NruI and BamHI digestion and insertion into pBLSV2 digested with SmaI and BamHI. The plasmid pBLSV2 was derived from pBluescript (Stratagene) with the addition of two polylinkers (FIG. 9). The resulting plasmid, pBLSV2as521 is digested with BspeI and ligated to pGTI.24aPL2 (FIG. 10) digested with XmaI, to generate pGTI24as521. To construct the final gutless vector plasmid, pGTI24as521 is digested with PacI to liberate the plasmid backbone, and combined with PmeI/MluI digested pBV2 (FIG. 11). The final gutless vector plasmid is then generated by homologous recombination in BJ5138 *E. coli* as described by Toietta et al. (Toietta et al., "Generation of helper-dependent adenoviral vectors by homologous recombination" *Mol. Ther.* 5: 204-210 (2002)).

The gutless vector plasmids encoding the novel transcription factors 388V-424Y-428A, 524G, or 421V-428A are constructed by isolating the transcription factor expression cassette from the appropriate plasmid (e.g. pAvCv-C7LBD 388V-424Y-428A, described previously) by digesting with NruI and BamHI, and filling in the ends, and ligating to pGTI24.aPL2 digested with SmaI to generate pGTI24VYA, pGTI24-524, or pGTI24-421/428. The pGTI.24aPL2 plasmids encoding the transcription factors are then digested with PacI to liberate the plasmid backbone, and the pGTI24VYA and pGTI24-421/428 plasmids were combined with PmeI and MluI digested pBV2 (FIG. 11), or the pGTI24-524 plasmid is combined with PmeI and MluI digested pBV3 (FIG. 11). The final gutless vector plasmids are then generated by homologous recombination in BJ5138 *E. coli* as described by Toietta et al. (2002).

To construct the regulatable promoter/endostatin transgene gutless vector, the plasmid pav-6×2C7tatamendo (Xu et al., 2001) is digested with AscI, ends filled in, and digested with BamHI and inserted into pBLSV2 (FIG. 9) digested with SamI and BamHI to generate pBLSV2C7endo. The plasmid pBLSV2C7endo is then digested with BamHI and EcoRI, ends filled in, and ligated to pGTI24.aPL2 digested with SmaI to generate pGTI24C7endo. Then pGTI24C7endo is digested with PacI to liberate the plasmid backbone, and combined with PmeI and MluI digested pBV4 (FIG. 11). The final gutless vector plasmid is generated by homologous recombination in BJ5138 *E. Coli* as described by Toietta et al. (2002).

Transfect the Producer Cell line with the "Gutless" Adenovirus Plasmid

It is preferred that the gutless adenovirus plasmid is digested with one or more restriction enzymes that cut outside the gutless adenoviral vector DNA and as close as possible to each ITR. After transfection, the cells are infected with the helper virus. Preferably, this infection occurs at 20 hours after the transfection, and the helper virus is infected at a ratio of 100 to 200 particles per cell. The cells are incubated until complete cytopathic effect (CPE) is noticed (approximately 2-3 days post-infection). The cells and media are collected by scraping the plate and transferring the supernatant and cells to an appropriate tube. The cells and media are subjected to three rounds of freeze (−70° C. or dry ice) and thaw (37° C.) to lyse the cells and release the virus. This crude viral lysate (CVL) is then used to further amplify the gutless vector. The CVL is then used to infect more cultures of the producer cells, which are subsequently infected with helper virus. It is preferred that the helper virus be infected at a ratio of 100 to 200 particles per cell. This passaging of the CVLs can continue until a sufficient amount of gutless virus is obtained to purify by CsCl equilibrium density centrifugation. The final CVL is subjected to final purification by standard procedures known to those skilled in the art. One method is purification by CsCl ultracentrifugation using standard techniques. More than one equilibrium density gradient centrifugation may be employed to further reduce the level of helper virus contamination.

Figure 12:
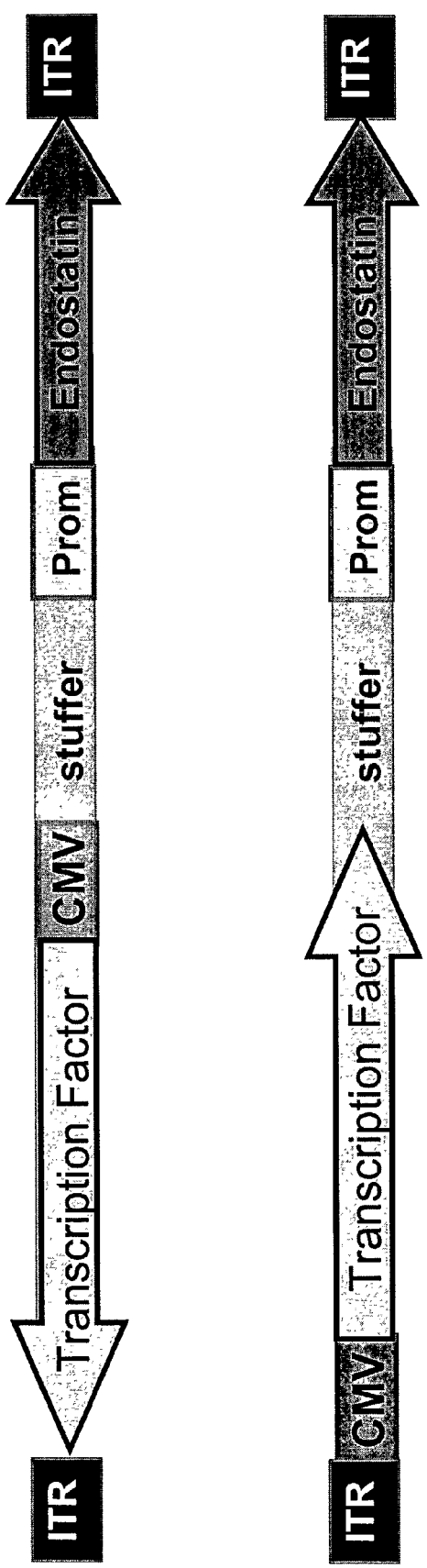
FIG. 12 shows two examples of gutless adenoviral vectors, each encoding both the novel transcription factor and the regulatable endostatin coding sequence.

In addition to the example above, where the fusion protein transcription factor and the regulated transgene are contained in two separate gutless adenoviral vectors, both expression cassettes can be incorporated into one vector and delivered as described. Such vectors have been designed and two examples are displayed in (FIG. 12). Alternatively, in another embodiment, a gutless vector containing the transgene, or a gutless vector containing the transcription factor, can be used along with the coordinating system component incorporated into some other vector, including but not limited to: adenoviral or lentiviral vectors. The other vector systems could be used to deliver the transcription factor or the regulated transgene component.

Results

In Vitro Regulation with Gutless Adenoviral Vectors

The ability to regulate expression of a transgene delivered by an adenovirus vector was demonstrated by the following experiment. Hela cells were infected with a mixture of two adenovirus vectors, one containing a fusion protein regulator (FIG. 13), the other containing the regulated luciferase expression cassette, in an Av3 vector backbone as described previously (Xu et al., 2001). The two vectors were used at a dose of 50 vector particles per cell of the Av3 vector encoding the 6×2C7-SV40-Luciferase transgene cassette (Xu et al., 2001), and 750 vector particles per cell of the gutless transcription factor vectors. Twenty four hours after vector transduction, the cells were treated where appropriate with 100 nM of the test compound. Following an additional 24 hrs incubation, the cells were lysed and assayed for luciferase activity as previously described. The results of this experiment are summarized in Table 8.

TABLE 8

In vitro inducible expression with novel LBDs and ligands.
The novel transcription factor and cognate ligand is displayed.
The (−) and (+) indicate the basal expression levels without ligand,
or the induced levels with ligand, respectively. Data are displayed
as the mean value +/− standard error (n = 4).

| Transcription Factor | Inducing Compound | Luciferase Expression Levels (Relative Light Units) | Fold Induction |
| --- | --- | --- | --- |
| G521R | 4-OH-Tamoxifen (−) (+) | 33092 +/− 1825 10,845,475 +/− 48073 | 33 |
| 388V-424Y-428A | LBB938 (−) (+) | 36256 +/− 655 3284939 +/− 116076 | 90 |
| 524G | LBF580 (−) (+) | 36097 +/− 940 285695 +/− 2331 | 8 |
| 421V-428A | LBG551 (−) (+) | 30638 +/− 694 154388 +/− 2485 | 5 |

These data indicate that all three mutant LBD and novel compound combinations tested were able to stimulate luciferase reporter gene activity in a drug-dependent manner. Response of the 421V-428A mutant to LBG551 was a 5-fold induction, and the response of 524G to LBF580 was 8-fold, the 388V-424Y-428A mutant responded to LBB938 with a 90-fold induction as compared to a 33-fold induction of G521R with 4-OHT. These data are similar to those obtained using the Av3 vectors displayed in FIG. 5, and confirm the function of this regulation system in the context of gutless adenoviral vectors.

In Vivo Regulation of Transgene Expression

Figure 14:
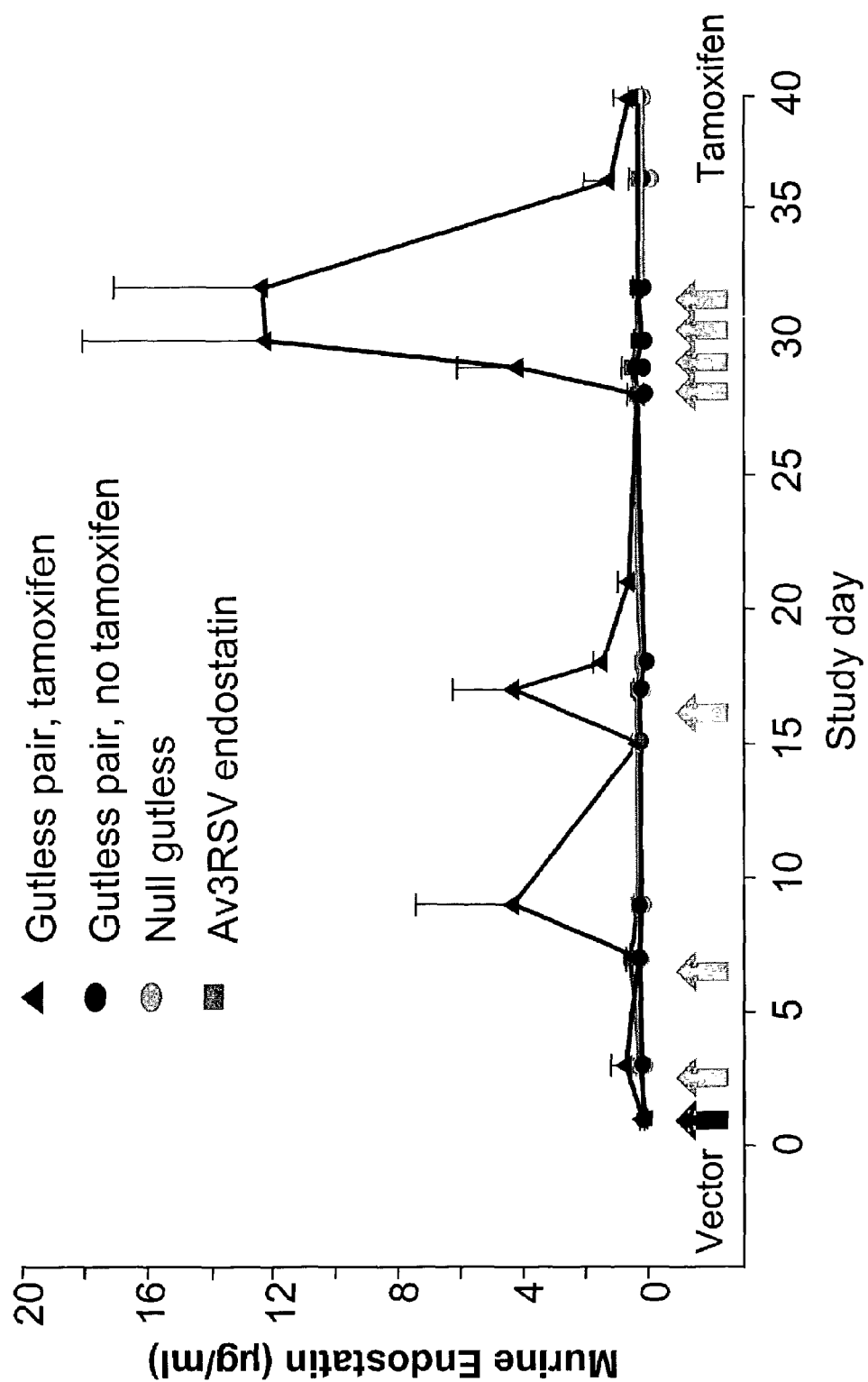
FIG. 14 shows the results when C57BL/6 male mice were treated via tail vein injection with $1 \times 10^{11}$ particles/mouse of the endostatin target vector and G521R transcription factor encoding gutless vectors (total vector dose of $2 \times 10^{11}$ particles (indicated by the black arrow). Tamoxifen (50 ug/mouse) was delivered IP at the indicated times (grey arrows).

C57BL/6 male mice were treated via tail vein injection with $1\times10^{11}$ particles/mouse of the endostatin target vector and G521R transcription factor encoding gutless vectors (total vector dose of $2\times10^{11}$ particles (indicated by the black arrow, FIG. 14). Tamoxifen (50 ug/mouse) was delivered IP at the indicated times (grey arrows, FIG. 14). Mice were bled the day after tamoxifen administration, and endostatin levels were measured in the serum using a mouse endostatin-specific ELISA. Endostatin expression was induced 4 times with tamoxifen. Following 4 sequential administrations of tamoxifen, extremely high levels of endostatin were observed, up to 20 ug/ml in some animals. Low basal levels of endostatin were observed with both the null gutless vector treated group, and the gutless vector pair without tamoxifen, demonstrating low or no expression when the ligand was not present (FIG. 14).

To further evaluate the regulation system in vivo, C57BL/6 male mice were treated via tail vein injection with $1\times10^{11}$ particles/mouse of the endostatin target vector and 388V-424Y-428A or G521R, transcription factor encoding gutless vectors (total vector dose of $2\times10^{11}$ particles), N=20. As a control, another group of mice (n=6) were treated with $2\times10^{11}$ particles of a gutless vector lacking a transgene, AGVNull (Reddy et al., 2002). The novel ligand, LBG612 (the non-hydroxylated form of LBB938) was delivered through IP injection at a dose of 50 ug/mouse one week after vector administration to mice that received the 388V-424Y-428A vector (n=10), while mice that received the G521R vector received the same dose of tamoxifen (n=10). The next day, mice were bled and endostatin levels were measured in the serum using a mouse endostatin-specific ELISA, and compared to levels in the mouse cohorts that received both vectors but did not receive the appropriate ligand (n=10). Endostatin expression was induced to high levels in both groups of mice (Table 9).

TABLE 9

In vivo evaluation of the 388V-424Y-428A transcription factor system versus the G521R transcription factor system. The (−) and (+) indicate the basal expression levels without ligand, or the induced levels with ligand, respectively. Data are displayed as the mean value +/− standard deviation (n = 6-10).

| Vector | Endostatin (ng/ml) | | |
|---|---|---|---|
| | Day 1 | Day 7 | Day 14 |
| AGVNull | 114 +/− 13 | 113 +/− 6 | 88 +/− 6 |
| G521R Not induced | 146 +/− 12 | 163 +/− 15 | 118 +/− 13 |
| G521R Induced | 15854 +/− 6885 | 208 +/− 27 | 179 +/− 40 |
| 388V-424Y-428A Not induced | 192 +/− 31 | 173 +/− 21 | 142 +/− 17 |

TABLE 9-continued

In vivo evaluation of the 388V-424Y-428A transcription factor system versus the G521R transcription factor system. The (−) and (+) indicate the basal expression levels without ligand, or the induced levels with ligand, respectively. Data are displayed as the mean value +/− standard deviation (n = 6-10).

| Vector | Endostatin (ng/ml) | | |
|---|---|---|---|
| | Day 1 | Day 7 | Day 14 |
| 388V-424Y-428A Induced | 14559 +/− 14312 | 2110 +/− 1380 | 572 +/− 312 |

Approximately 100-fold inductions were observed with both systems. Similar low basal levels of endostatin were observed with both the null gutless vector-treated group, and the gutless vector pairs without ligand, both the G521R and the 388V-424Y-428A transcription factors, demonstrating low or no expression when the ligand was not present. These data demonstrate the function of the regulation system in vivo, in the context of gutless adenoviral vectors. Comparison of the time course of induction revealed, however, that while the G521R system was down to baseline within one week after induction, the 388V-424Y-428A group still displayed endostatin levels well above baseline two weeks after a single induction. However, the endostatin levels were decreasing, with a 25-fold decrease between days 1 to 14 (Table B).

To address this issue of sustained induction, a second in vivo study was performed. C57BL/6 mice were treated via tail vein injection with $5\times10^{10}$ particles/mouse of the endostatin target vector and 388V-424Y-428A or G521R, transcription factor encoding gutless vectors (total vector dose of $1\times10^{11}$ particles), n=3. The novel ligand, LBG612 (the non-hydroxylated form of LBB938), or LBB938 was delivered through IP injection at a dose of 50 ug/mouse one week after vector administration. Mice were bled on day 1, 3 and 7 following vector treatment and endostatin levels were measured in the serum using a mouse endostatin-specific ELISA. Data are presented in Table 10.

TABLE 10

In vivo comparison of the 388V-424Y-428A transcription factor system using either the non-hydroxylated cognate ligand LBG612 or the hydroxylated cognate ligand LBB938. Compounds were delivered IP at a dose of 50 ug/animal. Data are displayed as the mean +/− standard deviation (n = 3). The (*) indicates that the value was over the high end of the ELISA standard curve.

| Ligand | Endostatin Levels (ng/ml) | | | |
|---|---|---|---|---|
| | Pre-induction | Day 1 | Day 3 | Day 7 |
| LBG612 | 95 +/− 2 | 663 +/− 313 | >5000* | >5000* |
| LBB938 | 112 +/− 8 | 6074 +/− 3536 | 2332 +/− 333 | 600 +/− 72 |

Animals treated with the hydroxylated LBB938 compound displayed a more rapid peak in endostatin expression, which also declined more rapidly than that of animals treated with the non-hydroxylated LBG612 compound. These data demonstrate that both LBG612 and LBB938 induce endostatin expression.

Example 7

Preparation of LBB938

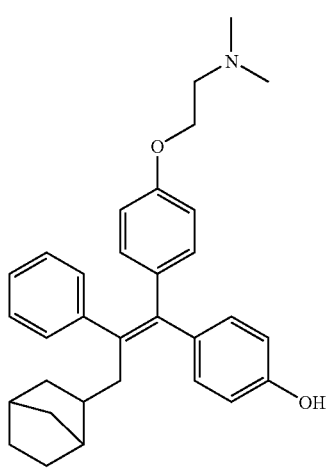

4-((1Z))-3-bicyclo[hept-2-yl-1-{4-[2-(dimethy-lamino)ethoxy]phenyl}-2-phenylprop-1-enyl)phenol The compound LBB938 is prepared according to the route outlined in Scheme 1 and is described in detail below.

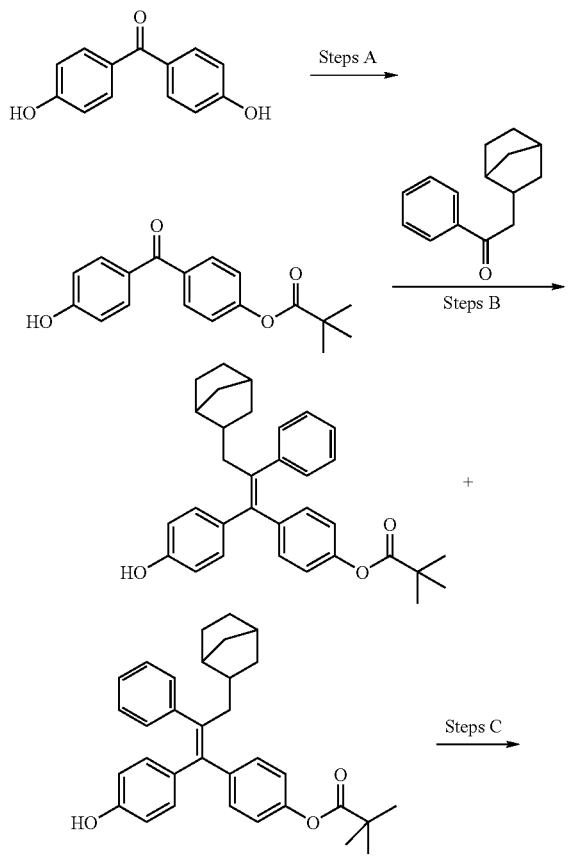

Scheme 1

Step A: Under an atmosphere of nitrogen and at room temperature, di 4-hydroxyphenyl ketone (12.4g, 58 mmol) is added to dry THF. 1.2 equivalents of sodium hydride (2.70 g, 70 mmol) are added portionwise and allowed to stir for one hour. The solution is cooled to 0° C. and 1.1 equivalents of trimethyl acetyl chloride (7.8 mls, 64 mmol) is added slowly, stirred for 30 minutes at 0° C. followed by stirring at room temperature for 3 hours. Water is added to quench the reaction and the organics are extracted with ethyl acetate, washed with brine and dried over sodium sulfate. After evaporation of solvent, the mixture of mono-acylated and di-acylated products are separated and purified on silica gel column with an eluent of 5% methanol/methylene chloride to give 4-[(4-hydroxyphenyl)carbonyl]phenyl 2,2-dimethyl-propanoate as white powder.

Step B: 4 equivalents of titanium chloride (1.1 mls, 10 mmol) are added dropwise to a slurry of 8 equivalents of zinc (1.3 g, 20 mmol) in anhydrous THF and refluxed at 90° C. for 2 hours. One equivalent each of the product of step A (0.75 g, 2.5 mmol) and the ketone 2-bicyclo[2.2.1]hept-2-yl-1-phenylethan-1-one (1.6 g, 7.5 mmol) are added together to the reaction mixture in one portion and allowed to reflux for an additional 5 hours. The reaction is quenched with the addition of a 20% solution of potassium carbonate and filtered through a glass fritted funnel. The organics are extracted into ethyl acetate, washed with brine, dried over sodium sulfate and concentrated in vacuo. The crude product is purified on a silica gel column with an eluent of 20% ethyl acetate/hexane to give a mixture of 4-[(1Z)-3-bicyclo[2.2.1]hept-2-yl-1-(4-oxyphenyl)-2-phenylprop-1-enyl]phenyl 2,2-dimethylpropanoate and 4-[(1E)-3-bicyclo[2.2.1]hept-2-yl-1-(4-oxyphenyl)-2-phenylprop-1-enyl]phenyl 2,2-dimethylpropanoate as a white powder.

Step C: The product of step B (1.0 g, 2.1 mmol), together with 2 equivalents of (2-chloroethyl)dimethylamine (0.6 g, 4.2 mmol) and 1.2 equivalents of potassium carbonate (0.35 g, 2.5 mmol) are heated at reflux in a 19:1 mixture of acetone:water for 5 hours. The mixture is diluted with methylene chloride, dried over sodium sulfate and the solvent is removed in vacuo to give a yellow solid. The crude product is purified on a silica gel column with an eluent gradient of 4% to 30% methanol/methylene chloride to give a mixture of 4-((1 Z)-3-bicyclo[2.2.1]hept-2-yl-1-{4-[2-(dimethylamino)ethoxy]phenyl}-2-phenylprop-1-enyl)phenyl 2,2-dimethylpropanoate and 4-((1E)-3-bicyclo[2.2.1]hept-2-yl 1- {4-[2-(dimethylamino)ethoxy]phenyl}-2-phenylprop-1-enyl)phenyl 2,2-dimethylpropanoate as a white powder.

Step D: The product of step C (0.27 g, 0.49 mmol) is dissolved in dry THF and cooled to 0° C. 1.3 equivalents of 1.6 M methyllithium in ether (0.4 mls, 0.6 mmol) is added and the solution is stirred at 0° C. for one hour and allowed to slowly warm to room temperature. Water is added and the organics are extracted with ethyl acetate, dried over sodium sulfate and concentrated in vacuo to give a white solid. The title compound is isolated as a white solid by recrystalization from methanol. MS, m/z 468 (m+1); m.p. 171-172° C., calculated for $C_{32}H_{37}NO_2$: C, 82.19; H, 7.97; N, 3.00. Found: C, 82.08; H, 7.92; N, 2.94.

Example 8

Preparation of LBF580

4-((1E)-1-{4-[2-(dimethylamino)ethoxy]phenyl}-2-(4-morpholin-4-ylphenyl)prop-1-enyl)phenol

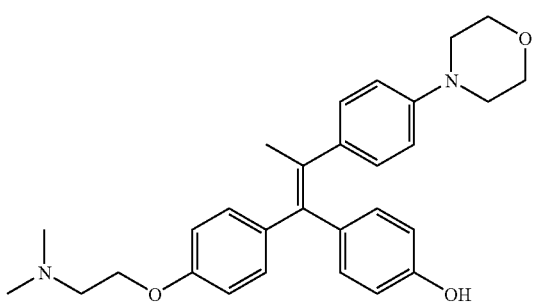

The compound LBF580 is prepared according to the route outlined in Scheme 2 and is described in detail below.

Scheme 2

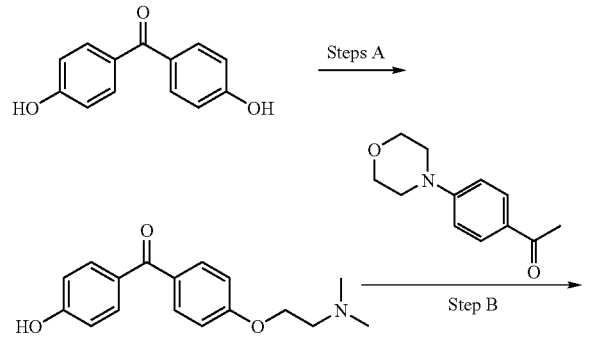

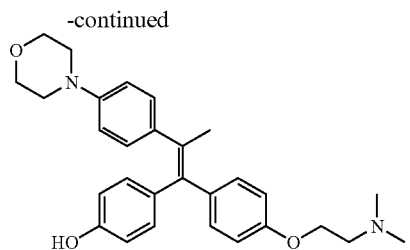

Step A: Di 4-hydroxyphenyl ketone (12.4g, 58 mmol), together with 1.0 equivalent of (2-chloroethyl)dimethylamine hydrochloride (8.30 g, 58 mmol) and 2.5 equivalents of cesium carbonate (47.2 g, 145 mmol) are heated at reflux in anhydrous DMF for 24 hours. The mixture is diluted with water and the product is extracted into ethyl acetate, dried over sodium sulfate and the solvent is removed in vacuo to give an off-white solid. The crude product is purified by trituration with acetone to give 4-({4-(dimethylamino) ethoxy]phenyl}methyl)phenol as a white powder.

Step B: 4 equivalents of titanium chloride (1.1 mls, 10 mmol) are added dropwise to a slurry of 8 equivalents of zinc (1.3 g, 20 mmol) in anhydrous THF and refluxed at 90° C. for 2 hours. One equivalent each of the product of step A (0.51 g, 2.5 mmol) and the ketone 1-(4-morpholin-4-ylphenyl)ethan-1-one (0.71 g, 2.5 mmol) are added together to the reaction mixture in one portion and allowed to reflux for an additional 5 hours. The reaction is quenched with the addition of a 20% solution of potassium carbonate and filtered through a glass fritted funnel. The organics are extracted into ethyl acetate, washed with brine, dried over sodium sulfate and concentrated in vacuo. The crude product is purified on a silica gel column with an eluent of 20% ethyl acetate/hexane to give the product as a pale yellow powder.

Example 9

Preparation of compound LBC081

LBC081, Carbamic acid, [(2E)-3-[4-[2-(dimethylamino) ethoxy]phenyl]-3-(4-hydroxyphenyl)-2-phenyl-2-propenyl]-, methyl ester

LBC081

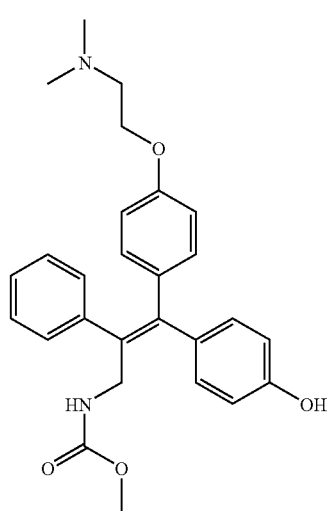

A suspension of zinc (1.83 g, 28.0 mmol), titanium tetrachloride (2.=g, 14.0 mmol) in 35 mL of THF is refluxed for 2 h. To this mixture is added propanoic acid, 2,2-dimethyl-, 4-(4-hydroxybenzoyl)phenyl ester (1.0 g, 3.5 mmol) and carbamic acid, (2-oxo-2-phenylethyl)-, methyl ester (2.0 g, 10.36 mmol) in 60 mL of THF. The mixture is refluxed for 5 h, cooled and poured into 10% $K_2CO_3$. The emulsion is filtered and extracted with ethyl acetate, washed with brine, dried over $MgSO_4$, filtered, concentrated and chromatographed on silica gel eluting with ethyl acetate/hexanes (1:3) to give propanoic acid, 2,2-dimethyl-, 4-[(1Z)-1 -(4-hydroxyphenyl)-3-[(methoxycarbonyl)amino]-2-phenyl-1-propenyl]phenyl ester 1.

A mixture of 1 (0.60 g, 1.31 mmol), acetone (20 mL), water (1 mL), $K_2CO_3$ (0.23 g, 1.68 mmol), and dimethylaminoethylchloride (0.28 mL, 2.'mmol) is refluxed for 5 h, cooled, $MgSO_4$ added, filtered, concentrated and chromatographed on silica gel eluting with 10% $CH_3OH/CH_2Cl_2$ to give propanoic acid, 2,2-dimethyl-, 4-[(1Z)-1-[4-[2-(dimethylamino)ethoxy]phenyl]-3-[(methoxycarbonyl)amino]-2-phenyl-1-propenyl]phenyl ester 2.

To a 0° C. solution of 2 (0.32 g, 0.603 mmol) in 10 mL of THF is added 1.5M methyl lithium (1.61 mL, 2.41 mmol). The mixture is stirred for 3 h, quenched with 3 mL of saturated $NH_4Cl$ and extracted with ethyl acetate. The organic layer is washed with brine, dried over $MgSO_4$, filtered, and concentrated. Crystallization from ether gave carbamic acid, [(2E)-3-[4-[2-(dimethylamino)ethoxy]phenyl]-3-(4-hydroxyphenyl)-2-phenyl-2-propenyl]-, methyl ester 3 melting at 161-162° C.; MS, m/z 447.5 (m+1). Anal. Calcd for $C_{27}H_{30}N_2O_4$: C, 72.62; H, 6.77; N, 6.27. Found: C, 72.48; H, 6.71; N, 6.21.

Example 10

Preparation of the compound LBB551

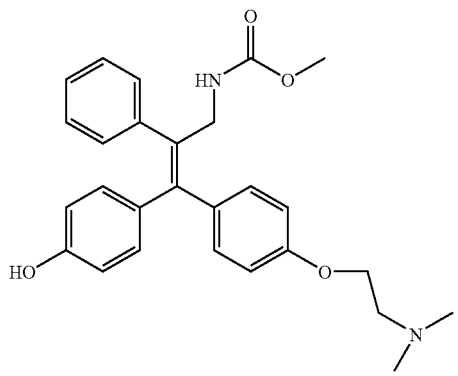

Carbamic acid, [(2Z)-3-[4-[2-(dimethylamino)ethoxy]phenyl]-3-(4-hydroxyphenyl)-2-phenyl-2-propenyl]-, methyl ester. Also (N-((2Z)-3-{4-[2-(dimethylamino)ethoxy]phenyl}-3-(4-hydroxyphenyl)-2-phenylprop-2-enyl) methoxycarboxamide)

A suspension of zinc (1.44 g, 22.0 mmol), titanium tetrachloride (1.21 mL, 11.0 mmol) in 20 mL of THF is refluxed for 2 h. To this mixture is added methanone, [4-[2-(dimethylamino)ethoxy]phenyl](4-hydroxyphenyl)- (0.784 g, 2.75 mmol) and carbamic acid, (2-oxo-2-phenylethyl)- methyl ester (1.59 g, 8.25 mmol) in 40 mL of THF. The mixture is refluxed for 5 h, cooled and poured into 10% $K_2CO_3$. The emulsion is filtered and extracted with ethyl acetate, washed with brine, dried over $MgSO_4$, filtered, concentrated and chromatographed on silica gel eluting with 10% CH30H (NH40H)/CH2Cl2 to give a mixture of 4 and 3. Crystallization from ether gave carbamic acid, [(2Z)-3-[4-[2-(dimethylamino)ethoxy]phenyl]-3-(4-hydroxyphenyl)-2-phenyl-2-propenyl]-, methyl ester 4 melting at 122-123° C.; MS, m/z 447.5 (m+1). Anal. Calcd for $C_{27}H_{30}N_2O_4$: C, 72.62; H, 677; N, 6.27. Found: C, 72.48; H, 6.61; N, 6.17.

Example 11

BIV Lentiviral Vectors

The tamoxifen-inducible gene expression system described by Xu et al. ("A versatile framework for the design of ligand-dependent, transgene-specific transcription factors" *Mol. Ther.* 3(2): 262-73 (2001)) was tested in BIV vectors. The BIV vector system has been described in previous U.S. patent application filed Feb. 4, 2002 entitled "Recombinant Bovine Immunodeficiency Virus Based Gene Transfer System" serial number to be assigned and Matukonis et al., "Development of Second and Third Generation of Bovine Immunodeficiency Virus Based Gene Transfer Systems" *Human Gene Therapy*, in press (2002). Four different DNA constructs were generated: (1) a reporter construct, pBIVC2H2EGFP, comprised of six tandem C7 binding sites upstream of an SV40 minimal promoter (Liu et al., "Design of polydactyl zinc-finger proteins for unique addressing within complex genomes" *Proc. Natl. Acad. Sci. U.S.A.* 94(11): 5525-30 (1997)) and eGFP transgene inserted into the Stu I site of the BIV transfer vector construct; (2) a reporter construct, pBIVC2H2FOSeGFP, comprised of six tandem C7 binding sites upstream of the 45-bp minimal TATA-box promoter fragment derived from the c-fos gene (Fluhmann et al., "Parathyroid hormone responses of cyclic AMP-, serum- and phorbol ester-responsive reporter genes in osteoblast-like UMR-106 cells" *Mol. Cell Endocrinol.* 139(1-2): 89-98 (1998)) and the eGFP transgene inserted into the StuI site of the BIV transfer vector construct; (3) an activator construct, pBIVMNDC7, comprised of a cDNA encoding the LBD/B chimeric transcription factor (Xu et al., 2001) inserted into the StuI site of the BIV transfer vector with MND as an internal promoter promoting LBD/B; and (4) an activator construct, pB MND2AS, comprised of a cDNA encoding the LBD/A chimeric transcription factor (Xu et al., 2001) inserted into the StuI site of the BIV transfer vector construct with MND as an internal promoter promoting LBD/A.

One of the reporter constructs described above was introduced individually into 3×106 293T cells along with other components of the BIV four component packaging system (U.S. patent application of Luo et al. filed Feb. 4, 2002 entitled "Recombinant Bovine Immunodeficiency Virus Based Gene Transfer System" Application Ser. No. 60/353, 177 and Matukonis et al., ("Development of Second and Third Generation of Bovine Immunodeficiency Virus Based Gene Transfer Systems" *Human Gene Therapy*, in press (2002)) by CaPO4-mediated transient transfection. Eighteen hours post transfection, media were replaced with fresh DMEM containing 10% FBS and 200 mM butyric acid. Forty-eight hours later, conditioned media were collected from the transfected cells. Two mls of conditioned media from each transfection plus 2 mls of DMEM/FBS were added to 2×105 293T cells in individual wells of a six well tissue culture plate. In addition, 2 mls of conditioned media from either the pBIVC2H2FOSeGFP transfections were combined with 2 mls of conditioned media from the pBIVMNDC7 or pBIVMND2AS transfections and added to 2×105 293T cells. 8 μg/ml protamine sulfate were added to each transduction reaction. Four hours later, conditioned media was removed from the transduced cells and replaced with fresh DMEM/FBS. Upon reaching confluency, cells from each well were trypsinized and split into two wells of a six well tissue-culture plate. After allowing the cells to settle overnight, 4-OH-tamoxifen (100 nM final concentration) was added to one of the duplicate wells from each sample of transduced cells. EGFP expression was analysed by digital photography and FACS analysis forty-eight hours after tamoxifen induction (Table 11).

TABLE 11

| Sample | Reporter | Activator | 4-OH-Tamoxifen | % Gated Cells |
|---|---|---|---|---|
| 1 | none | none | absent | 0.06 |
| 2 | BIVC2H2FOSEGFP | none | absent | 0.50 |
| 3 | BIVC2H2FOSEGFP | none | present | 0.36 |
| 4 | BIVC2H2FOSEGFP | BIVMNDC7 | absent | 0.17 |
| 5 | BIVC2H2FOSEGFP | BIVMNDC7 | present | 2.56 |
| 6 | BIVC2H2FOSEGFP | BIVMND2AS | absent | 0.20 |
| 7 | BIVC2H2FOSEGFP | BIVMND2AS | present | 4.10 |
| 8 | none | BIVMNDC7 | absent | 0 |
| 9 | none | BIVMNDC7 | present | 0 |
| 10 | none | BIVMND2AS | absent | 0.01 |
| 11 | none | BIVMND2AS | present | 0 |

All references cited herein are incorporated herein by reference in their entirety and for all purposes to the same extent as if each individual publication or patent or patent application was specifically and individually indicated to be incorporated by reference in its entirety for all purposes. In addition, all GenBank accession numbers, Unigene Cluster numbers and protein accession numbers cited herein are incorporated herein by reference in their entirety and for all purposes to the same extent as if each such number was specifically and individually indicated to be incorporated by reference in its entirety for all purposes.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein, will be apparent to those skilled in the art from the foregoing description and accompanying drawings. Such modifications and variations are intended to fall within the scope of the appended claims. The present invention is to be limited only by the terms of the appended claims, along with the full scope of equivalents to which such claims are entitled.

What is claimed is:

1. An isolated nucleic acid molecule comprising a nucleotide sequence encoding a modified estrogen receptor alpha ligand binding domain with an amino acid substitution at one or more of positions 388, 391, 424 or 428 of SEQ ID NO:55, wherein said ligand binding domain interacts with a non-native ligand.

2. The isolated nucleic acid molecule of claim 1 further comprising an operatively linked nucleic acid encoding a nucleic acid binding domain.

3. The isolated nucleic acid molecule of claim 2 further comprising an operably linked nucleotide sequence encoding a transcription regulatory domain.

4. A chimeric construct comprising a promoter operatively linked to the nucleic acid molecule of claim 1.

5. A chimeric construct comprising a promoter operatively linked to the nucleic acid molecule of claim 2 or 3.

6. A plasmid containing the chimeric construct of claim 4.

7. A plasmid containing the chimeric construct of claim 5.

8. The isolated nucleic acid of claim 1 comprising substitutions at two or more of said positions.

9. The isolated nucleic acid of claim 1 comprising substitutions at three or more of said positions.

10. An isolated nucleic acid molecule comprising a nucleotide sequence encoding a modified estrogen receptor alpha ligand binding domain with an amino acid substitution at one or more of positions 388, 391, 424 or 428 of SEQ ID NO:55; and an amino acid substitution at position 521, 524 or both of SEQ ID NO:55, wherein said ligand binding domain interacts with a non-native ligand.

11. The isolated nucleic acid of claim 10 further comprising an operatively linked nucleic acid encoding a nucleic acid binding domain.

12. The isolated nucleic acid of claim 11 further comprising a nucleic acid encoding an operably linked transcription regulatory domain.

13. A chimeric construct comprising a promoter operatively linked to the nucleic acid of claim 10.

14. A chimeric construct comprising a promoter operatively linked to the nucleic acid of claim 11.

15. A chimeric construct comprising a promoter operatively linked to the nucleic acid of claim 12.

16. A plasmid comprising the chimeric construct of claim 13.

17. A plasmid comprising the chimeric construct of claim 14.

18. A plasmid comprising the chimeric construct of claim 15.

19. The isolated nucleic acid molecule of claim 1 further comprising an amino acid substitution at position 421 of SEQ ID NO:55.

20. The nucleic acid molecule of claim 19 further comprising an operably linked nucleic acid encoding a nucleic acid binding domain.

21. The nucleic acid molecule of claim 20 further comprising an operably linked transcription regulatory domain.

22. A chimeric construct comprising a promoter operably linked to the nucleic acid molecule of claim 19.

23. A chimeric construct comprising a promoter operably linked to the nucleic acid molecule of claim 20.

24. A chimeric construct comprising a promoter operably linked to the nucleic acid molecule of claim 21.

25. A plasmid comprising the chimeric construct of claim 22.

26. A plasmid comprising the chimeric construct of claim 23.

27. A plasmid comprising the chimeric construct of claim 24.

* * * * *

SEQUENCE LISTING

```
<160> NUMBER OF SEQ ID NOS: 55

<210> SEQ ID NO 1
<211> LENGTH: 1245
<212> TYPE: DNA
<213> ORGANISM: Artificial Sequence
<220> FEATURE:
<223> OTHER INFORMATION: Fusion of the
      human-Estrogen-receptor-ligand-binding-domain and a zinc finger
      array(C7)
<220> FEATURE:
<221> NAME/KEY: CDS
<222> LOCATION: (1)..(1245)

<400> SEQUENCE: 1 atg gcc cag gcg gcc ctc gag ccc tat gct tgc cct gtc gag tcc tgc      48
Met Ala Gln Ala Ala Leu Glu Pro Tyr Ala Cys Pro Val Glu Ser Cys
1               5                   10                  15 gat cgc cgc ttt tct aag tcg gct gat ctg aag cgc cat atc cgc atc      96
Asp Arg Arg Phe Ser Lys Ser Ala Asp Leu Lys Arg His Ile Arg Ile
            20                  25                  30 cac aca ggc cag aag cct ttc cag tgt cga ata tgc atg cgt aac ttc     144
His Thr Gly Gln Lys Pro Phe Gln Cys Arg Ile Cys Met Arg Asn Phe
        35                  40                  45 agt cgt agt gac cac ctt acc acc cac atc cgc acc cac aca ggc gag     192
Ser Arg Ser Asp His Leu Thr Thr His Ile Arg Thr His Thr Gly Glu
    50                  55                  60 aag cct ttt gcc tgt gac att tgt ggg agg aag ttt gcc agg agt gat     240
Lys Pro Phe Ala Cys Asp Ile Cys Gly Arg Lys Phe Ala Arg Ser Asp
65                  70                  75                  80 gaa cgc aag agg cat acc aaa atc cat tta aga cag agg gac tct aga     288
Glu Arg Lys Arg His Thr Lys Ile His Leu Arg Gln Arg Asp Ser Arg
                85                  90                  95 act agt tct gct gga gac atg aga gct gcc aac ctt tgg cca agc ccg     336
Thr Ser Ser Ala Gly Asp Met Arg Ala Ala Asn Leu Trp Pro Ser Pro
            100                 105                 110 ctc atg atc aaa cgc tct aag aag aac agc ctg gcc ttg tcc ctg acg     384
```

```
                Leu Met Ile Lys Arg Ser Lys Lys Asn Ser Leu Ala Leu Ser Leu Thr
                            115                 120                 125 gcc gac cag atg gtc agt gcc ttg ttg gat gct gag ccc ccc ata ctc         432
Ala Asp Gln Met Val Ser Ala Leu Leu Asp Ala Glu Pro Pro Ile Leu
130                 135                 140 tat tcc gag tat gat cct acc aga ccc ttc agt gaa gct tcg atg atg         480
Tyr Ser Glu Tyr Asp Pro Thr Arg Pro Phe Ser Glu Ala Ser Met Met
145                 150                 155                 160 ggc tta ctg acc aac ctg gca gac agg gag ctg gtt cac atg atc aac         528
Gly Leu Leu Thr Asn Leu Ala Asp Arg Glu Leu Val His Met Ile Asn
                165                 170                 175 tgg gcg aag agg gtg cca ggc ttt gtg gat ttg acc ctc cat gat cag         576
Trp Ala Lys Arg Val Pro Gly Phe Val Asp Leu Thr Leu His Asp Gln
            180                 185                 190 gtc cac ctt cta gaa tgt gcc tgg cta gag atc ctg atg att ggt ctc         624
Val His Leu Leu Glu Cys Ala Trp Leu Glu Ile Leu Met Ile Gly Leu
        195                 200                 205 gtc tgg cgc tcc atg gag cac cca ggg aag cta ctg ttt gct cct aac         672
Val Trp Arg Ser Met Glu His Pro Gly Lys Leu Leu Phe Ala Pro Asn
    210                 215                 220 ttg ctc ttg gac agg aac cag gga aaa tgt gta gag ggc atg gtg gag         720
Leu Leu Leu Asp Arg Asn Gln Gly Lys Cys Val Glu Gly Met Val Glu
225                 230                 235                 240 atc ttc gac atg ctg ctg gct aca tca tct cgg ttc cgc atg atg aat         768
Ile Phe Asp Met Leu Leu Ala Thr Ser Ser Arg Phe Arg Met Met Asn
                245                 250                 255 ctg cag gga gag gag ttt gtg tgc ctc aaa tct att att ttg ctt aat         816
Leu Gln Gly Glu Glu Phe Val Cys Leu Lys Ser Ile Ile Leu Leu Asn
            260                 265                 270 tct gga gtg tac aca ttt ctg tcc agc acc ctg aag tct ctg gaa gag         864
Ser Gly Val Tyr Thr Phe Leu Ser Ser Thr Leu Lys Ser Leu Glu Glu
        275                 280                 285 aag gac cat atc cac cga gtc ctg gac aag atc aca gac act ttg atc         912
Lys Asp His Ile His Arg Val Leu Asp Lys Ile Thr Asp Thr Leu Ile
    290                 295                 300 cac ctg atg gcc aag gca ggc ctg acc ctg cag cag cag cac cag cgg         960
His Leu Met Ala Lys Ala Gly Leu Thr Leu Gln Gln Gln His Gln Arg
305                 310                 315                 320 ctg gcc cag ctc ctc ctc atc ctc tcc cac atc agg cac atg agt aac        1008
Leu Ala Gln Leu Leu Leu Ile Leu Ser His Ile Arg His Met Ser Asn
                325                 330                 335 aaa ggc atg gag cat ctg tac agc atg aag tgc aag aac gtg gtg ccc        1056
Lys Gly Met Glu His Leu Tyr Ser Met Lys Cys Lys Asn Val Val Pro
            340                 345                 350 ctc tat gac ctg ctg ctg gag atg ctg gac gcc cac cgc cta cat gcg        1104
Leu Tyr Asp Leu Leu Leu Glu Met Leu Asp Ala His Arg Leu His Ala
        355                 360                 365 ccc act agc cgt acg ccg gcc gac gcc ctg gac gac ttc gac ctg gac        1152
Pro Thr Ser Arg Thr Pro Ala Asp Ala Leu Asp Asp Phe Asp Leu Asp
    370                 375                 380 atg ctg ccg gcc gac gcc ctg gac gac ttc gac ctg gac atg ctg ccg        1200
Met Leu Pro Ala Asp Ala Leu Asp Asp Phe Asp Leu Asp Met Leu Pro
385                 390                 395                 400 gcc gac gcc ctg gac gac ttc gac ctg gac atg ctg ccg ggg taa            1245
Ala Asp Ala Leu Asp Asp Phe Asp Leu Asp Met Leu Pro Gly
                405                 410

<210> SEQ ID NO 2
<211> LENGTH: 414
<212> TYPE: PRT
```

<213> ORGANISM: Artificial Sequence
<220> FEATURE:
<223> OTHER INFORMATION: Fusion of the
human-Estrogen-receptor-ligand-binding-domain and a zinc finger
array(C7)

<400> SEQUENCE: 2

```
Met Ala Gln Ala Ala Leu Glu Pro Tyr Ala Cys Pro Val Glu Ser Cys
1               5                   10                  15

Asp Arg Arg Phe Ser Lys Ser Ala Asp Leu Lys Arg His Ile Arg Ile
            20                  25                  30

His Thr Gly Gln Lys Pro Phe Gln Cys Arg Ile Cys Met Arg Asn Phe
        35                  40                  45

Ser Arg Ser Asp His Leu Thr Thr His Ile Arg Thr His Thr Gly Glu
50                  55                  60

Lys Pro Phe Ala Cys Asp Ile Cys Gly Arg Lys Phe Ala Arg Ser Asp
65                  70                  75                  80

Glu Arg Lys Arg His Thr Lys Ile His Leu Arg Gln Arg Asp Ser Arg
            85                  90                  95

Thr Ser Ser Ala Gly Asp Met Arg Ala Ala Asn Leu Trp Pro Ser Pro
        100                 105                 110

Leu Met Ile Lys Arg Ser Lys Lys Asn Ser Leu Ala Leu Ser Leu Thr
    115                 120                 125

Ala Asp Gln Met Val Ser Ala Leu Leu Asp Ala Glu Pro Pro Ile Leu
130                 135                 140

Tyr Ser Glu Tyr Asp Pro Thr Arg Pro Phe Ser Glu Ala Ser Met Met
145                 150                 155                 160

Gly Leu Leu Thr Asn Leu Ala Asp Arg Glu Leu Val His Met Ile Asn
            165                 170                 175

Trp Ala Lys Arg Val Pro Gly Phe Val Asp Leu Thr Leu His Asp Gln
        180                 185                 190

Val His Leu Leu Glu Cys Ala Trp Leu Glu Ile Leu Met Ile Gly Leu
    195                 200                 205

Val Trp Arg Ser Met Glu His Pro Gly Lys Leu Leu Phe Ala Pro Asn
210                 215                 220

Leu Leu Leu Asp Arg Asn Gln Gly Lys Cys Val Glu Gly Met Val Glu
225                 230                 235                 240

Ile Phe Asp Met Leu Leu Ala Thr Ser Ser Arg Phe Arg Met Met Asn
            245                 250                 255

Leu Gln Gly Glu Glu Phe Val Cys Leu Lys Ser Ile Ile Leu Leu Asn
        260                 265                 270

Ser Gly Val Tyr Thr Phe Leu Ser Ser Thr Leu Lys Ser Leu Glu Glu
    275                 280                 285

Lys Asp His Ile His Arg Val Leu Asp Lys Ile Thr Asp Thr Leu Ile
290                 295                 300

His Leu Met Ala Lys Ala Gly Leu Thr Leu Gln Gln His Gln Arg
305                 310                 315                 320

Leu Ala Gln Leu Leu Leu Ile Leu Ser His Ile Arg His Met Ser Asn
            325                 330                 335

Lys Gly Met Glu His Leu Tyr Ser Met Lys Cys Lys Asn Val Val Pro
        340                 345                 350

Leu Tyr Asp Leu Leu Leu Glu Met Leu Asp Ala His Arg Leu His Ala
    355                 360                 365

Pro Thr Ser Arg Thr Pro Ala Asp Ala Leu Asp Asp Phe Asp Leu Asp
370                 375                 380
```

```
Met Leu Pro Ala Asp Ala Leu Asp Asp Phe Asp Leu Asp Met Leu Pro
385                 390                 395                 400

Ala Asp Ala Leu Asp Asp Phe Asp Leu Asp Met Leu Pro Gly
                405                 410
```

```
<210> SEQ ID NO 3
<211> LENGTH: 1317
<212> TYPE: DNA
<213> ORGANISM: Artificial Sequence
<220> FEATURE:
<223> OTHER INFORMATION: Fusion of the
      human-Estrogen-receptor-ligand-binding-domain and a zinc finger
      array(C7)
<220> FEATURE:
<221> NAME/KEY: CDS
<222> LOCATION: (1)..(1317)

<400> SEQUENCE: 3
```

```
atg gcc cag gcg gcc ctc gag ccc tat gct tgc cct gtc gag tcc tgc      48
Met Ala Gln Ala Ala Leu Glu Pro Tyr Ala Cys Pro Val Glu Ser Cys
1               5                   10                  15 gat cgc cgc ttt tct aag tcg gct gat ctg aag cgc cat atc cgc atc      96
Asp Arg Arg Phe Ser Lys Ser Ala Asp Leu Lys Arg His Ile Arg Ile
                20                  25                  30 cac aca ggc cag aag cct ttc cag tgt cga ata tgc atg cgt aac ttc     144
His Thr Gly Gln Lys Pro Phe Gln Cys Arg Ile Cys Met Arg Asn Phe
            35                  40                  45 agt cgt agt gac cac ctt acc acc cac atc cgc acc cac aca ggc gag     192
Ser Arg Ser Asp His Leu Thr Thr His Ile Arg Thr His Thr Gly Glu
        50                  55                  60 aag cct ttt gcc tgt gac att tgt ggg agg aag ttt gcc agg agt gat     240
Lys Pro Phe Ala Cys Asp Ile Cys Gly Arg Lys Phe Ala Arg Ser Asp
65                  70                  75                  80 gaa cgc aag agg cat acc aaa atc cat tta aga cag agg gac tct aga     288
Glu Arg Lys Arg His Thr Lys Ile His Leu Arg Gln Arg Asp Ser Arg
                85                  90                  95 act agt gac cga aga gga ggg aga atg ttg aaa cac aag cgc cag aga     336
Thr Ser Asp Arg Arg Gly Gly Arg Met Leu Lys His Lys Arg Gln Arg
            100                 105                 110 gat gat ggg gag ggc agg ggt gaa gtg ggg tct gct gga gac atg aga     384
Asp Asp Gly Glu Gly Arg Gly Glu Val Gly Ser Ala Gly Asp Met Arg
        115                 120                 125 gct gcc aac ctt tgg cca agc ccg ctc atg atc aaa cgc tct aag aag     432
Ala Ala Asn Leu Trp Pro Ser Pro Leu Met Ile Lys Arg Ser Lys Lys
130                 135                 140 aac agc ctg gcc ttg tcc ctg acg gcc gac cag atg gtc agt gcc ttg     480
Asn Ser Leu Ala Leu Ser Leu Thr Ala Asp Gln Met Val Ser Ala Leu
145                 150                 155                 160 ttg gat gct gag ccc ccc ata ctc tat tcc gag tat gat cct acc aga     528
Leu Asp Ala Glu Pro Pro Ile Leu Tyr Ser Glu Tyr Asp Pro Thr Arg
                165                 170                 175 ccc ttc agt gaa gct tcg atg atg ggc tta ctg acc aac ctg gca gac     576
Pro Phe Ser Glu Ala Ser Met Met Gly Leu Leu Thr Asn Leu Ala Asp
            180                 185                 190 agg gag ctg gtt cac atg atc aac tgg gcg aag agg gtg cca ggc ttt     624
Arg Glu Leu Val His Met Ile Asn Trp Ala Lys Arg Val Pro Gly Phe
        195                 200                 205 gtg gat ttg acc ctc cat gat cag gtc cac ctt cta gaa tgt gcc tgg     672
Val Asp Leu Thr Leu His Asp Gln Val His Leu Leu Glu Cys Ala Trp
    210                 215                 220 cta gag atc ctg atg att ggt ctc gtc tgg cgc tcc atg gag cac cca     720
Leu Glu Ile Leu Met Ile Gly Leu Val Trp Arg Ser Met Glu His Pro
```

```
Leu Glu Ile Leu Met Ile Gly Leu Val Trp Arg Ser Met Glu His Pro
225                 230                 235                 240 ggg aag cta ctg ttt gct cct aac ttg ctc ttg gac agg aac cag gga        768
Gly Lys Leu Leu Phe Ala Pro Asn Leu Leu Leu Asp Arg Asn Gln Gly
                245                 250                 255 aaa tgt gta gag ggc atg gtg gag atc ttc gac atg ctg ctg gct aca        816
Lys Cys Val Glu Gly Met Val Glu Ile Phe Asp Met Leu Leu Ala Thr
            260                 265                 270 tca tct cgg ttc cgc atg atg aat ctg cag gga gag gag ttt gtg tgc        864
Ser Ser Arg Phe Arg Met Met Asn Leu Gln Gly Glu Glu Phe Val Cys
        275                 280                 285 ctc aaa tct att att ttg ctt aat tct gga gtg tac aca ttt ctg tcc        912
Leu Lys Ser Ile Ile Leu Leu Asn Ser Gly Val Tyr Thr Phe Leu Ser
    290                 295                 300 agc acc ctg aag tct ctg gaa gag aag gac cat atc cac cga gtc ctg        960
Ser Thr Leu Lys Ser Leu Glu Glu Lys Asp His Ile His Arg Val Leu
305                 310                 315                 320 gac aag atc aca gac act ttg atc cac ctg atg gcc aag gca ggc ctg       1008
Asp Lys Ile Thr Asp Thr Leu Ile His Leu Met Ala Lys Ala Gly Leu
                325                 330                 335 acc ctg cag cag cag cac cag cgg ctg gcc cag ctc ctc ctc atc ctc       1056
Thr Leu Gln Gln Gln His Gln Arg Leu Ala Gln Leu Leu Leu Ile Leu
            340                 345                 350 tcc cac atc agg cac atg agt aac aaa ggc atg gag cat ctg tac agc       1104
Ser His Ile Arg His Met Ser Asn Lys Gly Met Glu His Leu Tyr Ser
        355                 360                 365 atg aag tgc aag aac gtg gtc ccc ctc tat gac ctg ctg ctg gag atg       1152
Met Lys Cys Lys Asn Val Val Pro Leu Tyr Asp Leu Leu Leu Glu Met
370                 375                 380 ctg gac gcc cac cgc cta cat gcg ccc act agc cgt acg ccg gcc gac       1200
Leu Asp Ala His Arg Leu His Ala Pro Thr Ser Arg Thr Pro Ala Asp
385                 390                 395                 400 gcc ctg gac gac ttc gac ctg gac atg ctg ccg gcc gac gcc ctg gac       1248
Ala Leu Asp Asp Phe Asp Leu Asp Met Leu Pro Ala Asp Ala Leu Asp
                405                 410                 415 gac ttc gac ctg gac atg ctg ccg gcc gac gcc ctg gac gac ttc gac       1296
Asp Phe Asp Leu Asp Met Leu Pro Ala Asp Ala Leu Asp Asp Phe Asp
            420                 425                 430 ctg gac atg ctg ccg ggg taa                                           1317
Leu Asp Met Leu Pro Gly
        435

<210> SEQ ID NO 4
<211> LENGTH: 438
<212> TYPE: PRT
<213> ORGANISM: Artificial Sequence
<220> FEATURE:
<223> OTHER INFORMATION: Fusion of the
      human-Estrogen-receptor-ligand-binding-domain and a zinc finger
      array(C7)

<400> SEQUENCE: 4

Met Ala Gln Ala Ala Leu Glu Pro Tyr Ala Cys Pro Val Glu Ser Cys
1               5                   10                  15

Asp Arg Arg Phe Ser Lys Ser Ala Asp Leu Lys Arg His Ile Arg Ile
            20                  25                  30

His Thr Gly Gln Lys Pro Phe Gln Cys Arg Ile Cys Met Arg Asn Phe
        35                  40                  45

Ser Arg Ser Asp His Leu Thr Thr His Ile Arg Thr His Thr Gly Glu
    50                  55                  60
```

```
Lys Pro Phe Ala Cys Asp Ile Cys Gly Arg Lys Phe Ala Arg Ser Asp
65                  70                  75                  80

Glu Arg Lys Arg His Thr Lys Ile His Leu Arg Gln Arg Asp Ser Arg
            85                  90                  95

Thr Ser Asp Arg Arg Gly Gly Arg Met Leu Lys His Lys Arg Gln Arg
        100                 105                 110

Asp Asp Gly Glu Gly Arg Gly Glu Val Gly Ser Ala Gly Asp Met Arg
    115                 120                 125

Ala Ala Asn Leu Trp Pro Ser Pro Leu Met Ile Lys Arg Ser Lys Lys
130                 135                 140

Asn Ser Leu Ala Leu Ser Leu Thr Ala Asp Gln Met Val Ser Ala Leu
145                 150                 155                 160

Leu Asp Ala Glu Pro Pro Ile Leu Tyr Ser Glu Tyr Asp Pro Thr Arg
                165                 170                 175

Pro Phe Ser Glu Ala Ser Met Met Gly Leu Leu Thr Asn Leu Ala Asp
            180                 185                 190

Arg Glu Leu Val His Met Ile Asn Trp Ala Lys Arg Val Pro Gly Phe
        195                 200                 205

Val Asp Leu Thr Leu His Asp Gln Val His Leu Glu Cys Ala Trp
    210                 215                 220

Leu Glu Ile Leu Met Ile Gly Leu Val Trp Arg Ser Met Glu His Pro
225                 230                 235                 240

Gly Lys Leu Leu Phe Ala Pro Asn Leu Leu Leu Asp Arg Asn Gln Gly
                245                 250                 255

Lys Cys Val Glu Gly Met Val Glu Ile Phe Asp Met Leu Leu Ala Thr
            260                 265                 270

Ser Ser Arg Phe Arg Met Met Asn Leu Gln Gly Glu Glu Phe Val Cys
        275                 280                 285

Leu Lys Ser Ile Ile Leu Leu Asn Ser Gly Val Tyr Thr Phe Leu Ser
    290                 295                 300

Ser Thr Leu Lys Ser Leu Glu Glu Lys Asp His Ile His Arg Val Leu
305                 310                 315                 320

Asp Lys Ile Thr Asp Thr Leu Ile His Leu Met Ala Lys Ala Gly Leu
                325                 330                 335

Thr Leu Gln Gln Gln His Gln Arg Leu Ala Gln Leu Leu Leu Ile Leu
            340                 345                 350

Ser His Ile Arg His Met Ser Asn Lys Gly Met Glu His Leu Tyr Ser
        355                 360                 365

Met Lys Cys Lys Asn Val Val Pro Leu Tyr Asp Leu Leu Leu Glu Met
    370                 375                 380

Leu Asp Ala His Arg Leu His Ala Pro Thr Ser Arg Thr Pro Ala Asp
385                 390                 395                 400

Ala Leu Asp Asp Phe Asp Leu Asp Met Leu Pro Ala Asp Ala Leu Asp
                405                 410                 415

Asp Phe Asp Leu Asp Met Leu Pro Ala Asp Ala Leu Asp Asp Phe Asp
            420                 425                 430

Leu Asp Met Leu Pro Gly
        435

<210> SEQ ID NO 5
<211> LENGTH: 1245
<212> TYPE: DNA
<213> ORGANISM: Artificial Sequence
<220> FEATURE:
<223> OTHER INFORMATION: Fusion of a mutated
``` human-Estrogen-receptor-ligand-binding-domain and a zinc finger
array(C7)
<220> FEATURE:
<221> NAME/KEY: CDS
<222> LOCATION: (1)..(1245)
<220> FEATURE:
<221> NAME/KEY: mutation
<222> LOCATION: (613)..(615)
<220> FEATURE:
<221> NAME/KEY: mutation
<222> LOCATION: (721)..(723)
<220> FEATURE:
<221> NAME/KEY: mutation
<222> LOCATION: (733)..(735)

<400> SEQUENCE: 5

| | | | | | | | | | | | | | | | | |
|---|---|---|---|---|---|---|---|---|---|---|---|---|---|---|---|---|
| atg | gcc | cag | gcg | gcc | ctc | gag | ccc | tat | gct | tgc | cct | gtc | gag | tcc | tgc | 48 |
| Met | Ala | Gln | Ala | Ala | Leu | Glu | Pro | Tyr | Ala | Cys | Pro | Val | Glu | Ser | Cys | |
| 1 | | | | 5 | | | | | 10 | | | | | 15 | | |
| gat | cgc | cgc | ttt | tct | aag | tcg | gct | gat | ctg | aag | cgc | cat | atc | cgc | atc | 96 |
| Asp | Arg | Arg | Phe | Ser | Lys | Ser | Ala | Asp | Leu | Lys | Arg | His | Ile | Arg | Ile | |
| | | | 20 | | | | | 25 | | | | | 30 | | | |
| cac | aca | ggc | cag | aag | cct | ttc | cag | tgt | cga | ata | tgc | atg | cgt | aac | ttc | 144 |
| His | Thr | Gly | Gln | Lys | Pro | Phe | Gln | Cys | Arg | Ile | Cys | Met | Arg | Asn | Phe | |
| | | 35 | | | | | 40 | | | | | 45 | | | | |
| agt | cgt | agt | gac | cac | ctt | acc | acc | cac | atc | cgc | acc | cac | aca | ggc | gag | 192 |
| Ser | Arg | Ser | Asp | His | Leu | Thr | Thr | His | Ile | Arg | Thr | His | Thr | Gly | Glu | |
| | 50 | | | | | 55 | | | | | 60 | | | | | |
| aag | cct | ttt | gcc | tgt | gac | att | tgt | ggg | agg | aag | ttt | gcc | agg | agt | gat | 240 |
| Lys | Pro | Phe | Ala | Cys | Asp | Ile | Cys | Gly | Arg | Lys | Phe | Ala | Arg | Ser | Asp | |
| 65 | | | | | 70 | | | | | 75 | | | | | 80 | |
| gaa | cgc | aag | agg | cat | acc | aaa | atc | cat | tta | aga | cag | agg | gac | tct | aga | 288 |
| Glu | Arg | Lys | Arg | His | Thr | Lys | Ile | His | Leu | Arg | Gln | Arg | Asp | Ser | Arg | |
| | | | | 85 | | | | | 90 | | | | | 95 | | |
| act | agt | tct | gct | gga | gac | atg | aga | gct | gcc | aac | ctt | tgg | cca | agc | ccg | 336 |
| Thr | Ser | Ser | Ala | Gly | Asp | Met | Arg | Ala | Ala | Asn | Leu | Trp | Pro | Ser | Pro | |
| | | | 100 | | | | | 105 | | | | | 110 | | | |
| ctc | atg | atc | aaa | cgc | tct | aag | aag | aac | agc | ctg | gcc | ttg | tcc | ctg | acg | 384 |
| Leu | Met | Ile | Lys | Arg | Ser | Lys | Lys | Asn | Ser | Leu | Ala | Leu | Ser | Leu | Thr | |
| | | | 115 | | | | | 120 | | | | | 125 | | | |
| gcc | gac | cag | atg | gtc | agt | gcc | ttg | ttg | gat | gct | gag | ccc | ccc | ata | ctc | 432 |
| Ala | Asp | Gln | Met | Val | Ser | Ala | Leu | Leu | Asp | Ala | Glu | Pro | Pro | Ile | Leu | |
| | | 130 | | | | | 135 | | | | | 140 | | | | |
| tat | tcc | gag | tat | gat | cct | acc | aga | ccc | ttc | agt | gaa | gct | tcg | atg | atg | 480 |
| Tyr | Ser | Glu | Tyr | Asp | Pro | Thr | Arg | Pro | Phe | Ser | Glu | Ala | Ser | Met | Met | |
| 145 | | | | | 150 | | | | | 155 | | | | | 160 | |
| ggc | tta | ctg | acc | aac | ctg | gca | gac | agg | gag | ctg | gtt | cac | atg | atc | aac | 528 |
| Gly | Leu | Leu | Thr | Asn | Leu | Ala | Asp | Arg | Glu | Leu | Val | His | Met | Ile | Asn | |
| | | | | 165 | | | | | 170 | | | | | 175 | | |
| tgg | gcg | aag | agg | gtg | cca | ggc | ttt | gtg | gat | ttg | acc | ctc | cat | gat | cag | 576 |
| Trp | Ala | Lys | Arg | Val | Pro | Gly | Phe | Val | Asp | Leu | Thr | Leu | His | Asp | Gln | |
| | | | 180 | | | | | 185 | | | | | 190 | | | |
| gtc | cac | ctt | cta | gaa | tgt | gcc | tgg | cta | gag | atc | ctg | gtg | att | ggt | ctc | 624 |
| Val | His | Leu | Leu | Glu | Cys | Ala | Trp | Leu | Glu | Ile | Leu | Val | Ile | Gly | Leu | |
| | | | 195 | | | | | 200 | | | | | 205 | | | |
| gtc | tgg | cgc | tcc | atg | gag | cac | cca | ggg | aag | cta | ctg | ttt | gct | cct | aac | 672 |
| Val | Trp | Arg | Ser | Met | Glu | His | Pro | Gly | Lys | Leu | Leu | Phe | Ala | Pro | Asn | |
| | | 210 | | | | | 215 | | | | | 220 | | | | |
| ttg | ctc | ttg | gac | agg | aac | cag | gga | aaa | tgt | gta | gag | ggc | atg | gtg | gag | 720 |
| Leu | Leu | Leu | Asp | Arg | Asn | Gln | Gly | Lys | Cys | Val | Glu | Gly | Met | Val | Glu | |
| 225 | | | | | 230 | | | | | 235 | | | | | 240 | |
| tac | ttc | gac | atg | gcc | ctg | gct | aca | tca | tct | cgg | ttc | cgc | atg | atg | aat | 768 |
| Tyr | Phe | Asp | Met | Ala | Leu | Ala | Thr | Ser | Ser | Arg | Phe | Arg | Met | Met | Asn | |

```
                   245                 250                 255
ctg cag gga gag gag ttt gtg tgc ctc aaa tct att att ttg ctt aat      816
Leu Gln Gly Glu Glu Phe Val Cys Leu Lys Ser Ile Ile Leu Leu Asn
                260                 265                 270 tct gga gtg tac aca ttt ctg tcc agc acc ctg aag tct ctg gaa gag      864
Ser Gly Val Tyr Thr Phe Leu Ser Ser Thr Leu Lys Ser Leu Glu Glu
            275                 280                 285 aag gac cat atc cac cga gtc ctg gac aag atc aca gac act ttg atc      912
Lys Asp His Ile His Arg Val Leu Asp Lys Ile Thr Asp Thr Leu Ile
        290                 295                 300 cac ctg atg gcc aag gca ggc ctg acc ctg cag cag cag cac cag cgg      960
His Leu Met Ala Lys Ala Gly Leu Thr Leu Gln Gln Gln His Gln Arg
305                 310                 315                 320 ctg gcc cag ctc ctc ctc atc ctc tcc cac atc agg cac atg agt aac     1008
Leu Ala Gln Leu Leu Leu Ile Leu Ser His Ile Arg His Met Ser Asn
                325                 330                 335 aaa ggc atg gag cat ctg tac agc atg aag tgc aag aac gtg gtg ccc     1056
Lys Gly Met Glu His Leu Tyr Ser Met Lys Cys Lys Asn Val Val Pro
            340                 345                 350 ctc tat gac ctg ctg ctg gag atg ctg gac gcc cac cgc cta cat gcg     1104
Leu Tyr Asp Leu Leu Leu Glu Met Leu Asp Ala His Arg Leu His Ala
        355                 360                 365 ccc act agc cgt acg ccg gcc gac gcc ctg gac gac ttc gac ctg gac     1152
Pro Thr Ser Arg Thr Pro Ala Asp Ala Leu Asp Asp Phe Asp Leu Asp
370                 375                 380 atg ctg ccg gcc gac gcc ctg gac gac ttc gac ctg gac atg ctg ccg     1200
Met Leu Pro Ala Asp Ala Leu Asp Asp Phe Asp Leu Asp Met Leu Pro
385                 390                 395                 400 gcc gac gcc ctg gac gac ttc gac ctg gac atg ctg ccg ggg taa         1245
Ala Asp Ala Leu Asp Asp Phe Asp Leu Asp Met Leu Pro Gly
                405                 410

<210> SEQ ID NO 6
<211> LENGTH: 414
<212> TYPE: PRT
<213> ORGANISM: Artificial Sequence
<220> FEATURE:
<223> OTHER INFORMATION: Fusion of a mutated
      human-Estrogen-receptor-ligand-binding-domain and a zinc finger
      array(C7)

<400> SEQUENCE: 6

Met Ala Gln Ala Ala Leu Glu Pro Tyr Ala Cys Pro Val Glu Ser Cys
1               5                   10                  15

Asp Arg Arg Phe Ser Lys Ser Ala Asp Leu Lys Arg His Ile Arg Ile
            20                  25                  30

His Thr Gly Gln Lys Pro Phe Gln Cys Arg Ile Cys Met Arg Asn Phe
        35                  40                  45

Ser Arg Ser Asp His Leu Thr Thr His Ile Arg Thr His Thr Gly Glu
    50                  55                  60

Lys Pro Phe Ala Cys Asp Ile Cys Gly Arg Lys Phe Ala Arg Ser Asp
65                  70                  75                  80

Glu Arg Lys Arg His Thr Lys Ile His Leu Arg Gln Arg Asp Ser Arg
                85                  90                  95

Thr Ser Ser Ala Gly Asp Met Arg Ala Ala Asn Leu Trp Pro Ser Pro
            100                 105                 110

Leu Met Ile Lys Arg Ser Lys Lys Asn Ser Leu Ala Leu Ser Leu Thr
        115                 120                 125

Ala Asp Gln Met Val Ser Ala Leu Leu Asp Ala Glu Pro Pro Ile Leu
```

-continued

```
                130                 135                 140
Tyr Ser Glu Tyr Asp Pro Thr Arg Pro Phe Ser Glu Ala Ser Met Met
145                 150                 155                 160

Gly Leu Leu Thr Asn Leu Ala Asp Arg Glu Leu Val His Met Ile Asn
                165                 170                 175

Trp Ala Lys Arg Val Pro Gly Phe Val Asp Leu Thr Leu His Asp Gln
            180                 185                 190

Val His Leu Leu Glu Cys Ala Trp Leu Glu Ile Leu Val Ile Gly Leu
        195                 200                 205

Val Trp Arg Ser Met Glu His Pro Gly Lys Leu Leu Phe Ala Pro Asn
210                 215                 220

Leu Leu Leu Asp Arg Asn Gln Gly Lys Cys Val Glu Gly Met Val Glu
225                 230                 235                 240

Tyr Phe Asp Met Ala Leu Ala Thr Ser Ser Arg Phe Arg Met Met Asn
                245                 250                 255

Leu Gln Gly Glu Glu Phe Val Cys Leu Lys Ser Ile Ile Leu Leu Asn
                260                 265                 270

Ser Gly Val Tyr Thr Phe Leu Ser Ser Thr Leu Lys Ser Leu Glu Glu
            275                 280                 285

Lys Asp His Ile His Arg Val Leu Asp Lys Ile Thr Asp Thr Leu Ile
        290                 295                 300

His Leu Met Ala Lys Ala Gly Leu Thr Leu Gln Gln His Gln Arg
305                 310                 315                 320

Leu Ala Gln Leu Leu Leu Ile Leu Ser His Ile Arg His Met Ser Asn
                325                 330                 335

Lys Gly Met Glu His Leu Tyr Ser Met Lys Cys Lys Asn Val Val Pro
                340                 345                 350

Leu Tyr Asp Leu Leu Leu Glu Met Leu Asp Ala His Arg Leu His Ala
            355                 360                 365

Pro Thr Ser Arg Thr Pro Ala Asp Ala Leu Asp Asp Phe Asp Leu Asp
        370                 375                 380

Met Leu Pro Ala Asp Ala Leu Asp Asp Phe Asp Leu Asp Met Leu Pro
385                 390                 395                 400

Ala Asp Ala Leu Asp Asp Phe Asp Leu Asp Met Leu Pro Gly
                405                 410
```

<210> SEQ ID NO 7
<211> LENGTH: 1245
<212> TYPE: DNA
<213> ORGANISM: Artificial Sequence
<220> FEATURE:
<223> OTHER INFORMATION: Fusion of a mutated
      human-Estrogen-receptor-ligand-binding-domain and a zinc finger
      array(C7)
<220> FEATURE:
<221> NAME/KEY: CDS
<222> LOCATION: (1)..(1245)
<220> FEATURE:
<221> NAME/KEY: mutation
<222> LOCATION: (712)..(714)
<220> FEATURE:
<221> NAME/KEY: mutation
<222> LOCATION: (733)..(735)

<400> SEQUENCE: 7

```
atg gcc cag gcg gcc ctc gag ccc tat gct tgc cct gtc gag tcc tgc    48
Met Ala Gln Ala Ala Leu Glu Pro Tyr Ala Cys Pro Val Glu Ser Cys
1               5                   10                  15 gat cgc cgc ttt tct aag tcg gct gat ctg aag cgc cat atc cgc atc    96
```

```
                Asp Arg Arg Phe Ser Lys Ser Ala Asp Leu Lys Arg His Ile Arg Ile
                         20                  25                  30 cac aca ggc cag aag cct ttc cag tgt cga ata tgc atg cgt aac ttc        144
His Thr Gly Gln Lys Pro Phe Gln Cys Arg Ile Cys Met Arg Asn Phe
         35                  40                  45 agt cgt agt gac cac ctt acc acc cac atc cgc acc cac aca ggc gag        192
Ser Arg Ser Asp His Leu Thr Thr His Ile Arg Thr His Thr Gly Glu
 50                  55                  60 aag cct ttt gcc tgt gac att tgt ggg agg aag ttt gcc agg agt gat        240
Lys Pro Phe Ala Cys Asp Ile Cys Gly Arg Lys Phe Ala Arg Ser Asp
 65                  70                  75                  80 gaa cgc aag agg cat acc aaa atc cat tta aga cag agg gac tct aga        288
Glu Arg Lys Arg His Thr Lys Ile His Leu Arg Gln Arg Asp Ser Arg
                     85                  90                  95 act agt tct gct gga gac atg aga gct gcc aac ctt tgg cca agc ccg        336
Thr Ser Ser Ala Gly Asp Met Arg Ala Ala Asn Leu Trp Pro Ser Pro
            100                 105                 110 ctc atg atc aaa cgc tct aag aag aac agc ctg gcc ttg tcc ctg acg        384
Leu Met Ile Lys Arg Ser Lys Lys Asn Ser Leu Ala Leu Ser Leu Thr
            115                 120                 125 gcc gac cag atg gtc agt gcc ttg ttg gat gct gag ccc ccc ata ctc        432
Ala Asp Gln Met Val Ser Ala Leu Leu Asp Ala Glu Pro Pro Ile Leu
130                 135                 140 tat tcc gag tat gat cct acc aga ccc ttc agt gaa gct tcg atg atg        480
Tyr Ser Glu Tyr Asp Pro Thr Arg Pro Phe Ser Glu Ala Ser Met Met
145                 150                 155                 160 ggc tta ctg acc aac ctg gca gac agg gag ctg gtt cac atg atc aac        528
Gly Leu Leu Thr Asn Leu Ala Asp Arg Glu Leu Val His Met Ile Asn
                165                 170                 175 tgg gcg aag agg gtg cca ggc ttt gtg gat ttg acc ctc cat gat cag        576
Trp Ala Lys Arg Val Pro Gly Phe Val Asp Leu Thr Leu His Asp Gln
            180                 185                 190 gtc cac ctt cta gaa tgt gcc tgg cta gag atc ctg atg att ggt ctc        624
Val His Leu Leu Glu Cys Ala Trp Leu Glu Ile Leu Met Ile Gly Leu
            195                 200                 205 gtc tgg cgc tcc atg gag cac cca ggg aag cta ctg ttt gct cct aac        672
Val Trp Arg Ser Met Glu His Pro Gly Lys Leu Leu Phe Ala Pro Asn
    210                 215                 220 ttg ctc ttg gac agg aac cag gga aaa tgt gta gag ggc gtg gtg gag        720
Leu Leu Leu Asp Arg Asn Gln Gly Lys Cys Val Glu Gly Val Val Glu
225                 230                 235                 240 atc ttc gac atg gcc ctg gct aca tca tct cgg ttc cgc atg atg aat        768
Ile Phe Asp Met Ala Leu Ala Thr Ser Ser Arg Phe Arg Met Met Asn
                245                 250                 255 ctg cag gga gag gag ttt gtg tgc ctc aaa tct att att ttg ctt aat        816
Leu Gln Gly Glu Glu Phe Val Cys Leu Lys Ser Ile Ile Leu Leu Asn
            260                 265                 270 tct gga gtg tac aca ttt ctg tcc agc acc ctg aag tct ctg gaa gag        864
Ser Gly Val Tyr Thr Phe Leu Ser Ser Thr Leu Lys Ser Leu Glu Glu
            275                 280                 285 aag gac cat atc cac cga gtc ctg gac aag atc aca gac act ttg atc        912
Lys Asp His Ile His Arg Val Leu Asp Lys Ile Thr Asp Thr Leu Ile
            290                 295                 300 cac ctg atg gcc aag gca ggc ctg acc ctg cag cag cag cac cag cgg        960
His Leu Met Ala Lys Ala Gly Leu Thr Leu Gln Gln Gln His Gln Arg
305                 310                 315                 320 ctg gcc cag ctc ctc ctc atc ctc tcc cac atc agg cac atg agt aac       1008
Leu Ala Gln Leu Leu Leu Ile Leu Ser His Ile Arg His Met Ser Asn
                325                 330                 335
```

```
aaa ggc atg gag cat ctg tac agc atg aag tgc aag aac gtg gtg ccc       1056
Lys Gly Met Glu His Leu Tyr Ser Met Lys Cys Lys Asn Val Val Pro
        340                 345                 350 ctc tat gac ctg ctg ctg gag atg ctg gac gcc cac cgc cta cat gcg       1104
Leu Tyr Asp Leu Leu Leu Glu Met Leu Asp Ala His Arg Leu His Ala
            355                 360                 365 ccc act agc cgt acg ccg gcc gac gcc ctg gac gac ttc gac ctg gac       1152
Pro Thr Ser Arg Thr Pro Ala Asp Ala Leu Asp Asp Phe Asp Leu Asp
370                 375                 380 atg ctg ccg gcc gac gcc ctg gac gac ttc gac ctg gac atg ctg ccg       1200
Met Leu Pro Ala Asp Ala Leu Asp Asp Phe Asp Leu Asp Met Leu Pro
385                 390                 395                 400 gcc gac gcc ctg gac gac ttc gac ctg gac atg ctg ccg ggg taa           1245
Ala Asp Ala Leu Asp Asp Phe Asp Leu Asp Met Leu Pro Gly
                405                 410

<210> SEQ ID NO 8
<211> LENGTH: 414
<212> TYPE: PRT
<213> ORGANISM: Artificial Sequence
<220> FEATURE:
<223> OTHER INFORMATION: Fusion of a mutated
      human-Estrogen-receptor-ligand-binding-domain and a zinc finger
      array(C7)

<400> SEQUENCE: 8

Met Ala Gln Ala Ala Leu Glu Pro Tyr Ala Cys Pro Val Glu Ser Cys
1               5                   10                  15

Asp Arg Arg Phe Ser Lys Ser Ala Asp Leu Lys Arg His Ile Arg Ile
            20                  25                  30

His Thr Gly Gln Lys Pro Phe Gln Cys Arg Ile Cys Met Arg Asn Phe
        35                  40                  45

Ser Arg Ser Asp His Leu Thr Thr His Ile Arg Thr His Thr Gly Glu
    50                  55                  60

Lys Pro Phe Ala Cys Asp Ile Cys Gly Arg Lys Phe Ala Arg Ser Asp
65                  70                  75                  80

Glu Arg Lys Arg His Thr Lys Ile His Leu Arg Gln Arg Asp Ser Arg
                85                  90                  95

Thr Ser Ser Ala Gly Asp Met Arg Ala Ala Asn Leu Trp Pro Ser Pro
            100                 105                 110

Leu Met Ile Lys Arg Ser Lys Lys Asn Ser Leu Ala Leu Ser Leu Thr
        115                 120                 125

Ala Asp Gln Met Val Ser Ala Leu Leu Asp Ala Glu Pro Pro Ile Leu
    130                 135                 140

Tyr Ser Glu Tyr Asp Pro Thr Arg Pro Phe Ser Glu Ala Ser Met Met
145                 150                 155                 160

Gly Leu Leu Thr Asn Leu Ala Asp Arg Glu Leu Val His Met Ile Asn
                165                 170                 175

Trp Ala Lys Arg Val Pro Gly Phe Val Asp Leu Thr Leu His Asp Gln
            180                 185                 190

Val His Leu Leu Glu Cys Ala Trp Leu Glu Ile Leu Met Ile Gly Leu
        195                 200                 205

Val Trp Arg Ser Met Glu His Pro Gly Lys Leu Leu Phe Ala Pro Asn
    210                 215                 220

Leu Leu Leu Asp Arg Asn Gln Gly Lys Cys Val Glu Gly Val Val Glu
225                 230                 235                 240

Ile Phe Asp Met Ala Leu Ala Thr Ser Ser Arg Phe Arg Met Met Asn
                245                 250                 255
```

-continued

```
Leu Gln Gly Glu Glu Phe Val Cys Leu Lys Ser Ile Ile Leu Leu Asn
            260                 265                 270

Ser Gly Val Tyr Thr Phe Leu Ser Ser Thr Leu Lys Ser Leu Glu Glu
        275                 280                 285

Lys Asp His Ile His Arg Val Leu Asp Lys Ile Thr Asp Thr Leu Ile
    290                 295                 300

His Leu Met Ala Lys Ala Gly Leu Thr Leu Gln Gln Gln His Gln Arg
305                 310                 315                 320

Leu Ala Gln Leu Leu Leu Ile Leu Ser His Ile Arg His Met Ser Asn
                325                 330                 335

Lys Gly Met Glu His Leu Tyr Ser Met Lys Cys Lys Asn Val Val Pro
            340                 345                 350

Leu Tyr Asp Leu Leu Leu Glu Met Leu Asp Ala His Arg Leu His Ala
        355                 360                 365

Pro Thr Ser Arg Thr Pro Ala Asp Ala Leu Asp Asp Phe Asp Leu Asp
    370                 375                 380

Met Leu Pro Ala Asp Ala Leu Asp Asp Phe Asp Leu Asp Met Leu Pro
385                 390                 395                 400

Ala Asp Ala Leu Asp Asp Phe Asp Leu Asp Met Leu Pro Gly
                405                 410

<210> SEQ ID NO 9
<211> LENGTH: 1245
<212> TYPE: DNA
<213> ORGANISM: Artificial Sequence
<220> FEATURE:
<223> OTHER INFORMATION: Fusion of a mutated
      human-Estrogen-receptor-ligand-binding-domain and a zinc finger
      array(C7)
<220> FEATURE:
<221> NAME/KEY: CDS
<222> LOCATION: (1)..(1245)
<220> FEATURE:
<221> NAME/KEY: mutation
<222> LOCATION: (1021)..(1023)

<400> SEQUENCE: 9 atg gcc cag gcg gcc ctc gag ccc tat gct tgc cct gtc gag tcc tgc     48
Met Ala Gln Ala Ala Leu Glu Pro Tyr Ala Cys Pro Val Glu Ser Cys
1               5                   10                  15 gat cgc cgc ttt tct aag tcg gct gat ctg aag cgc cat atc cgc atc     96
Asp Arg Arg Phe Ser Lys Ser Ala Asp Leu Lys Arg His Ile Arg Ile
            20                  25                  30 cac aca ggc cag aag cct ttc cag tgt cga ata tgc atg cgt aac ttc    144
His Thr Gly Gln Lys Pro Phe Gln Cys Arg Ile Cys Met Arg Asn Phe
        35                  40                  45 agt cgt agt gac cac ctt acc acc cac atc cgc acc cac aca ggc gag    192
Ser Arg Ser Asp His Leu Thr Thr His Ile Arg Thr His Thr Gly Glu
    50                  55                  60 aag cct ttt gcc tgt gac att tgt ggg agg aag ttt gcc agg agt gat    240
Lys Pro Phe Ala Cys Asp Ile Cys Gly Arg Lys Phe Ala Arg Ser Asp
65                  70                  75                  80 gaa cgc aag agg cat acc aaa atc cat tta aga cag agg gac tct aga    288
Glu Arg Lys Arg His Thr Lys Ile His Leu Arg Gln Arg Asp Ser Arg
                85                  90                  95 act agt tct gct gga gac atg aga gct gcc aac ctt tgg cca agc ccg    336
Thr Ser Ser Ala Gly Asp Met Arg Ala Ala Asn Leu Trp Pro Ser Pro
            100                 105                 110 ctc atg atc aaa cgc tct aag aag aac agc ctg gcc ttg tcc ctg acg    384
Leu Met Ile Lys Arg Ser Lys Lys Asn Ser Leu Ala Leu Ser Leu Thr
```

```
                 115                 120                 125
gcc gac cag atg gtc agt gcc ttg ttg gat gct gag ccc ccc ata ctc       432
Ala Asp Gln Met Val Ser Ala Leu Leu Asp Ala Glu Pro Pro Ile Leu
    130                 135                 140 tat tcc gag tat gat cct acc aga ccc ttc agt gaa gct tcg atg atg       480
Tyr Ser Glu Tyr Asp Pro Thr Arg Pro Phe Ser Glu Ala Ser Met Met
145                 150                 155                 160 ggc tta ctg acc aac ctg gca gac agg gag ctg gtt cac atg atc aac       528
Gly Leu Leu Thr Asn Leu Ala Asp Arg Glu Leu Val His Met Ile Asn
                165                 170                 175 tgg gcg aag agg gtg cca ggc ttt gtg gat ttg acc ctc cat gat cag       576
Trp Ala Lys Arg Val Pro Gly Phe Val Asp Leu Thr Leu His Asp Gln
            180                 185                 190 gtc cac ctt cta gaa tgt gcc tgg cta gag atc ctg atg att ggt ctc       624
Val His Leu Leu Glu Cys Ala Trp Leu Glu Ile Leu Met Ile Gly Leu
        195                 200                 205 gtc tgg cgc tcc atg gag cac cca ggg aag cta ctg ttt gct cct aac       672
Val Trp Arg Ser Met Glu His Pro Gly Lys Leu Leu Phe Ala Pro Asn
    210                 215                 220 ttg ctc ttg gac agg aac cag gga aaa tgt gta gag ggc atg gtg gag       720
Leu Leu Leu Asp Arg Asn Gln Gly Lys Cys Val Glu Gly Met Val Glu
225                 230                 235                 240 atc ttc gac atg ctg ctg gct aca tca tct cgg ttc cgc atg atg aat       768
Ile Phe Asp Met Leu Leu Ala Thr Ser Ser Arg Phe Arg Met Met Asn
                245                 250                 255 ctg cag gga gag gag ttt gtg tgc ctc aaa tct att att ttg ctt aat       816
Leu Gln Gly Glu Glu Phe Val Cys Leu Lys Ser Ile Ile Leu Leu Asn
            260                 265                 270 tct gga gtg tac aca ttt ctg tcc agc acc ctg aag tct ctg gaa gag       864
Ser Gly Val Tyr Thr Phe Leu Ser Ser Thr Leu Lys Ser Leu Glu Glu
        275                 280                 285 aag gac cat atc cac cga gtc ctg gac aag atc aca gac act ttg atc       912
Lys Asp His Ile His Arg Val Leu Asp Lys Ile Thr Asp Thr Leu Ile
    290                 295                 300 cac ctg atg gcc aag gca ggc ctg acc ctg cag cag cag cac cag cgg       960
His Leu Met Ala Lys Ala Gly Leu Thr Leu Gln Gln Gln His Gln Arg
305                 310                 315                 320 ctg gcc cag ctc ctc ctc atc ctc tcc cac atc agg cac atg agt aac      1008
Leu Ala Gln Leu Leu Leu Ile Leu Ser His Ile Arg His Met Ser Asn
                325                 330                 335 aaa ggc atg gag ggc ctg tac agc atg aag tgc aag aac gtg gtg ccc      1056
Lys Gly Met Glu Gly Leu Tyr Ser Met Lys Cys Lys Asn Val Val Pro
            340                 345                 350 ctc tat gac ctg ctg ctg gag atg ctg gac gcc cac cgc cta cat gcg      1104
Leu Tyr Asp Leu Leu Leu Glu Met Leu Asp Ala His Arg Leu His Ala
        355                 360                 365 ccc act agc cgt acg ccg gcc gac gcc ctg gac gac ttc gac ctg gac      1152
Pro Thr Ser Arg Thr Pro Ala Asp Ala Leu Asp Asp Phe Asp Leu Asp
    370                 375                 380 atg ctg ccg gcc gac gcc ctg gac gac ttc gac ctg gac atg ctg ccg      1200
Met Leu Pro Ala Asp Ala Leu Asp Asp Phe Asp Leu Asp Met Leu Pro
385                 390                 395                 400 gcc gac gcc ctg gac gac ttc gac ctg gac atg ctg ccg ggg taa          1245
Ala Asp Ala Leu Asp Asp Phe Asp Leu Asp Met Leu Pro Gly
                405                 410

<210> SEQ ID NO 10
<211> LENGTH: 414
<212> TYPE: PRT
<213> ORGANISM: Artificial Sequence
```

```
<220> FEATURE:
<223> OTHER INFORMATION: Fusion of a mutated
      human-Estrogen-receptor-ligand-binding-domain and a zinc finger
      array(C7)

<400> SEQUENCE: 10

Met Ala Gln Ala Ala Leu Glu Pro Tyr Ala Cys Pro Val Glu Ser Cys
1               5                   10                  15

Asp Arg Arg Phe Ser Lys Ser Ala Asp Leu Lys Arg His Ile Arg Ile
            20                  25                  30

His Thr Gly Gln Lys Pro Phe Gln Cys Arg Ile Cys Met Arg Asn Phe
        35                  40                  45

Ser Arg Ser Asp His Leu Thr Thr His Ile Arg Thr His Thr Gly Glu
    50                  55                  60

Lys Pro Phe Ala Cys Asp Ile Cys Gly Arg Lys Phe Ala Arg Ser Asp
65                  70                  75                  80

Glu Arg Lys Arg His Thr Lys Ile His Leu Arg Gln Arg Asp Ser Arg
                85                  90                  95

Thr Ser Ser Ala Gly Asp Met Arg Ala Ala Asn Leu Trp Pro Ser Pro
            100                 105                 110

Leu Met Ile Lys Arg Ser Lys Lys Asn Ser Leu Ala Leu Ser Leu Thr
        115                 120                 125

Ala Asp Gln Met Val Ser Ala Leu Leu Asp Ala Glu Pro Pro Ile Leu
    130                 135                 140

Tyr Ser Glu Tyr Asp Pro Thr Arg Pro Phe Ser Glu Ala Ser Met Met
145                 150                 155                 160

Gly Leu Leu Thr Asn Leu Ala Asp Arg Glu Leu Val His Met Ile Asn
                165                 170                 175

Trp Ala Lys Arg Val Pro Gly Phe Val Asp Leu Thr Leu His Asp Gln
            180                 185                 190

Val His Leu Leu Glu Cys Ala Trp Leu Glu Ile Leu Met Ile Gly Leu
        195                 200                 205

Val Trp Arg Ser Met Glu His Pro Gly Lys Leu Leu Phe Ala Pro Asn
    210                 215                 220

Leu Leu Leu Asp Arg Asn Gln Gly Lys Cys Val Glu Gly Met Val Glu
225                 230                 235                 240

Ile Phe Asp Met Leu Leu Ala Thr Ser Ser Arg Phe Arg Met Met Asn
                245                 250                 255

Leu Gln Gly Glu Glu Phe Val Cys Leu Lys Ser Ile Ile Leu Leu Asn
            260                 265                 270

Ser Gly Val Tyr Thr Phe Leu Ser Ser Thr Leu Lys Ser Leu Glu Glu
        275                 280                 285

Lys Asp His Ile His Arg Val Leu Asp Lys Ile Thr Asp Thr Leu Ile
    290                 295                 300

His Leu Met Ala Lys Ala Gly Leu Thr Leu Gln Gln Gln His Gln Arg
305                 310                 315                 320

Leu Ala Gln Leu Leu Leu Ile Leu Ser His Ile Arg His Met Ser Asn
                325                 330                 335

Lys Gly Met Glu Gly Leu Tyr Ser Met Lys Cys Lys Asn Val Val Pro
            340                 345                 350

Leu Tyr Asp Leu Leu Leu Glu Met Leu Asp Ala His Arg Leu His Ala
        355                 360                 365

Pro Thr Ser Arg Thr Pro Ala Asp Ala Leu Asp Asp Phe Asp Leu Asp
    370                 375                 380
```

```
Met Leu Pro Ala Asp Ala Leu Asp Asp Phe Asp Leu Asp Met Leu Pro
385                 390                 395                 400

Ala Asp Ala Leu Asp Asp Phe Asp Leu Asp Met Leu Pro Gly
                405                 410

<210> SEQ ID NO 11
<211> LENGTH: 1317
<212> TYPE: DNA
<213> ORGANISM: Artificial Sequence
<220> FEATURE:
<223> OTHER INFORMATION: Fusion of a mutated
      human-Estrogen-receptor-ligand-binding-domain and a zinc finger
      array(C7)
<220> FEATURE:
<221> NAME/KEY: CDS
<222> LOCATION: (1)..(1317)
<220> FEATURE:
<221> NAME/KEY: mutation
<222> LOCATION: (685)..(687)
<220> FEATURE:
<221> NAME/KEY: mutation
<222> LOCATION: (793)..(795)
<220> FEATURE:
<221> NAME/KEY: mutation
<222> LOCATION: (805)..(807)

<400> SEQUENCE: 11 atg gcc cag gcg gcc ctc gag ccc tat gct tgc cct gtc gag tcc tgc      48
Met Ala Gln Ala Ala Leu Glu Pro Tyr Ala Cys Pro Val Glu Ser Cys
1               5                   10                  15 gat cgc cgc ttt tct aag tcg gct gat ctg aag cgc cat atc cgc atc      96
Asp Arg Arg Phe Ser Lys Ser Ala Asp Leu Lys Arg His Ile Arg Ile
            20                  25                  30 cac aca ggc cag aag cct ttc cag tgt cga ata tgc atg cgt aac ttc     144
His Thr Gly Gln Lys Pro Phe Gln Cys Arg Ile Cys Met Arg Asn Phe
        35                  40                  45 agt cgt agt gac cac ctt acc acc cac atc cgc acc cac aca ggc gag     192
Ser Arg Ser Asp His Leu Thr Thr His Ile Arg Thr His Thr Gly Glu
    50                  55                  60 aag cct ttt gcc tgt gac att tgt ggg agg aag ttt gcc agg agt gat     240
Lys Pro Phe Ala Cys Asp Ile Cys Gly Arg Lys Phe Ala Arg Ser Asp
65                  70                  75                  80 gaa cgc aag agg cat acc aaa atc cat tta aga cag agg gac tct aga     288
Glu Arg Lys Arg His Thr Lys Ile His Leu Arg Gln Arg Asp Ser Arg
                85                  90                  95 act agt gac cga aga gga ggg aga atg ttg aaa cac aag cgc cag aga     336
Thr Ser Asp Arg Arg Gly Gly Arg Met Leu Lys His Lys Arg Gln Arg
            100                 105                 110 gat gat ggg gag ggc agg ggt gaa gtg ggg tct gct gga gac atg aga     384
Asp Asp Gly Glu Gly Arg Gly Glu Val Gly Ser Ala Gly Asp Met Arg
        115                 120                 125 gct gcc aac ctt tgg cca agc ccg ctc atg atc aaa cgc tct aag aag     432
Ala Ala Asn Leu Trp Pro Ser Pro Leu Met Ile Lys Arg Ser Lys Lys
    130                 135                 140 aac agc ctg gcc ttg tcc ctg acg gcc gac cag atg gtc agt gcc ttg     480
Asn Ser Leu Ala Leu Ser Leu Thr Ala Asp Gln Met Val Ser Ala Leu
145                 150                 155                 160 ttg gat gct gag ccc ccc ata ctc tat tcc gag tat gat cct acc aga     528
Leu Asp Ala Glu Pro Pro Ile Leu Tyr Ser Glu Tyr Asp Pro Thr Arg
                165                 170                 175 ccc ttc agt gaa gct tcg atg atg ggc tta ctg acc aac ctg gca gac     576
Pro Phe Ser Glu Ala Ser Met Met Gly Leu Leu Thr Asn Leu Ala Asp
            180                 185                 190 agg gag ctg gtt cac atg atc aac tgg gcg aag agg gtg cca ggc ttt     624
Arg Glu Leu Val His Met Ile Asn Trp Ala Lys Arg Val Pro Gly Phe
```

-continued

```
                Arg Glu Leu Val His Met Ile Asn Trp Ala Lys Arg Val Pro Gly Phe
                    195                 200                 205 gtg gat ttg acc ctc cat gat cag gtc cac ctt cta gaa tgt gcc tgg         672
Val Asp Leu Thr Leu His Asp Gln Val His Leu Leu Glu Cys Ala Trp
210                 215                 220 cta gag atc ctg gtg att ggt ctc gtc tgg cgc tcc atg gag cac cca         720
Leu Glu Ile Leu Val Ile Gly Leu Val Trp Arg Ser Met Glu His Pro
225                 230                 235                 240 ggg aag cta ctg ttt gct cct aac ttg ctc ttg gac agg aac cag gga         768
Gly Lys Leu Leu Phe Ala Pro Asn Leu Leu Leu Asp Arg Asn Gln Gly
                245                 250                 255 aaa tgt gta gag ggc atg gtg gag tac ttc gac atg gcc ctg gct aca         816
Lys Cys Val Glu Gly Met Val Glu Tyr Phe Asp Met Ala Leu Ala Thr
            260                 265                 270 tca tct cgg ttc cgc atg atg aat ctg cag gga gag gag ttt gtg tgc        864
Ser Ser Arg Phe Arg Met Met Asn Leu Gln Gly Glu Glu Phe Val Cys
        275                 280                 285 ctc aaa tct att att ttg ctt aat tct gga gtg tac aca ttt ctg tcc        912
Leu Lys Ser Ile Ile Leu Leu Asn Ser Gly Val Tyr Thr Phe Leu Ser
    290                 295                 300 agc acc ctg aag tct ctg gaa gag aag gac cat atc cac cga gtc ctg        960
Ser Thr Leu Lys Ser Leu Glu Glu Lys Asp His Ile His Arg Val Leu
305                 310                 315                 320 gac aag atc aca gac act ttg atc cac ctg atg gcc aag gca ggc ctg       1008
Asp Lys Ile Thr Asp Thr Leu Ile His Leu Met Ala Lys Ala Gly Leu
                325                 330                 335 acc ctg cag cag cag cac cag cgg ctg gcc cag ctc ctc ctc atc ctc       1056
Thr Leu Gln Gln Gln His Gln Arg Leu Ala Gln Leu Leu Leu Ile Leu
            340                 345                 350 tcc cac atc agg cac atg agt aac aaa ggc atg gag cat ctg tac agc       1104
Ser His Ile Arg His Met Ser Asn Lys Gly Met Glu His Leu Tyr Ser
        355                 360                 365 atg aag tgc aag aac gtg gtg ccc ctc tat gac ctg ctg ctg gag atg       1152
Met Lys Cys Lys Asn Val Val Pro Leu Tyr Asp Leu Leu Leu Glu Met
    370                 375                 380 ctg gac gcc cac cgc cta cat gcg ccc act agc cgt acg ccg gcc gac       1200
Leu Asp Ala His Arg Leu His Ala Pro Thr Ser Arg Thr Pro Ala Asp
385                 390                 395                 400 gcc ctg gac gac ttc gac ctg gac atg ctg ccg gcc gac gcc ctg gac       1248
Ala Leu Asp Asp Phe Asp Leu Asp Met Leu Pro Ala Asp Ala Leu Asp
                405                 410                 415 gac ttc gac ctg gac atg ctg ccg gcc gac gcc ctg gac gac ttc gac       1296
Asp Phe Asp Leu Asp Met Leu Pro Ala Asp Ala Leu Asp Asp Phe Asp
            420                 425                 430 ctg gac atg ctg ccg ggg taa                                           1317
Leu Asp Met Leu Pro Gly
        435
```

<210> SEQ ID NO 12
<211> LENGTH: 438
<212> TYPE: PRT
<213> ORGANISM: Artificial Sequence
<220> FEATURE:
<223> OTHER INFORMATION: Fusion of a mutated
    human-Estrogen-receptor-ligand-binding-domain and a zinc finger
    array(C7)

<400> SEQUENCE: 12

```
Met Ala Gln Ala Ala Leu Glu Pro Tyr Ala Cys Pro Val Glu Ser Cys
1               5                   10                  15

Asp Arg Arg Phe Ser Lys Ser Ala Asp Leu Lys Arg His Ile Arg Ile
```

```
                    20                  25                  30
His Thr Gly Gln Lys Pro Phe Gln Cys Arg Ile Cys Met Arg Asn Phe
                35                  40                  45

Ser Arg Ser Asp His Leu Thr Thr His Ile Arg Thr His Thr Gly Glu
50                  55                  60

Lys Pro Phe Ala Cys Asp Ile Cys Gly Arg Lys Phe Ala Arg Ser Asp
65                  70                  75                  80

Glu Arg Lys Arg His Thr Lys Ile His Leu Arg Gln Arg Asp Ser Arg
                85                  90                  95

Thr Ser Asp Arg Arg Gly Gly Arg Met Leu Lys His Lys Arg Gln Arg
                100                 105                 110

Asp Asp Gly Glu Gly Arg Gly Glu Val Gly Ser Ala Gly Asp Met Arg
                115                 120                 125

Ala Ala Asn Leu Trp Pro Ser Pro Leu Met Ile Lys Arg Ser Lys Lys
                130                 135                 140

Asn Ser Leu Ala Leu Ser Leu Thr Ala Asp Gln Met Val Ser Ala Leu
145                 150                 155                 160

Leu Asp Ala Glu Pro Pro Ile Leu Tyr Ser Glu Tyr Asp Pro Thr Arg
                165                 170                 175

Pro Phe Ser Glu Ala Ser Met Met Gly Leu Leu Thr Asn Leu Ala Asp
                180                 185                 190

Arg Glu Leu Val His Met Ile Asn Trp Ala Lys Arg Val Pro Gly Phe
                195                 200                 205

Val Asp Leu Thr Leu His Asp Gln Val His Leu Glu Cys Ala Trp
210                 215                 220

Leu Glu Ile Leu Val Ile Gly Leu Val Trp Arg Ser Met Glu His Pro
225                 230                 235                 240

Gly Lys Leu Leu Phe Ala Pro Asn Leu Leu Leu Asp Arg Asn Gln Gly
                245                 250                 255

Lys Cys Val Glu Gly Met Val Glu Tyr Phe Asp Met Ala Leu Ala Thr
                260                 265                 270

Ser Ser Arg Phe Arg Met Met Asn Leu Gln Gly Glu Glu Phe Val Cys
                275                 280                 285

Leu Lys Ser Ile Ile Leu Leu Asn Ser Gly Val Tyr Thr Phe Leu Ser
290                 295                 300

Ser Thr Leu Lys Ser Leu Glu Glu Lys Asp His Ile His Arg Val Leu
305                 310                 315                 320

Asp Lys Ile Thr Asp Thr Leu Ile His Leu Met Ala Lys Ala Gly Leu
                325                 330                 335

Thr Leu Gln Gln Gln His Gln Arg Leu Ala Gln Leu Leu Leu Ile Leu
                340                 345                 350

Ser His Ile Arg His Met Ser Asn Lys Gly Met Glu His Leu Tyr Ser
                355                 360                 365

Met Lys Cys Lys Asn Val Val Pro Leu Tyr Asp Leu Leu Leu Glu Met
                370                 375                 380

Leu Asp Ala His Arg Leu His Ala Pro Thr Ser Arg Thr Pro Ala Asp
385                 390                 395                 400

Ala Leu Asp Asp Phe Asp Leu Asp Met Leu Pro Ala Asp Ala Leu Asp
                405                 410                 415

Asp Phe Asp Leu Asp Met Leu Pro Ala Asp Ala Leu Asp Asp Phe Asp
                420                 425                 430

Leu Asp Met Leu Pro Gly
                435
```

<210> SEQ ID NO 13
<211> LENGTH: 1317
<212> TYPE: DNA
<213> ORGANISM: Artificial Sequence
<220> FEATURE:
<223> OTHER INFORMATION: Fusion of a mutated
   human-Estrogen-receptor-ligand-binding-domain and a zinc finger
   array(C7)
<220> FEATURE:
<221> NAME/KEY: CDS
<222> LOCATION: (1)..(1317)
<220> FEATURE:
<221> NAME/KEY: mutation
<222> LOCATION: (784)..(786)
<220> FEATURE:
<221> NAME/KEY: mutation
<222> LOCATION: (805)..(808)

<400> SEQUENCE: 13

```
atg gcc cag gcg gcc ctc gag ccc tat gct tgc cct gtc gag tcc tgc        48
Met Ala Gln Ala Ala Leu Glu Pro Tyr Ala Cys Pro Val Glu Ser Cys
1               5                  10                  15 gat cgc cgc ttt tct aag tcg gct gat ctg aag cgc cat atc cgc atc        96
Asp Arg Arg Phe Ser Lys Ser Ala Asp Leu Lys Arg His Ile Arg Ile
            20                  25                  30 cac aca ggc cag aag cct ttc cag tgt cga ata tgc atg cgt aac ttc       144
His Thr Gly Gln Lys Pro Phe Gln Cys Arg Ile Cys Met Arg Asn Phe
        35                  40                  45 agt cgt agt gac cac ctt acc acc cac atc cgc acc cac aca ggc gag       192
Ser Arg Ser Asp His Leu Thr Thr His Ile Arg Thr His Thr Gly Glu
    50                  55                  60 aag cct ttt gcc tgt gac att tgt ggg agg aag ttt gcc agg agt gat       240
Lys Pro Phe Ala Cys Asp Ile Cys Gly Arg Lys Phe Ala Arg Ser Asp
65                  70                  75                  80 gaa cgc aag agg cat acc aaa atc cat tta aga cag agg gac tct aga       288
Glu Arg Lys Arg His Thr Lys Ile His Leu Arg Gln Arg Asp Ser Arg
                85                  90                  95 act agt gac cga aga gga ggg aga atg ttg aaa cac aag cgc cag aga       336
Thr Ser Asp Arg Arg Gly Gly Arg Met Leu Lys His Lys Arg Gln Arg
            100                 105                 110 gat gat ggg gag ggc agg ggt gaa gtg ggg tct gct gga gac atg aga       384
Asp Asp Gly Glu Gly Arg Gly Glu Val Gly Ser Ala Gly Asp Met Arg
        115                 120                 125 gct gcc aac ctt tgg cca agc ccg ctc atg atc aaa cgc tct aag aag       432
Ala Ala Asn Leu Trp Pro Ser Pro Leu Met Ile Lys Arg Ser Lys Lys
    130                 135                 140 aac agc ctg gcc ttg tcc ctg acg gcc gac cag atg gtc agt gcc ttg       480
Asn Ser Leu Ala Leu Ser Leu Thr Ala Asp Gln Met Val Ser Ala Leu
145                 150                 155                 160 ttg gat gct gag ccc ccc ata ctc tat tcc gag tat gat cct acc aga       528
Leu Asp Ala Glu Pro Pro Ile Leu Tyr Ser Glu Tyr Asp Pro Thr Arg
                165                 170                 175 ccc ttc agt gaa gct tcg atg atg ggc tta ctg acc aac ctg gca gac       576
Pro Phe Ser Glu Ala Ser Met Met Gly Leu Leu Thr Asn Leu Ala Asp
            180                 185                 190 agg gag ctg gtt cac atg atc aac tgg gcg aag agg gtg cca ggc ttt       624
Arg Glu Leu Val His Met Ile Asn Trp Ala Lys Arg Val Pro Gly Phe
        195                 200                 205 gtg gat ttg acc ctc cat gat cag gtc cac ctt cta gaa tgt gcc tgg       672
Val Asp Leu Thr Leu His Asp Gln Val His Leu Leu Glu Cys Ala Trp
    210                 215                 220 cta gag atc ctg atg att ggt ctc gtc tgg cgc tcc atg gag cac cca       720
Leu Glu Ile Leu Met Ile Gly Leu Val Trp Arg Ser Met Glu His Pro
```

```
Leu Glu Ile Leu Met Ile Gly Leu Val Trp Arg Ser Met Glu His Pro
225                 230                 235                 240 ggg aag cta ctg ttt gct cct aac ttg ctc ttg gac agg aac cag gga      768
Gly Lys Leu Leu Phe Ala Pro Asn Leu Leu Leu Asp Arg Asn Gln Gly
                245                 250                 255 aaa tgt gta gag ggc gtg gtg gag atc ttc gac atg gcc ctg gct aca      816
Lys Cys Val Glu Gly Val Val Glu Ile Phe Asp Met Ala Leu Ala Thr
            260                 265                 270 tca tct cgg ttc cgc atg atg aat ctg cag gga gag gag ttt gtg tgc      864
Ser Ser Arg Phe Arg Met Met Asn Leu Gln Gly Glu Glu Phe Val Cys
        275                 280                 285 ctc aaa tct att att ttg ctt aat tct gga gtg tac aca ttt ctg tcc      912
Leu Lys Ser Ile Ile Leu Leu Asn Ser Gly Val Tyr Thr Phe Leu Ser
    290                 295                 300 agc acc ctg aag tct ctg gaa gag aag gac cat atc cac cga gtc ctg      960
Ser Thr Leu Lys Ser Leu Glu Glu Lys Asp His Ile His Arg Val Leu
305                 310                 315                 320 gac aag atc aca gac act ttg atc cac ctg atg gcc aag gca ggc ctg     1008
Asp Lys Ile Thr Asp Thr Leu Ile His Leu Met Ala Lys Ala Gly Leu
                325                 330                 335 acc ctg cag cag cag cac cag cgg ctg gcc cag ctc ctc ctc atc ctc     1056
Thr Leu Gln Gln Gln His Gln Arg Leu Ala Gln Leu Leu Leu Ile Leu
            340                 345                 350 tcc cac atc agg cac atg agt aac aaa ggc atg gag cat ctg tac agc     1104
Ser His Ile Arg His Met Ser Asn Lys Gly Met Glu His Leu Tyr Ser
        355                 360                 365 atg aag tgc aag aac gtg gtg ccc ctc tat gac ctg ctg ctg gag atg     1152
Met Lys Cys Lys Asn Val Val Pro Leu Tyr Asp Leu Leu Leu Glu Met
    370                 375                 380 ctg gac gcc cac cgc cta cat gcg ccc act agc cgt acg ccg gcc gac     1200
Leu Asp Ala His Arg Leu His Ala Pro Thr Ser Arg Thr Pro Ala Asp
385                 390                 395                 400 gcc ctg gac gac ttc gac ctg gac atg ctg ccg gcc gac gcc ctg gac     1248
Ala Leu Asp Asp Phe Asp Leu Asp Met Leu Pro Ala Asp Ala Leu Asp
                405                 410                 415 gac ttc gac ctg gac atg ctg ccg gcc gac gcc ctg gac gac ttc gac     1296
Asp Phe Asp Leu Asp Met Leu Pro Ala Asp Ala Leu Asp Asp Phe Asp
            420                 425                 430 ctg gac atg ctg ccg ggg taa                                         1317
Leu Asp Met Leu Pro Gly
        435

<210> SEQ ID NO 14
<211> LENGTH: 438
<212> TYPE: PRT
<213> ORGANISM: Artificial Sequence
<220> FEATURE:
<223> OTHER INFORMATION: Fusion of a mutated
      human-Estrogen-receptor-ligand-binding-domain and a zinc finger
      array(C7)

<400> SEQUENCE: 14

Met Ala Gln Ala Ala Leu Glu Pro Tyr Ala Cys Pro Val Glu Ser Cys
1               5                   10                  15

Asp Arg Arg Phe Ser Lys Ser Ala Asp Leu Lys Arg His Ile Arg Ile
            20                  25                  30

His Thr Gly Gln Lys Pro Phe Gln Cys Arg Ile Cys Met Arg Asn Phe
        35                  40                  45

Ser Arg Ser Asp His Leu Thr Thr His Ile Arg Thr His Thr Gly Glu
    50                  55                  60
```

```
Lys Pro Phe Ala Cys Asp Ile Cys Gly Arg Lys Phe Ala Arg Ser Asp
 65                  70                  75                  80

Glu Arg Lys Arg His Thr Lys Ile His Leu Arg Gln Arg Asp Ser Arg
                 85                  90                  95

Thr Ser Asp Arg Arg Gly Gly Arg Met Leu Lys His Lys Arg Gln Arg
            100                 105                 110

Asp Asp Gly Glu Gly Arg Gly Glu Val Gly Ser Ala Gly Asp Met Arg
        115                 120                 125

Ala Ala Asn Leu Trp Pro Ser Pro Leu Met Ile Lys Arg Ser Lys Lys
    130                 135                 140

Asn Ser Leu Ala Leu Ser Leu Thr Ala Asp Gln Met Val Ser Ala Leu
145                 150                 155                 160

Leu Asp Ala Glu Pro Pro Ile Leu Tyr Ser Glu Tyr Asp Pro Thr Arg
                165                 170                 175

Pro Phe Ser Glu Ala Ser Met Met Gly Leu Leu Thr Asn Leu Ala Asp
            180                 185                 190

Arg Glu Leu Val His Met Ile Asn Trp Ala Lys Arg Val Pro Gly Phe
        195                 200                 205

Val Asp Leu Thr Leu His Asp Gln Val His Leu Leu Glu Cys Ala Trp
    210                 215                 220

Leu Glu Ile Leu Met Ile Gly Leu Val Trp Arg Ser Met Glu His Pro
225                 230                 235                 240

Gly Lys Leu Leu Phe Ala Pro Asn Leu Leu Leu Asp Arg Asn Gln Gly
                245                 250                 255

Lys Cys Val Glu Gly Val Val Glu Ile Phe Asp Met Ala Leu Ala Thr
            260                 265                 270

Ser Ser Arg Phe Arg Met Met Asn Leu Gln Gly Glu Glu Phe Val Cys
        275                 280                 285

Leu Lys Ser Ile Ile Leu Leu Asn Ser Gly Val Tyr Thr Phe Leu Ser
    290                 295                 300

Ser Thr Leu Lys Ser Leu Glu Glu Lys Asp His Ile His Arg Val Leu
305                 310                 315                 320

Asp Lys Ile Thr Asp Thr Leu Ile His Leu Met Ala Lys Ala Gly Leu
                325                 330                 335

Thr Leu Gln Gln Gln His Gln Arg Leu Ala Gln Leu Leu Leu Ile Leu
            340                 345                 350

Ser His Ile Arg His Met Ser Asn Lys Gly Met Glu His Leu Tyr Ser
    355                 360                 365

Met Lys Cys Lys Asn Val Val Pro Leu Tyr Asp Leu Leu Leu Glu Met
    370                 375                 380

Leu Asp Ala His Arg Leu His Ala Pro Thr Ser Arg Thr Pro Ala Asp
385                 390                 395                 400

Ala Leu Asp Asp Phe Asp Leu Asp Met Leu Pro Ala Asp Ala Leu Asp
                405                 410                 415

Asp Phe Asp Leu Asp Met Leu Pro Ala Asp Ala Leu Asp Asp Phe Asp
            420                 425                 430

Leu Asp Met Leu Pro Gly
            435

<210> SEQ ID NO 15
<211> LENGTH: 1317
<212> TYPE: DNA
<213> ORGANISM: Artificial Sequence
<220> FEATURE:
<223> OTHER INFORMATION: Fusion of a mutated
```

-continued human-Estrogen-receptor-ligand-binding-domain and a zinc finger
array(C7)
<220> FEATURE:
<221> NAME/KEY: CDS
<222> LOCATION: (1)..(1317)
<220> FEATURE:
<221> NAME/KEY: mutation
<222> LOCATION: (1093)..(1095)

<400> SEQUENCE: 15

```
atg gcc cag gcg gcc ctc gag ccc tat gct tgc cct gtc gag tcc tgc         48
Met Ala Gln Ala Ala Leu Glu Pro Tyr Ala Cys Pro Val Glu Ser Cys
1               5                   10                  15 gat cgc cgc ttt tct aag tcg gct gat ctg aag cgc cat atc cgc atc         96
Asp Arg Arg Phe Ser Lys Ser Ala Asp Leu Lys Arg His Ile Arg Ile
                20                  25                  30 cac aca ggc cag aag cct ttc cag tgt cga ata tgc atg cgt aac ttc        144
His Thr Gly Gln Lys Pro Phe Gln Cys Arg Ile Cys Met Arg Asn Phe
            35                  40                  45 agt cgt agt gac cac ctt acc acc cac atc cgc acc cac aca ggc gag        192
Ser Arg Ser Asp His Leu Thr Thr His Ile Arg Thr His Thr Gly Glu
    50                  55                  60 aag cct ttt gcc tgt gac att tgt ggg agg aag ttt gcc agg agt gat        240
Lys Pro Phe Ala Cys Asp Ile Cys Gly Arg Lys Phe Ala Arg Ser Asp
65                  70                  75                  80 gaa cgc aag agg cat acc aaa atc cat tta aga cag agg gac tct aga        288
Glu Arg Lys Arg His Thr Lys Ile His Leu Arg Gln Arg Asp Ser Arg
                85                  90                  95 act agt gac cga aga gga ggg aga atg ttg aaa cac aag cgc cag aga        336
Thr Ser Asp Arg Arg Gly Gly Arg Met Leu Lys His Lys Arg Gln Arg
                100                 105                 110 gat gat ggg gag ggc agg ggt gaa gtg ggg tct gct gga gac atg aga        384
Asp Asp Gly Glu Gly Arg Gly Glu Val Gly Ser Ala Gly Asp Met Arg
            115                 120                 125 gct gcc aac ctt tgg cca agc ccg ctc atg atc aaa cgc tct aag aag        432
Ala Ala Asn Leu Trp Pro Ser Pro Leu Met Ile Lys Arg Ser Lys Lys
        130                 135                 140 aac agc ctg gcc ttg tcc ctg acg gcc gac cag atg gtc agt gcc ttg        480
Asn Ser Leu Ala Leu Ser Leu Thr Ala Asp Gln Met Val Ser Ala Leu
145                 150                 155                 160 ttg gat gct gag ccc ccc ata ctc tat tcc gag tat gat cct acc aga        528
Leu Asp Ala Glu Pro Pro Ile Leu Tyr Ser Glu Tyr Asp Pro Thr Arg
                165                 170                 175 ccc ttc agt gaa gct tcg atg atg ggc tta ctg acc aac ctg gca gac        576
Pro Phe Ser Glu Ala Ser Met Met Gly Leu Leu Thr Asn Leu Ala Asp
                180                 185                 190 agg gag ctg gtt cac atg atc aac tgg gcg aag agg gtg cca ggc ttt        624
Arg Glu Leu Val His Met Ile Asn Trp Ala Lys Arg Val Pro Gly Phe
            195                 200                 205 gtg gat ttg acc ctc cat gat cag gtc cac ctt cta gaa tgt gcc tgg        672
Val Asp Leu Thr Leu His Asp Gln Val His Leu Leu Glu Cys Ala Trp
        210                 215                 220 cta gag atc ctg atg att ggt ctc gtc tgg cgc tcc atg gag cac cca        720
Leu Glu Ile Leu Met Ile Gly Leu Val Trp Arg Ser Met Glu His Pro
225                 230                 235                 240 ggg aag cta ctg ttt gct cct aac ttg ctc ttg gac agg aac cag gga        768
Gly Lys Leu Leu Phe Ala Pro Asn Leu Leu Leu Asp Arg Asn Gln Gly
                245                 250                 255 aaa tgt gta gag ggc atg gtg gag atc ttc gac atg ctg ctg gct aca        816
Lys Cys Val Glu Gly Met Val Glu Ile Phe Asp Met Leu Leu Ala Thr
                260                 265                 270
```

-continued

```
tca tct cgg ttc cgc atg atg aat ctg cag gga gag gag ttt gtg tgc      864
Ser Ser Arg Phe Arg Met Met Asn Leu Gln Gly Glu Glu Phe Val Cys
        275                 280                 285 ctc aaa tct att att ttg ctt aat tct gga gtg tac aca ttt ctg tcc      912
Leu Lys Ser Ile Ile Leu Leu Asn Ser Gly Val Tyr Thr Phe Leu Ser
    290                 295                 300 agc acc ctg aag tct ctg gaa gag aag gac cat atc cac cga gtc ctg      960
Ser Thr Leu Lys Ser Leu Glu Glu Lys Asp His Ile His Arg Val Leu
305                 310                 315                 320 gac aag atc aca gac act ttg atc cac ctg atg gcc aag gca ggc ctg     1008
Asp Lys Ile Thr Asp Thr Leu Ile His Leu Met Ala Lys Ala Gly Leu
                325                 330                 335 acc ctg cag cag cag cac cag cgg ctg gcc cag ctc ctc ctc atc ctc     1056
Thr Leu Gln Gln Gln His Gln Arg Leu Ala Gln Leu Leu Leu Ile Leu
            340                 345                 350 tcc cac atc agg cac atg agt aac aaa ggc atg gag ggc ctg tac agc     1104
Ser His Ile Arg His Met Ser Asn Lys Gly Met Glu Gly Leu Tyr Ser
        355                 360                 365 atg aag tgc aag aac gtg gtg ccc ctc tat gac ctg ctg ctg gag atg     1152
Met Lys Cys Lys Asn Val Val Pro Leu Tyr Asp Leu Leu Leu Glu Met
    370                 375                 380 ctg gac gcc cac cgc cta cat gcg ccc act agc cgt acg ccg gcc gac     1200
Leu Asp Ala His Arg Leu His Ala Pro Thr Ser Arg Thr Pro Ala Asp
385                 390                 395                 400 gcc ctg gac gac ttc gac ctg gac atg ctg ccg gcc gac gcc ctg gac     1248
Ala Leu Asp Asp Phe Asp Leu Asp Met Leu Pro Ala Asp Ala Leu Asp
                405                 410                 415 gac ttc gac ctg gac atg ctg ccg gcc gac gcc ctg gac gac ttc gac     1296
Asp Phe Asp Leu Asp Met Leu Pro Ala Asp Ala Leu Asp Asp Phe Asp
            420                 425                 430 ctg gac atg ctg ccg ggg taa                                          1317
Leu Asp Met Leu Pro Gly
        435
```

<210> SEQ ID NO 16
<211> LENGTH: 438
<212> TYPE: PRT
<213> ORGANISM: Artificial Sequence
<220> FEATURE:
<223> OTHER INFORMATION: Fusion of a mutated
      human-Estrogen-receptor-ligand-binding-domain and a zinc finger
      array(C7)

<400> SEQUENCE: 16

```
Met Ala Gln Ala Ala Leu Glu Pro Tyr Ala Cys Pro Val Glu Ser Cys
1               5                   10                  15

Asp Arg Arg Phe Ser Lys Ser Ala Asp Leu Lys Arg His Ile Arg Ile
            20                  25                  30

His Thr Gly Gln Lys Pro Phe Gln Cys Arg Ile Cys Met Arg Asn Phe
        35                  40                  45

Ser Arg Ser Asp His Leu Thr Thr His Ile Arg Thr His Thr Gly Glu
    50                  55                  60

Lys Pro Phe Ala Cys Asp Ile Cys Gly Arg Lys Phe Ala Arg Ser Asp
65                  70                  75                  80

Glu Arg Lys Arg His Thr Lys Ile His Leu Arg Gln Arg Asp Ser Arg
                85                  90                  95

Thr Ser Asp Arg Arg Gly Gly Arg Met Leu Lys His Lys Arg Gln Arg
            100                 105                 110

Asp Asp Gly Glu Gly Arg Gly Glu Val Gly Ser Ala Gly Asp Met Arg
        115                 120                 125
```

```
Ala Ala Asn Leu Trp Pro Ser Pro Leu Met Ile Lys Arg Ser Lys Lys
    130                 135                 140

Asn Ser Leu Ala Leu Ser Leu Thr Ala Asp Gln Met Val Ser Ala Leu
145                 150                 155                 160

Leu Asp Ala Glu Pro Pro Ile Leu Tyr Ser Glu Tyr Asp Pro Thr Arg
                165                 170                 175

Pro Phe Ser Glu Ala Ser Met Met Gly Leu Leu Thr Asn Leu Ala Asp
                180                 185                 190

Arg Glu Leu Val His Met Ile Asn Trp Ala Lys Arg Val Pro Gly Phe
            195                 200                 205

Val Asp Leu Thr Leu His Asp Gln Val His Leu Leu Glu Cys Ala Trp
    210                 215                 220

Leu Glu Ile Leu Met Ile Gly Leu Val Trp Arg Ser Met Glu His Pro
225                 230                 235                 240

Gly Lys Leu Leu Phe Ala Pro Asn Leu Leu Asp Arg Asn Gln Gly
                245                 250                 255

Lys Cys Val Glu Gly Met Val Glu Ile Phe Asp Met Leu Leu Ala Thr
                260                 265                 270

Ser Ser Arg Phe Arg Met Met Asn Leu Gln Gly Glu Glu Phe Val Cys
            275                 280                 285

Leu Lys Ser Ile Ile Leu Leu Asn Ser Gly Val Tyr Thr Phe Leu Ser
    290                 295                 300

Ser Thr Leu Lys Ser Leu Glu Glu Lys Asp His Ile His Arg Val Leu
305                 310                 315                 320

Asp Lys Ile Thr Asp Thr Leu Ile His Leu Met Ala Lys Ala Gly Leu
                325                 330                 335

Thr Leu Gln Gln Gln His Gln Arg Leu Ala Gln Leu Leu Leu Ile Leu
            340                 345                 350

Ser His Ile Arg His Met Ser Asn Lys Gly Met Glu Gly Leu Tyr Ser
    355                 360                 365

Met Lys Cys Lys Asn Val Val Pro Leu Tyr Asp Leu Leu Leu Glu Met
370                 375                 380

Leu Asp Ala His Arg Leu His Ala Pro Thr Ser Arg Thr Pro Ala Asp
385                 390                 395                 400

Ala Leu Asp Asp Phe Asp Leu Asp Met Leu Pro Ala Asp Ala Leu Asp
                405                 410                 415

Asp Phe Asp Leu Asp Met Leu Pro Ala Asp Ala Leu Asp Phe Asp
                420                 425                 430

Leu Asp Met Leu Pro Gly
            435

<210> SEQ ID NO 17
<211> LENGTH: 44
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(44)

<400> SEQUENCE: 17
gtagagggcg tggtggagat cttcgacatg gccctggcta catc                    44

<210> SEQ ID NO 18
<211> LENGTH: 44
```

```
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(44)

<400> SEQUENCE: 18
gatgtagcca gggccatgtc gaagatctcc accacgccct ctac                    44

<210> SEQ ID NO 19
<211> LENGTH: 28
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(28)

<400> SEQUENCE: 19
gctagagatc ctggtgattg gtctcgtc                                      28

<210> SEQ ID NO 20
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 20
ggcatggtgg agtacttcga catggcc                                       27

<210> SEQ ID NO 21
<211> LENGTH: 30
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(30)

<400> SEQUENCE: 21
gatcttcgac atggccctgg ctacatcatc                                    30

<210> SEQ ID NO 22
<211> LENGTH: 28
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(28)

<400> SEQUENCE: 22
ggcatggtgg aggccttcga catggtgc                                      28

<210> SEQ ID NO 23
<211> LENGTH: 28
<212> TYPE: DNA
<213> ORGANISM: Artificial Sequence
<220> FEATURE:
<223> OTHER INFORMATION: Oligo for mutagenesis
```

```
<220> FEATURE:
<221> NAME/KEY: primer_bind
<222> LOCATION: (1)..(28)

<400> SEQUENCE: 23
ggcatggtgg agttcttcga catggtgc                                              28

<210> SEQ ID NO 24
<211> LENGTH: 28
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(28)

<400> SEQUENCE: 24
ggcatggtgg agatgttcga catggtgc                                              28

<210> SEQ ID NO 25
<211> LENGTH: 28
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(28)

<400> SEQUENCE: 25
ggcatggtgg aggccttcga catggccc                                              28

<210> SEQ ID NO 26
<211> LENGTH: 28
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(28)

<400> SEQUENCE: 26
ggcatggtgg agttcttcga catggccc                                              28

<210> SEQ ID NO 27
<211> LENGTH: 28
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(28)

<400> SEQUENCE: 27
ggcatggtgg agatgttcga catggccc                                              28

<210> SEQ ID NO 28
<211> LENGTH: 28
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(28)
```

```
<400> SEQUENCE: 28
gctagagatc ctggccattg gtctcgtc                                        28

<210> SEQ ID NO 29
<211> LENGTH: 28
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(28)

<400> SEQUENCE: 29
gctagagatc ctgttcattg gtctcgtc                                        28

<210> SEQ ID NO 30
<211> LENGTH: 28
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(28)

<400> SEQUENCE: 30
gctagagatc ctggtgattg gtctcgtc                                        28

<210> SEQ ID NO 31
<211> LENGTH: 28
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(28)

<400> SEQUENCE: 31
gctagagatc ctgtggattg gtctcgtc                                        28

<210> SEQ ID NO 32
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 32
ggcatggtgg agttcttcga catggcc                                         27

<210> SEQ ID NO 33
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 33
ggccatgtcg aagaactcca ccatgcc                                         27
```

```
<210> SEQ ID NO 34
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 34
ggcatggtgg agctgttcga catggcc                                      27

<210> SEQ ID NO 35
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 35
ggccatgtcg aacagctcca ccatgcc                                      27

<210> SEQ ID NO 36
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 36
ggcatggtgg agatgttcga catggcc                                      27

<210> SEQ ID NO 37
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 37
ggccatgtcg aacatctcca ccatgcc                                      27

<210> SEQ ID NO 38
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 38
ggcatggtgg aggtgttcga catggcc                                      27

<210> SEQ ID NO 39
<211> LENGTH: 27
<212> TYPE: DNA
```

<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 39
ggccatgtcg aacacctcca ccatgcc        27

<210> SEQ ID NO 40
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 40
ggcatggtgg agtacttcga catggcc        27

<210> SEQ ID NO 41
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 41
ggccatgtcg aagtactcca ccatgcc        27

<210> SEQ ID NO 42
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 42
ggcgtggtgg agttcttcga catggcc        27

<210> SEQ ID NO 43
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(26)

<400> SEQUENCE: 43
ggccatgtcg aagaactcca ccacgcc        27

<210> SEQ ID NO 44
<211> LENGTH: 27
<212> TYPE: DNA
<213> ORGANISM: Artificial Sequence
<220> FEATURE:
<223> OTHER INFORMATION: Oligo for mutagenesis
<220> FEATURE:

```
<221> NAME/KEY: primer_bind
<222> LOCATION: (1)..(27)

<400> SEQUENCE: 44
ggcgtggtgg agctgttcga catggcc                                              27

<210> SEQ ID NO 45
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 45
ggccatgtcg aacagctcca ccacgcc                                              27

<210> SEQ ID NO 46
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 46
ggcgtggtgg agatgttcga catggcc                                              27

<210> SEQ ID NO 47
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 47
ggccatgtcg aacatctcca ccacgcc                                              27

<210> SEQ ID NO 48
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 48
ggcgtggtgg aggtgttcga catggcc                                              27

<210> SEQ ID NO 49
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 49
```
ggccatgtcg aacacctcca ccacgcc                                          27

<210> SEQ ID NO 50
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 50
ggcgtggtgg agtacttcga catggcc                                          27

<210> SEQ ID NO 51
<211> LENGTH: 27
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(27)

<400> SEQUENCE: 51
ggccatgtcg aagtactcca ccacgcc                                          27

<210> SEQ ID NO 52
<211> LENGTH: 26
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(26)

<400> SEQUENCE: 52
gcatggaggg cctgtacagc atgaag                                           26

<210> SEQ ID NO 53
<211> LENGTH: 26
<212> TYPE: DNA
<213> ORGANISM: Artificial Sequence
<220> FEATURE:
<223> OTHER INFORMATION: Oligo for mutagenesis
<220> FEATURE:
<221> NAME/KEY: primer_bind
<222> LOCATION: (1)..(26)

<400> SEQUENCE: 53
cttcatgctg tacaggccct ccatgc                                           26

<210> SEQ ID NO 54
<211> LENGTH: 2092
<212> TYPE: DNA
<213> ORGANISM: Homo sapiens
<220> FEATURE:
<221> NAME/KEY: CDS
<222> LOCATION: (293)..(2080)
<223> OTHER INFORMATION:
<220> FEATURE:
<221> NAME/KEY: misc_feature
<222> LOCATION: (293)..(832)
<223> OTHER INFORMATION: A/B domain
<220> FEATURE:
<221> NAME/KEY: misc_feature
<222> LOCATION: (833)..(1081)

```
<223> OTHER INFORMATION: C domain
<220> FEATURE:
<221> NAME/KEY: misc_feature
<222> LOCATION: (1082)..(1198)
<223> OTHER INFORMATION: D domain
<220> FEATURE:
<221> NAME/KEY: misc_feature
<222> LOCATION: (1199)..(1954)
<223> OTHER INFORMATION: E domain
<220> FEATURE:
<221> NAME/KEY: misc_feature
<222> LOCATION: (1955)..(2077)
<223> OTHER INFORMATION: F domain

<400> SEQUENCE: 54
```

| | | |
|---|---|---|
| gaattccaaa attgtgatgt ttcttgtatt tttgatgaag gagaaatact gtaatgatca | 60 | |
| ctgtttacac tatgtacact ttaggccagc cctttgtagc gttatacaaa ctgaaagcac | 120 | |
| accggacccg caggctcccg gggcagggcc ggggccagag ctcgcgtgtc ggcgggacat | 180 | |
| gcgctgcgtc gcctctaacc tcgggctgtg ctctttttcc aggtggcccg ccggtttctg | 240 | |
| agccttctgc cctgcgggga cacggtctgc accctgcccg cggccacgga cc atg acc | 298 | |
|                                                                                                                                                               Met Thr | | |
|                                                                                                                                                               1 | | |

```
atg acc ctc cac acc aaa gca tct ggg atg gcc cta ctg cat cag atc     346
Met Thr Leu His Thr Lys Ala Ser Gly Met Ala Leu Leu His Gln Ile
        5                  10                  15 caa ggg aac gag ctg gag ccc ctg aac cgt ccg cag ctc aag atc ccc     394
Gln Gly Asn Glu Leu Glu Pro Leu Asn Arg Pro Gln Leu Lys Ile Pro
 20                  25                  30 ctg gag cgg ccc ctg ggc gag gtg tac ctg gac agc agc aag ccc gcc     442
Leu Glu Arg Pro Leu Gly Glu Val Tyr Leu Asp Ser Ser Lys Pro Ala
35                  40                  45                  50 gtg tac aac tac ccc gag ggc gcc gcc tac gag ttc aac gcc gcg gcc     490
Val Tyr Asn Tyr Pro Glu Gly Ala Ala Tyr Glu Phe Asn Ala Ala Ala
                 55                  60                  65 gcc gcc aac gcg cag gtc tac ggt cag acc ggc ctc ccc tac ggc ccc     538
Ala Ala Asn Ala Gln Val Tyr Gly Gln Thr Gly Leu Pro Tyr Gly Pro
             70                  75                  80 ggg tct gag gct gcg gcg ttc ggc tcc aac ggc ctg ggg ggt ttc ccc     586
Gly Ser Glu Ala Ala Ala Phe Gly Ser Asn Gly Leu Gly Gly Phe Pro
         85                  90                  95 cca ctc aac agc gtg tct ccg agc ccg ctg atg cta ctg cac ccg ccg     634
Pro Leu Asn Ser Val Ser Pro Ser Pro Leu Met Leu Leu His Pro Pro
    100                 105                 110 ccg cag ctg tcg cct ttc ctg cag ccc cac ggc cag cag gtg ccc tac     682
Pro Gln Leu Ser Pro Phe Leu Gln Pro His Gly Gln Gln Val Pro Tyr
115                 120                 125                 130 tac ctg gag aac gag ccc agc ggc tac acg gtg cgc gag gcc ggc ccg     730
Tyr Leu Glu Asn Glu Pro Ser Gly Tyr Thr Val Arg Glu Ala Gly Pro
                135                 140                 145 ccg gca ttc tac agg cca aat tca gat aat cga cgc cag ggt ggc aga     778
Pro Ala Phe Tyr Arg Pro Asn Ser Asp Asn Arg Arg Gln Gly Gly Arg
            150                 155                 160 gaa aga ttg gcc agt acc aat gac aag gga agt atg gct atg gaa tct     826
Glu Arg Leu Ala Ser Thr Asn Asp Lys Gly Ser Met Ala Met Glu Ser
        165                 170                 175 gcc aag gag act cgc tac tgt gca gtg tgc aat gac tat gct tca ggc     874
Ala Lys Glu Thr Arg Tyr Cys Ala Val Cys Asn Asp Tyr Ala Ser Gly
    180                 185                 190 tac cat tat gga gtc tgg tcc tgt gag ggc tgc aag gcc ttc ttc aag     922
Tyr His Tyr Gly Val Trp Ser Cys Glu Gly Cys Lys Ala Phe Phe Lys
195                 200                 205                 210
```

| | | |
|---|---|---|
| aga agt att caa gga cat aac gac tat atg tgt cca gcc acc aac cag<br>Arg Ser Ile Gln Gly His Asn Asp Tyr Met Cys Pro Ala Thr Asn Gln<br>215 220 225 | | 970 |
| tgc acc att gat aaa aac agg agg aag agc tgc cag gcc tgc cgg ctc<br>Cys Thr Ile Asp Lys Asn Arg Arg Lys Ser Cys Gln Ala Cys Arg Leu<br>230 235 240 | | 1018 |
| cgc aaa tgc tac gaa gtg gga atg atg aaa ggt ggg ata cga aaa gac<br>Arg Lys Cys Tyr Glu Val Gly Met Met Lys Gly Gly Ile Arg Lys Asp<br>245 250 255 | | 1066 |
| cga aga gga ggg aga atg ttg aaa cac aag cgc cag aga gat gat ggg<br>Arg Arg Gly Gly Arg Met Leu Lys His Lys Arg Gln Arg Asp Asp Gly<br>260 265 270 | | 1114 |
| gag ggc agg ggt gaa gtg ggg tct gct gga gac atg aga gct gcc aac<br>Glu Gly Arg Gly Glu Val Gly Ser Ala Gly Asp Met Arg Ala Ala Asn<br>275 280 285 290 | | 1162 |
| ctt tgg cca agc ccg ctc atg atc aaa cgc tct aag aag aac agc ctg<br>Leu Trp Pro Ser Pro Leu Met Ile Lys Arg Ser Lys Lys Asn Ser Leu<br>295 300 305 | | 1210 |
| gcc ttg tcc ctg acg gcc gac cag atg gtc agt gcc ttg ttg gat gct<br>Ala Leu Ser Leu Thr Ala Asp Gln Met Val Ser Ala Leu Leu Asp Ala<br>310 315 320 | | 1258 |
| gag ccc ccc ata ctc tat tcc gag tat gat cct acc aga ccc ttc agt<br>Glu Pro Pro Ile Leu Tyr Ser Glu Tyr Asp Pro Thr Arg Pro Phe Ser<br>325 330 335 | | 1306 |
| gaa gct tcg atg atg ggc tta ctg acc aac ctg gca gac agg gag ctg<br>Glu Ala Ser Met Met Gly Leu Leu Thr Asn Leu Ala Asp Arg Glu Leu<br>340 345 350 | | 1354 |
| gtt cac atg atc aac tgg gcg aag agg gtg cca ggc ttt gtg gat ttg<br>Val His Met Ile Asn Trp Ala Lys Arg Val Pro Gly Phe Val Asp Leu<br>355 360 365 370 | | 1402 |
| acc ctc cat gat cag gtc cac ctt cta gaa tgt gcc tgg cta gag atc<br>Thr Leu His Asp Gln Val His Leu Leu Glu Cys Ala Trp Leu Glu Ile<br>375 380 385 | | 1450 |
| ctg atg att ggt ctc gtc tgg cgc tcc atg gag cac cca gtg aag cta<br>Leu Met Ile Gly Leu Val Trp Arg Ser Met Glu His Pro Val Lys Leu<br>390 395 400 | | 1498 |
| ctg ttt gct cct aac ttg ctc ttg gac agg aac cag gga aaa tgt gta<br>Leu Phe Ala Pro Asn Leu Leu Leu Asp Arg Asn Gln Gly Lys Cys Val<br>405 410 415 | | 1546 |
| gag ggc atg gtg gag atc ttc gac atg ctg ctg gct aca tca tct cgg<br>Glu Gly Met Val Glu Ile Phe Asp Met Leu Leu Ala Thr Ser Ser Arg<br>420 425 430 | | 1594 |
| ttc cgc atg atg aat ctg cag gga gag gag ttt gtg tgc ctc aaa tct<br>Phe Arg Met Met Asn Leu Gln Gly Glu Glu Phe Val Cys Leu Lys Ser<br>435 440 445 450 | | 1642 |
| att att ttg ctt aat tct gga gtg tac aca ttt ctg tcc agc acc ctg<br>Ile Ile Leu Leu Asn Ser Gly Val Tyr Thr Phe Leu Ser Ser Thr Leu<br>455 460 465 | | 1690 |
| aag tct ctg gaa gag aag gac cat atc cac cga gtc ctg gac aag atc<br>Lys Ser Leu Glu Glu Lys Asp His Ile His Arg Val Leu Asp Lys Ile<br>470 475 480 | | 1738 |
| aca gac act ttg atc cac ctg atg gcc aag gca ggc ctg acc ctg cag<br>Thr Asp Thr Leu Ile His Leu Met Ala Lys Ala Gly Leu Thr Leu Gln<br>485 490 495 | | 1786 |
| cag cag cac cag cgg ctg gcc cag ctc ctc ctc atc ctc tcc cac atc<br>Gln Gln His Gln Arg Leu Ala Gln Leu Leu Leu Ile Leu Ser His Ile<br>500 505 510 | | 1834 |
| agg cac atg agt aac aaa ggc atg gag cat ctg tac agc atg aag tgc<br>Arg His Met Ser Asn Lys Gly Met Glu His Leu Tyr Ser Met Lys Cys | | 1882 |

-continued

```
             515                 520                 525                 530
aag aac gtg gtg ccc ctc tat gac ctg ctg ctg gag atg ctg gac gcc         1930
Lys Asn Val Val Pro Leu Tyr Asp Leu Leu Leu Glu Met Leu Asp Ala
                535                 540                 545 cac cgc cta cat gcg ccc act agc cgt gga ggg gca tcc gtg gag gag         1978
His Arg Leu His Ala Pro Thr Ser Arg Gly Gly Ala Ser Val Glu Glu
                550                 555                 560 acg gac caa agc cac ttg gcc act gcg ggc tct act tca tcg cat tcc         2026
Thr Asp Gln Ser His Leu Ala Thr Ala Gly Ser Thr Ser Ser His Ser
            565                 570                 575 ttg caa aag tat tac atc acg ggg gag gca gag ggt ttc cct gcc aca         2074
Leu Gln Lys Tyr Tyr Ile Thr Gly Glu Ala Glu Gly Phe Pro Ala Thr
        580                 585                 590 gtc tga gagctccctg gc                                                    2092
Val
595

<210> SEQ ID NO 55
<211> LENGTH: 595
<212> TYPE: PRT
<213> ORGANISM: Homo sapiens
<220> FEATURE:
<221> NAME/KEY: misc_feature
<222> LOCATION: (293)..(832)
<223> OTHER INFORMATION: A/B domain
<220> FEATURE:
<221> NAME/KEY: misc_feature
<222> LOCATION: (833)..(1081)
<223> OTHER INFORMATION: C domain
<220> FEATURE:
<221> NAME/KEY: misc_feature
<222> LOCATION: (1082)..(1198)
<223> OTHER INFORMATION: D domain
<220> FEATURE:
<221> NAME/KEY: misc_feature
<222> LOCATION: (1199)..(1954)
<223> OTHER INFORMATION: E domain
<220> FEATURE:
<221> NAME/KEY: misc_feature
<222> LOCATION: (1955)..(2077)
<223> OTHER INFORMATION: F domain

<400> SEQUENCE: 55

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160
```

```
Gly Arg Glu Arg Leu Ala Ser Thr Asn Asp Lys Gly Ser Met Ala Met
            165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
            210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
            245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
            290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
            325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
            370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
            405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
            450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
            485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
            515                 520                 525

Lys Cys Lys Asn Val Val Pro Leu Tyr Asp Leu Leu Leu Glu Met Leu
            530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
            565                 570                 575
```

```
                         -continued
His Ser Leu Gln Lys Tyr Tyr Ile Thr Gly Glu Ala Glu Gly Phe Pro
            580                 585                 590
Ala Thr Val
        595
```